US 11,478,541 B2

(12) United States Patent
Livengood et al.

(10) Patent No.: US 11,478,541 B2
(45) Date of Patent: Oct. 25, 2022

(54) METHOD FOR INACTIVATING ZIKA VIRUS AND FOR DETERMINING THE COMPLETENESS OF INACTIVATION

(71) Applicant: TAKEDA VACCINES, INC., Cambridge, MA (US)

(72) Inventors: Jill A. Livengood, Cambridge, MA (US); Holli Giebler, Cambridge, MA (US); Hansi Dean, Cambridge, MA (US); Tatsuki Satou, Hikari (JP); Raman Rao, Singapore (SG); Jackie Marks, Cambridge, MA (US); Mark Lyons, Cambridge, MA (US); Asae Shintani, Hikari (JP); James Gifford, Cambridge, MA (US)

(73) Assignee: Takeda Vaccines, Inc., Cambridge, MA (US)

( * ) Notice: Subject to any disclaimer, the term of this patent is extended or adjusted under 35 U.S.C. 154(b) by 0 days.

(21) Appl. No.: 16/761,340

(22) PCT Filed: Nov. 5, 2018

(86) PCT No.: PCT/US2018/059227
§ 371 (c)(1),
(2) Date: May 4, 2020

(87) PCT Pub. No.: WO2019/090233
PCT Pub. Date: May 9, 2019

(65) Prior Publication Data
US 2021/0177959 A1 Jun. 17, 2021

Related U.S. Application Data

(60) Provisional application No. 62/592,995, filed on Nov. 30, 2017, provisional application No. 62/581,500, filed on Nov. 3, 2017.

(51) Int. Cl.
| | |
|---|---|
| *C12N 15/62* | (2006.01) |
| *C12N 15/81* | (2006.01) |
| *C12N 15/85* | (2006.01) |
| *A61K 38/38* | (2006.01) |
| *A61K 39/00* | (2006.01) |
| *A61K 39/12* | (2006.01) |
| *A61P 31/14* | (2006.01) |
| *C12N 7/00* | (2006.01) |
| *A61K 9/00* | (2006.01) |
| *A61K 39/39* | (2006.01) |

(52) U.S. Cl.
CPC .......... *A61K 39/12* (2013.01); *A61K 9/0019* (2013.01); *A61K 39/39* (2013.01); *A61P 31/14* (2018.01); *C12N 7/00* (2013.01); *A61K 2039/5252* (2013.01); *A61K 2039/54* (2013.01); *A61K 2039/545* (2013.01); *A61K 2039/55505* (2013.01); *C12N 2770/24034* (2013.01); *C12N 2770/24071* (2013.01); *C12N 2770/24134* (2013.01); *C12N 2770/24151* (2013.01); *C12N 2770/24163* (2013.01); *C12N 2770/24164* (2013.01)

(58) Field of Classification Search
CPC .. C07K 14/765; C07K 2319/31; A61K 38/00; A61P 31/04; A61P 31/12
See application file for complete search history.

(56) References Cited

U.S. PATENT DOCUMENTS

| | | | |
|---|---|---|---|
| 2007/0110759 | A1 | 5/2007 | Sattentau et al. |
| 2013/0280295 | A1 | 10/2013 | Schlegl et al. |
| 2017/0014502 | A1 | 1/2017 | Sumathy et al. |
| 2020/0360505 | A1 | 11/2020 | Livengood et al. |
| 2021/0106669 | A1 | 4/2021 | Livengood et al. |
| 2021/0177958 | A1 | 6/2021 | Livengood et al. |
| 2021/0403879 | A1 | 12/2021 | Livengood et al. |

FOREIGN PATENT DOCUMENTS

| | | |
|---|---|---|
| BR | 102017024030 A2 | 6/2019 |
| CN | 105749268 A | 7/2016 |
| CN | 107537029 A | 1/2018 |
| CN | 108187036 A | 6/2018 |
| CN | 108210921 A | 6/2018 |
| CN | 108503696 A | 9/2018 |
| CN | 108503697 A | 9/2018 |
| EP | 0 864 646 A2 | 9/1998 |
| EP | 0864646 A2 | 9/1998 |
| EP | 1 724 338 A1 | 11/2006 |
| WO | WO 99/11762 A1 | 3/1999 |
| WO | WO 2007/007344 A1 | 1/2007 |
| WO | WO 2008/026225 A2 | 3/2008 |

(Continued)

OTHER PUBLICATIONS

Reagan, R. L., et al; "Electron Micrographs of Erythrocytes From Swiss Albino Mice Infected With Zika Virus"; From the Virus Laboratory, Live Stock Sani Service, University of Maryland, College Park, Maryland. Received for publication Apr. 28, 1955.

(Continued)

*Primary Examiner* — Barry A Chestnut

(74) *Attorney, Agent, or Firm* — Honigman LLP; Fernando Alberdi; Jonathan P. O'Brien

(57) ABSTRACT

The present disclosure relates to methods for inactivating a Zika virus which can be used in vaccines and immunogenic compositions. The present disclosure also relates to a method for determining the completeness of inactivation of an arbovirus preparation.

17 Claims, 28 Drawing Sheets

Specification includes a Sequence Listing.

(56) References Cited

FOREIGN PATENT DOCUMENTS

| WO | 2010111687 A2 | 9/2010 |
|---|---|---|
| WO | WO 2012/172574 A1 | 12/2012 |
| WO | 2013083726 A1 | 6/2013 |
| WO | WO 2013/083726 A1 | 6/2013 |
| WO | WO 2015/059714 A1 | 4/2015 |
| WO | 2016044023 A1 | 3/2016 |
| WO | WO 2016/063291 A1 | 4/2016 |
| WO | WO 2016/145149 A1 | 9/2016 |
| WO | 2017009873 A1 | 1/2017 |
| WO | 2017015463 A2 | 1/2017 |
| WO | WO 2017/009873 A1 | 1/2017 |
| WO | 2017056094 A1 | 4/2017 |
| WO | 2017070624 A1 | 4/2017 |
| WO | 2017/109223 A1 | 6/2017 |
| WO | 2017109211 A1 | 6/2017 |
| WO | 2017109225 A1 | 6/2017 |
| WO | WO 2017/109223 A1 | 6/2017 |
| WO | WO 2017/109224 A1 | 6/2017 |
| WO | WO 2017/109225 A1 | 6/2017 |
| WO | WO 2017/109227 A1 | 6/2017 |
| WO | WO 2017/109228 A1 | 6/2017 |
| WO | WO2017109223 * | 6/2017 |
| WO | 2017132210 A1 | 8/2017 |
| WO | 2017140905 A1 | 8/2017 |
| WO | 2017147458 A1 | 8/2017 |
| WO | 2017/192856 A | 11/2017 |
| WO | 2017197034 A1 | 11/2017 |
| WO | 2017197035 A1 | 11/2017 |
| WO | 2017208191 A1 | 12/2017 |
| WO | 2017210215 A1 | 12/2017 |
| WO | 2017212291 A1 | 12/2017 |
| WO | 2017214596 A1 | 12/2017 |
| WO | WO 2017/210215 A1 | 12/2017 |
| WO | 2018007575 A1 | 1/2018 |
| WO | 2018020271 A1 | 2/2018 |
| WO | 2018022786 A1 | 2/2018 |
| WO | 2018091540 A1 | 5/2018 |
| WO | 2018115509 A2 | 6/2018 |
| WO | 2018165373 A1 | 9/2018 |
| WO | 2018187799 A1 | 10/2018 |
| WO | 2019068877 A1 | 4/2019 |
| WO | 2019090228 A2 | 5/2019 |
| WO | 2019090233 A1 | 5/2019 |
| WO | 2019090238 A1 | 5/2019 |
| WO | 2019104157 A1 | 5/2019 |
| WO | 2019108970 A1 | 6/2019 |
| WO | 2019108976 A1 | 6/2019 |
| WO | 2019162465 A1 | 8/2019 |
| WO | 2019172982 A1 | 9/2019 |
| WO | 2019186199 A1 | 10/2019 |
| WO | 2019209079 A1 | 10/2019 |
| WO | 2020017765 A1 | 1/2020 |
| WO | 2020226831 A1 | 11/2020 |
| WO | WO 2020/226831 A1 | 11/2020 |
| WO | 2021141758 A1 | 7/2021 |

OTHER PUBLICATIONS

Brett, U.; "Zika-Virus-Infektionen"; Laboratoriumsmedizin; https://www.mta-dialog.de/artikel/zika-virus-infektionen.html; Apr. 1, 2016.
CTRI/2017/05/008539 "A Phase 1 clinical trial to evaluate safety and effectiveness of Zika vaccine in healthy adults.", ctri.nic.in/Clinicaltrials, Jul. 18, 2018, Retrieved from internet Apr. 30, 2022, 6 pages.
Pan American Health Organization (PAHO)/World Health Organization (WHO); "Epidemiological Alert—Zika Virus Infection"; May 7, 2015.
NCT02963909 "A Phase 1, First-in-human, Double-blinded, Randomized, Placebo-controlled Trial of a Zika Virus Purified Inactivated Vaccine (ZPIV) With Alum Adjuvant in Healthy Flavivirus-naive and Flavivirus-Primed Subjects.", Clinical Trials.gov, Nov. 15, 2016, Retrieved from internet Apr. 30, 2022, 12 pages.
Yang, Z., et al; "Culture Conditions and Types of Growth Media for Mammalian Cells"; Intech open science; http://dx.doi.org/10.5772/52301; 2012.
Way, H., et al; "Comparative Studies of some African Arboviruses in Cell Culture and in Mice"; J. gen. Virol; vol. 30; 1976; p. 123-130.
WHO Technical Report; "Guidelines on viral inactivation and removal procedures intended to assure the viral safety of human blood plasma products"; Series No. 924; 2004.
Toriniwa, H., et al; "Long-term stability of Vero cell-derived inactivated Japanese encephalitis vaccine prepared using serum-free medium"; Vaccine vol. 26; 2008; p. 3680-3689.
Database GenBank Accession No. KX601168.1; "Zika virus strain ZIKV/Homo sapiens/PRI/PRVABC59/2015, complete genome", Retrieved from GenBank Accession No. KX601168.1; Jul. 25, 2016, https://www.ncbi.nlm.nih.gov/nuccore/KX601168.1, 5 pages.
Zent, O., et al; "Safety, immunogenicity and tolerability of a new pediatric tick-borne encephalitis (TBE) vaccine, free of protein-derived stabilizer"; Vaccine; vol. 21; (2003); p. 3584 3592.
Database GenBank Accession No. MH158237.1; "Zika virus isolate PRVABC59, complete genome", Retrieved from GenBank Accession No. MH158237.1; May 9, 2018, https://www.ncbi.nlm.nih.gov/nuccore/MH158237.1, 5 pages.
Pinto, A. K., et al; A Hydrogen Peroxide-Inactivated Virus Vaccine Elicits Humoral and Cellular Immunity and Protects against Lethal West Nile Virus Infection in Aged Mice; Journal of Virology, Feb. 2013 vol. 87 No. 4, p. 1926-1936.
Abbink, P. et al., "Zika virus vaccines", Nature. Oct. 2018; 16: 594-600.
Baldwin et al., "Purified Inactivated Zika Vaccine Candidates Afford Protection against Lethal Challenge in Mice," Scientific Reports, vol. 8, No. 1, Nov. 7, 2018 (Nov. 7, 2018).
Barreto-Vieira et al: "Structural investigation of C6/36 and Vero cell cultures infected with a Brazilian Zika virus," PLOS ONE, vol. 12, No. 9, Sep. 12, 2017 (Sep. 12, 2017), p. e0184397.
Blümel et al., "Inactivation and removal of Zika virus during manufacture of plasma-derived medicinal products : Inactivation of Zika Virus", Transfusion., vol. 57, No. 3pt2, Oct. 12, 2016 (Oct. 12, 2016), p. 790-796.
Borucki et al., PLoS One. Dec. 2019; 14 (12): e0225699.
Castanha and Marques, The Lancet, Sep. 2021, vol. 21, pp. 1198-1200.
Druelle, J. et al., "Wild type measles virus attenuation independent of type I IFN", Virology Journal, vol. 5, No. 1, Jan. 1, 2008 (Jan. 1, 2008), p. 22.
Duggal, N. et al., "Mutations present in low-passage Zika virus isolated result in attenuated pathogenesis in mice", Virology. 2019; 530: 19-26.
Faye, O. et al., "Molecular Evolution of Zika Virus during its Emergence", PLoS Neglected Tropical Diseases. 2014; 8 (1): e2636.
GenBank Accession No. KX377337.1, Jun. 22, 2016.
Haddow, A. et al., "Genetic Characterization of Zika Virus Strains: Geographic Expansion of the Asian Lineage", PLoS Neglected Tropical Diseases 2012; 6 (2): e1477.
Han et al., Lancet Infect Dis, 2021, 21:1282-1292.
Marban-Castro, E. et al., "Zika Virus Infection in pregnant women and their children: A review", (European Journal of Obstetrics and Gynecology and Reproductive Biology. 2021; 265: 162-168).
Musso, D. et al., Clinical Microbiology Reviews. Jul. 2016; 29 (3): 487-524.
Narasimhan, H. et al., PLoS Negl Trop Dis, 2020, 14(10):e0008707.
News Release from NIAID on Aug. 3, 2016 for Clinical Trial NCT02840487, available from www.niaid.nih.gov/news-events/nih-begins-testing-investigational-zika-vaccine-humans, accessed Feb. 9, 2022, 7 pages.
Pattnaik, A. et al., "Current Status of Zika Virus Vaccines: Successes and Challenges", Vaccines. 2020; 8 (2): 266.
Shan, C.et al., "A live-attenuated Zika virus vaccine candidate induces sterilizing immunity in mouse models", Nature Medicine, vol. 23, No. 6, Apr. 10, 2017 (Apr. 10, 2017), p. 763-767.

(56) References Cited

OTHER PUBLICATIONS

Tiwari M et al., "Assessment of immunogenic potential of Vero adapted formalin inactivated vaccine derived from novel ECSA genotype of Chikungunya virus", Apr. 21, 2009 (Apr. 21, 2009), vol. 27, No. 18, p. 2513-2522.
Weger-Lucarelli, J. et al., "Development and Characterization of Recombinant Virus Generated from a New World Zika Virus Infectious Clone", Journal of Virology., vol. 91, No. 1, Oct. 19, 2016 (Oct. 19, 2016).
Wilder-Smith, A. et al, "Epidemic arboviral diseases: priorities for research and public health", The Lancet, Dec. 20, 2016 (published online), vol. 17 p. e101-e106.
International Search Report dated Apr. 30, 2019 issued in corresponding Application No. PCT/US2018/059227.
Baldwin, et al., "Purified Inactivated Zika Vaccine Candidates Afford Protection against Lethal Challenge in Mice", Scientific Reports, vol. 8, No. 16509, 2018.
Barreto-Vieira, et al., "Structural investigation of C6/36 and Vero cell cultures infected with a Brazilian Zika virus", Plos One, 2017.
Blumel, et al., "Inactivation and removal of Zika virus during manufacture of plasma-derived medicinal products", Transfusion, vol. 57, 2017.
Tiwari, et al., "Assessment of immunogenic potential of Vero adapted formalin inactivated vaccine derived from novel ECSA genotype of Chikungunya virus", Vaccine, vol. 27, No. 18, pp. 2513-2522, 2009.
Monath, T. P., et al; "An Inactivated Cell-Culture Vaccine against Yellow Fever"; The New England Journal of Medicine 364;14; Apr. 7, 2011.
Mueller, J. A., et al; "Inactivation and Environmental Stability of Zika Virus"; Emerging Infectious Diseases; vol. 22; No. 9; Sep. 2016.
Orlinger, K. K., et al; "An inactivated West Nile Virus vaccine derived from a chemically synthesized cDNA system"; Vaccine vol. 28; (2010); p. 3318-3324.
Pereira, R. C., et al; "An inactivated yellow fever 17DD vaccine cultivated in Vero cell cultures"; Vaccine vol. 33; (2015); p. 4261-4268.
Database GenBank Accession No. MH916806.1; "Zika virus strain ZIKV/Homo sapiens/PRI/PRVABC59_8/2015, complete genome", Retrieved from GenBank Accession No. MH916806.1; Oct. 17, 2018, https://www.ncbi.nlm.nih.gov/nuccore/MH916806.1, 8 pages.
Poore, E. A., et al; "Pre-clinical development of a hydrogen peroxide-inactivated West Nile virus vaccine"; Vaccine; Jan. 5, 2017; 35(2): 283-292; doi:10.1016/j.vaccine.2016.11.080.
Putnak, J. R., et al; "An evaluation of dengue type-2 inactivated, recombinant subunit, and live-attenuated vaccine candidates in the rhesus macaque model"; Vaccine; vol. 23; (2005); p. 4442-4452.
Rey, F. A., et al; "The bright and the dark side of human antibody responses to flaviviruses: lessons for vaccine design"; EMBO reports; vol. 19; No. 2; 2018.
Tiwari, M., et al; "Assessment of immunogenic potential of Vera adapted formalin inactivated vaccine derived from novel ECSA genotype of Chikungunya virus"; Vaccine; vol. 27; (2009); p. 2513-2522.
Trent, D. W.; "Antigenic Characterization of Flavivirus Structural Proteins Separated by Isoelectric Focusing"; Journal of Virology; vol. 22; No. 3; Jun. 1977; p. 608-618.
Wang, W.; "Protein aggregation and its inhibition in biopharmaceutics"; Internaional Journal of Pharmaceutics; vol. 289; (2005); p. 1-30.
NCT02952833 "Zika Vaccine in Naive Subjects", Clinical Trials.gov, Nov. 2, 2016, Retrieved from internet Apr. 30, 2022, 11 pages.
World Health Organization; "WHO global consultation of research related to Zika virus infection"; Mar. 7-9, 2016; www.who.int.
Press Release; World Health Organization; "WHO and experts prioritize vaccines, diagnostics and innovative vector control tools for Zika R&D"; Mar. 9, 2016.
Database GenBank Accession No. MK028857.1; "Zika virus isolate Zika virus/H.sapiens-tc/Puerto Rico/2015/PRVABC59 polyprotein gene, complete cds", Retrieved from GenBank Accession No. MK028857.1; Oct. 17, 2018, https://www.ncbi.nlm.nih.gov/nuccore/MK028857.1, 5 pages.
Brinton, M. A.; "Replication of Flaviviruses"; The Togaviridae and Flaviviridae; Plenum Press; New York; 1986.
Juskewitch, J. E., et al; "Lessons from the Salk Polio Vaccine: Methods for and Risks of Rapid Translation"; CTS Journal; vol. 3; No. 4; p. 182-185, 2010.
Westaway, E. G., et al; "Flaviviridae"; Intervirology vol. 24; p. 183-192; 1985.
NCT04478656 "Safety and Immunogenicity of BBV121 (Zika)", Clinical Trials.gov, Jul. 21, 2020, Retrieved from internet Apr. 30, 2022, 9 pages.
Duggal, N. K., et al; "Mutations present in a low-passage Zika virus isolate result in attenuated pathogenesis in mice"; Virology vol. 530; 2019; p. 19-26.
Lanciotti, R. S., et al; "Phylogeny of Zika Virus in Western Hemisphere, 2015"; Emerging Infectious Diseases; www.cdc.gov/eid; vol. 22; No. 5; May 2016.
Yun, S.-I., et al; "Complete Genome Sequences of Three Historically Important, Spatiotemporally Distinct, and Genetically Divergent Strains of Zika Virus: MR-766, P6-740, and PRVABC-59"; Genome Announcements; vol. 4; Issue 4; Jul./Aug. 2016.
Schmaljohn, A. L., et al; "Chapter 54: Alphaviruses (Togaviridae) and Flaviviruses (Flaviviridae)"; Medical Microbiology; 4th edition; Galveston (TX): University of Texas Medical Branch at Galveston; 1996.
Berger, A.; "Science commentary: Th1 and Th2 responses: what are they?"; BMJ; vol. 321; Aug. 12, 2000.
Demicheli, V., et al; "Vaccines for preventing tick-borne encephalitis (Review)"; Cochrane Database of Systematic Reviews 2009; Issue 1; Art. No. CD000977; 2009.
Eckels, K. H., et al; "Formalin-Inactivated Whole Virus and Recombinant Subunit Flavivirus Vaccines"; Advances in Virus Research; vol. 61; 2003.
Chiron Behring Vaccines; "Fachinformation—Encepur Erwachsene"; Mar. 2005.
NCT03425149 "Randomized, Placebo-controlled, Observer-blinded Phase 1 Safety and Immunogenicity Study of Inactivated Zika Virus Vaccine Candidate in Healthy Adults", Clinical Trials.gov, Feb. 7, 2018, Retrieved from internet Apr. 30, 2022, 9 pages.
Erra, E. O., et al; "The Vero cell-derived, inactivated, SA14-14-2 strain-based vaccine (Ixiaro) for prevention of Japanese encephalitis"; Expert Review of Vaccines; 14(9); p. 1167-1179; Jul. 10, 2015.
Eurosurveillance; "Special edition: Chikungunya and Zika virus"; www.eurosurveillance.org; Oct. 2014.
Fernandez, S., et al; "An Adjuvanted, Tetravalent Dengue Virus Purified Inactivated Vaccine Candidate Induces Long-Lasting and Protective Antibody Responses Against Dengue Challenge in Rhesus Macaques"; Am. J. Trop. Med. Hyg.; vol. 92(4); 2015; p. 698-708; doi:10.4269/ajtmh.14-0268.
Baxter Corporation; "FSME-IMMUN; Tick-Borne Encephalitis Virus Vaccine, Inactivated, with Adjuvant"; Appendix I; Product Monograph Template; Schedule D; Jul. 7, 2010.
Glaxosmithkline; "Fachinformation—Havrix 1440"; Dec. 2008.
Heinz, F. X., et al; "Flaviviruses and flavivirus vaccines"; Vaccine vol. 30; 2012; p. 4301-4306.
Ioos, S., et al; "Current Zika virus epidemiology and recent epidemics"; Medecine et maladies infectieuses vol. 44; 2014; p. 302-307.
Ishikawa, T., et al; "A review of successful flavivirus vaccines and the problems with those flaviviruses for which vaccines are not yet available"; Vaccine vol. 32; 2014; p. 1326-1337.
European Medicines Agency; "Assessment report for Ixiaro"; 2009.
Product Characteristics; "Ixiaro, Annex I".
Larocca, R. A.; "Vaccine protection against Zika virus from Brazil"; Nature; vol. 536; Aug. 25, 2016.
Pivnick, H., et al; "Preservatives for Poliomyelitis (Salk) Vaccine III"; Journal of Pharmaceuticals Sciences; vol. 53; No. 8; p. 899-901; Aug. 1964.
Sanders, B., et al; "Chapter 2; Inactivated Viral Vaccines"; Vaccine Analysis: Strategies, Principles, and Control; DOI 10.1007/978-3-662-45024-6_2; 2015; p. 45-80.

(56) References Cited

OTHER PUBLICATIONS

Database GenBank Accession No. KU501215.1; "Zika virus strain PRVABC59, complete genome", Retrieved from GenBank Accession No. KU501215.1; Feb. 1, 2016, https://www.ncbi.nlm.nih.gov/nuccore/KU501215, 4 pages.
Spellberg, B., et al; "Type 1 / Type 2 Immunity in Infectious Diseases"; Clinical Infectious Diseases; 2001; vol. 32; p. 76-102.
Srivastava, A. K., et al; "A purified inactivated Japanese encephalitis virus vaccine made in vero cells"; Vaccine vol. 19; 2001; p. 4557-4565.
NCT03008122 "Phase 1, Randomized, Double-blinded, Placebo-Controlled Dose De-escalation Study to Evaluate Safety and Immunogenicity of Alum Adjuvanted Zika Virus Purified Inactivated Vaccine (ZPIV) in Adults in a Flavivirus Endemic Area", Clinical Trials.gov, Jan. 2, 2017, Retrieved from internet Apr. 30, 2022, 10 pages.
Press Release; "Walter Reed Scientists Test Zika Vaccine Candidate"; DOD News; Jun. 9, 2016.
Database GenBank Accession No. KY583506.1; "Synthetic construct polyprotein gene, complete cds", Retrieved from GenBank Accession No. KY583506.1; Feb. 6, 2018, https://www.ncbi.nlm.nih.gov/nuccore/KY583506.1, 5 pages.
Shawan, M. M. A. K., et al; "In Silico Modeling and Immunoinformatics Probing Disclose the Epitope Based Peptide Vaccine Against Zika Virus Envelope Glycoprotein"; Indian Journal of Pharmaceutical and Biological Research (IJPBR); vol. 2(4); p. 44-57; 2014.
Database GenBank Accession No. KX087101.3; "Zika virus strain ZIKV/Homo sapiens/PRI/PRVABC59/2015, complete genome", Retrieved from GenBank Accession No. KX087101.3; Nov. 18, 2016, https://www.ncbi.nlm.nih.gov/nuccore/KX087101, 4 pages.
World Health Organization; "Current Zika Product Pipeline"; Product Information; Mar. 3, 2016.
Brown, W. C. et al., "Extended Surface for Membrane Association in Zika Virus NS1 Structure", Nature Structural and Molecular Biology, vol. 23, No. 9, p. 865-867.
Gudlavalleti, S. et al, "Determining trace amounts and the origin of formaldehyde impurity in Neisseria meningitidis A/C/Y/W-135-DT conjugate vaccine formulated in isotonic aqueous 1× PBS by improved C18-UPLC method," Journal of Pharmaceutical and Biomedical Analysis, Mar. 25, 2015, vol. 107, pp. 432-436.
Hassan, J. et al, "Application of low density miniaturized dispersive liquid-liquid extraction method for determination of formaldehyde in aqueous samples (water, fruit juice and Streptococcus vaccine) by HPLC-UV," Journal of Analytical Chemistry, Nov. 21, 2015, vol. 70, pp. 1495-1500.
Martinez, L. J., et al; "Safety and Immunogenicity of a Dengue Virus Serotype-1 Purified-Inactivated Vaccine: Results of a Phase 1 Clinical Trial"; Am. J. Trop. Med. Hyg.; vol. 93(3); 2015; p. 454-460, Copyright © 2015 by The American Society of Tropical Medicine and Hygiene.
Maves, R. C., et al; "Immunogenicity and protective efficacy of a psoralen-inactivated dengue-1 virus vaccine candidate in Aotus nancymaae monkeys"; Vaccine vol. 29; (2011); p. 2691-2696.
Monath, T. P., et al; "Inactivated yellow fever 17D vaccine: Development and nonclinical safety, immunogenicity and protective activity"; Vaccine vol. 28; (2010); p. 3827-3840.
Petersen, L. R., et al; "Zika Virus"; The new england journal of medicine; Mar. 30, 2016; 374:1552-63; DOI: 10.1056/NEJMra1602113; Massachusetts Medical Society.
Pinto, A. K., et al; "A Hydrogen Peroxide-Inactivated Virus Vaccine Elicits Humoral and Cellular Immunity and Protects against Lethal West Nile Virus Infection in Aged Mice"; Journal of Virology p. 1926-1936; Feb. 2013; vol. 87; No. 4.
Press Release; "Crucell Gains Approval and Moves to Recruitment for West Nile Vaccine Phase I Clinical Study"; Leiden, The Netherlands, Dec. 16, 2005.
Hombach, J.; "WHO DRAFT Target Product Profile: A vaccine to protect against congenital Zika virus syndrome in neonates, for use during an emergency"; World Health Organization, Jun. 6, 2016.

Baldwin, W. R., et al; "Purified Inactivated Zika Vaccine Candidates Afford Protection against Lethal Challenge in Mice"; Scientific Reports | (2018) 8:16509 | DOI:10.1038/s41598-018-34735-7.
Han, H. H., et al; "Safety and immunogenicity of a purified inactivated Zika virus vaccine candidate in healthy adults: an observer-blind, randomised, phase 1 trial"; www.thelancet.com/infection; vol. 21; May 18, 2021.
Young, G., et al; "Complete protection in Macaques Conferred by Purified Inactivated Zika Vaccine: Defining a Correlate of protection"; Scientific Reports | (2020) 10:3488 | https://doi.org/10.1038/s41598-020-60415-6.
Abbink, P., et al; "Durability and Correlates of Vaccine Protection Against Zika Virus in Rhesus Monkeys"; Sci Transl Med. Dec. 13, 2017; 9(420); available in PMC Jun. 13, 2018.
Modjarrad, K., et al; "Preliminary aggregate safety and immunogenicity results from three trials of a purified inactivated Zika virus vaccine candidate: phase 1, randomised, double-blind, placebo-controlled clinical trials"; www.thelancet.com; vol. 391; Feb. 10, 2018.
Sumathy, K.; "Protective efficacy of Zika vaccine in AG129 mouse model"; Scientific Reports (2017) | 7:46375 | DOI: 10.1038/srep46375.
Abbink, P., et al; "Protective efficacy of multiple vaccine platforms against Zika virus challenge in rhesus monkeys"; sciencemag.org; Sep. 9, 2016; vol. 353; Issue 6304.
Baronti, C., et al; "Complete Coding Sequence of Zika Virus from a French Polynesia Outbreak in 2013"; Published online Jun. 5, 2014. doi: 10.1128/gen0meA.00500-14.
Cohen, J.; "The race for a Zika vaccine is on"; sciencemag.org; Feb. 5, 2016; vol. 351; Issue 6273.
Cox, B. D.; "Predicting Zika virus structural biology: Challenges and opportunities for intervention"; Antiviral Chemistry and Chemotherapy; 2015, vol. 24(3-4); pp. 118-126.
Hombach, J., et al; Report on a WHO consultation on immunological endpoints for evaluation of new Japanese encephalitis vaccines,WHO, Geneva, Sep. 2-3, 2004; Available online at www.sciencedirect.com; Vaccine vol. 23; (2005) 5205-5211; Jul. 18, 2005.
Lahon, A., et al; "Characterization of a Zika Virus Isolate from Colombia"; PLOS Neglected Tropical Diseases; DOI:10.1371/journal.pntd.0005019; Sep. 21, 2016.
Schlegl, R., et al; "Influence of elemental impurities in aluminum hydroxide adjuvant on the stability of inactivated Japanese Encephalitis vaccine, Ixiaro®"; Vaccine vol. 33 (2015) 5989-5996.
Valneva Press Release; "Valneva Announces Successful Generation of a Highly-purified Zika Vaccine Candidate Using its FDA-EMA Approved Japanese Encephalitis Platform"; Lyon (France); Jul. 7, 2016.
WHO/UNICEF; Zika Virus Vaccine Target Product Profile for Emergency use; "WHO Zika Virus (ZIKV) Vaccine Target Product Profile (TPP): Vaccine to protect against congenital Zika virus syndrome for use during an emergency" Jul. 2016.
Villordo, S. M., et al; "RNA Structure Duplications and Flavivirus Host Adaptation"; Trends in Microbiology, Apr. 2016, vol. 24, No. 4.
Kuno, G., et al; "Full-length sequencing and genomic characterization of Bagaza, Kedougou, and Zika viruses"; Arch Virol (2007) 152: 687-696; DOI 10.1007/s00705-006-0903-z; Printed in The Netherlands.
Musso, D., et al; "Zika Virus"; Clinical Microbiology Reviews; Jul. 2016; vol. 29; No. 3.
Wang, L., et al; "From Mosquitos to Humans: Genetic Evolution of Zika Virus"; Cell Host & Microbe 19; May 11, 2016; Elsevier Inc.
NCT02937233 "Zika Virus Purified Inactivated Vaccine (ZPIV) Accelerated Vaccination Schedule Study (Z001)", Clinical Trials.gov, Oct. 18, 2016, Retrieved from internet Apr. 30, 2022, 11 pages.
Haddow, A. D., "Distinguishing between Zika and Spondweni viruses"; Bull World Health Organ 2016; 94:711-711A; doi: http://dx.doi.org/10.2471/BLT.16.181503.
Dowd, K. A., et al; "Broadly Neutralizing Activity of Zika Virus-Immune Sera Identifies a Single Viral Serotype"; Cells Reports 16; 1485-1491; Aug. 9, 2016.

(56) References Cited

OTHER PUBLICATIONS

Lednicky, J., et al; "Zika Virus Outbreak in Haiti in 2014: Molecular and Clinical Data"; PLOS Neglected Tropical Diseases | DOI:10.1371/journal.pntd.0004687; Apr. 25, 2016.
Sifferlin, A.; "U.S. Launches 'Full-court Press' for a Zika Vaccine"; The Wayback Machine; https://web.archive.org/web/20160122154151/http://time.com/4188973/zika-virus-vaccine-nih/; Jan. 21, 2016.
Intercell AG; Ixiaro; (Japanese Encephalitis Vaccine, Inactivated, Adsorbed); Suspension for Intramuscular Injection; Initial U.S. Approval: 2009.
Bozzo, P., et al; "Vaccination during pregnancy"; Canadian Family Physician (Le Médecin de famille canadien); vol. 57; May 2011.
Pan American Health Organization; "Neurological syndrome, congenital malformations, and Zika virus infection. Implicatons for public health in the Americas"; Epidemiological Alert; Dec. 1, 2015.
Foy, B. D. et al; "Probable Non-Vector-borne Transmission of Zika Virus, Colorado, USA"; Emerging Infectious Diseases; www.cdc.gov/eid; vol. 17; No. 5; May 2011.
Hamel, R., et al; "Biology of Zika Virus Infection in Human Skin Cells"; Journal of Virology; vol. 89; No. 17; Sep. 2015.
Musso, D., et al; "Potential Sexual Transmission of Zika Virus"; Emerging Infectious Diseases; www.cdc.gov/eid; vol. 21; No. 2; Feb. 2015.
Oehler, E., et al; "Zika virus infection complicated by Guillain-Barré syndrome—case report, French Polynesia"; www.eurosurveillance.org; published Mar. 6, 2014.
Press Release; "An Indian biotech company has been developing Zika vaccines for over a year"; https://qz.com/india/609291/this-indian-biotech-firm-is-the-worlds-first-t . . . ; Feb. 4, 2016.
Heang, V., et al; "Zika Virus Infection, Cambodia, 2010"; Emerging Infectious Diseases; www.cdc.gov/eid; vol. 18; No. 2; Feb. 2012.
NCT03343626 "Safety, Immunogenicity, and Dose Ranging Study of Inactivated Zika Virus Vaccine in Healthy Participants", Clinical Trials.gov., Nov. 17, 2017, Retrieved from internet Apr. 30, 2022, 13 pages.
Allison, S. L., et al; "Oligomeric Rearrangement of Tick-Borne Encephalitis Virus Envelope Proteins Induced by an Acidic pH"; Journal of Virology; Feb. 1995; pp. 695-700; vol. 69; No. 2.
Cao-Lormeau, V.-M.; "Tropical Islands as New Hubs for Emerging Arboviruses"; Emerging Infectious Diseases; www.cdc.gov/eid; vol. 22; No. 5; May 2016.
Dai, L., et al; "Molecular Basis of Antibody-Mediated Neutralization and Protection Against Flavivirus"; IUBMB Life; vol. 68; No. 10; Oct. 2016; pp. 783-791.
Firbas, C., et al; "Product review on the JE vaccine Ixiaro"; www.tandfonline.com; Human Vaccines & Immunotherapeutics 11:2, 411-420; Feb. 2015.
Kimura-Kuroda, J., et al; "Protection of Mice Against Japanese Encephalitis Virus by Passive Administration With Monoclonal Antibodies"; The Journal of Immunology; vol. 141. 3606-3610; No. 10; Nov. 15, 1988.
Maves, R. C., et al; "Immunogenicity and protective efficacy of a psoralen-inactivated dengue-1 virus vaccine candidate in Aotus nancymaae monkeys"; Vaccine vol. 29 (2011); 2691-2696.
Metz, S. W., et al; "Oligomeric state of the ZIKV E protein defines protective immune responses"; Nature Communications; 2019; https://doi.org/10.1038/s41467-019-12677-6.
Modis, Y., et al; "Structure of the dengue virus envelope protein after membrane fusion"; Nature; vol. 427; Jan. 22, 2004; www.nature.com/nature.
Excerpt of European Pharmacopoeia 5.4, Vaccines for human use, Apr. 2006, pp. 3838-3840.
Excerpt of European Pharmacopoeia 5.8, Vaccines for human use, Jul. 2007, pp. 5231-5233.
Mitkus et al., "Pharmacokinetic modeling as an approach to assessing the safety of residual formaldehyde in infant vaccines," Vaccine, Jun. 7, 2013, 31:2738-2743.
Product Information IMOVAX® Polio, Alberta Health Services, Polio Vaccine Biological Page, Section 7: Biological Product Information, Standard #: 07.300, Mar. 1, 2013 (revised May 4, 2020), pp. 1-6.
Product Information TDVAX®, Tetanus and Diphtheria Toxoids Adsorbed, NDC 14362-0111-3 and NDC 14362-0111-4, MassBiologics, Sep. 2018, 7 pages.

* cited by examiner

FIG. 6

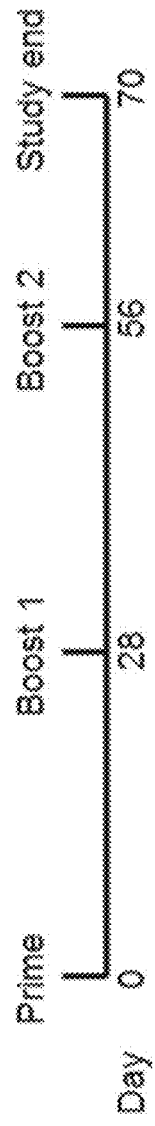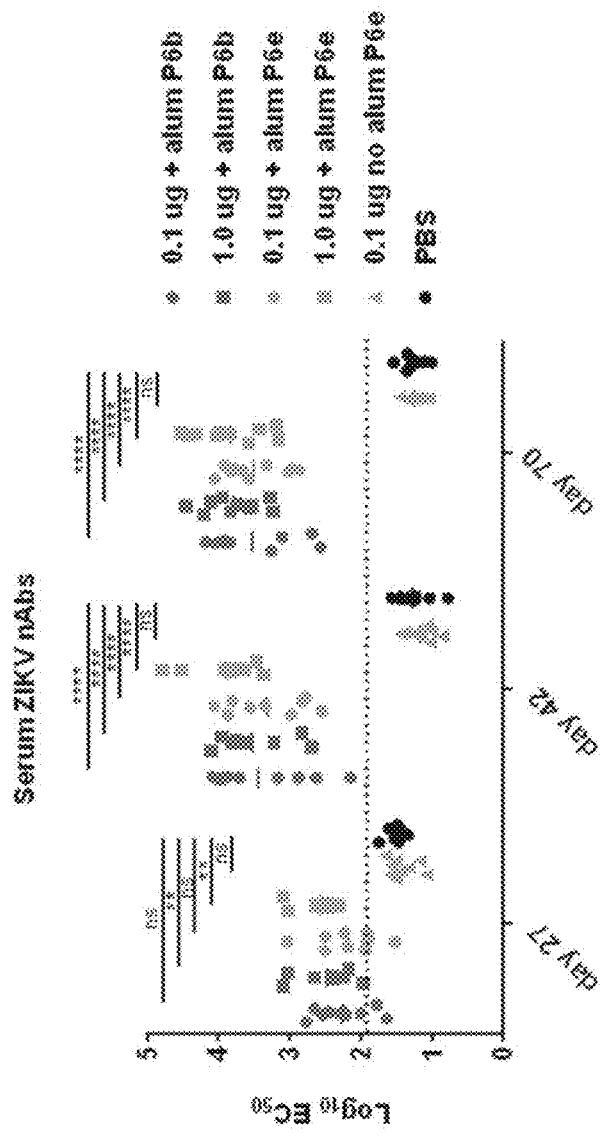
FIG. 12A
FIG. 12B

FIG. 23

FIG. 26
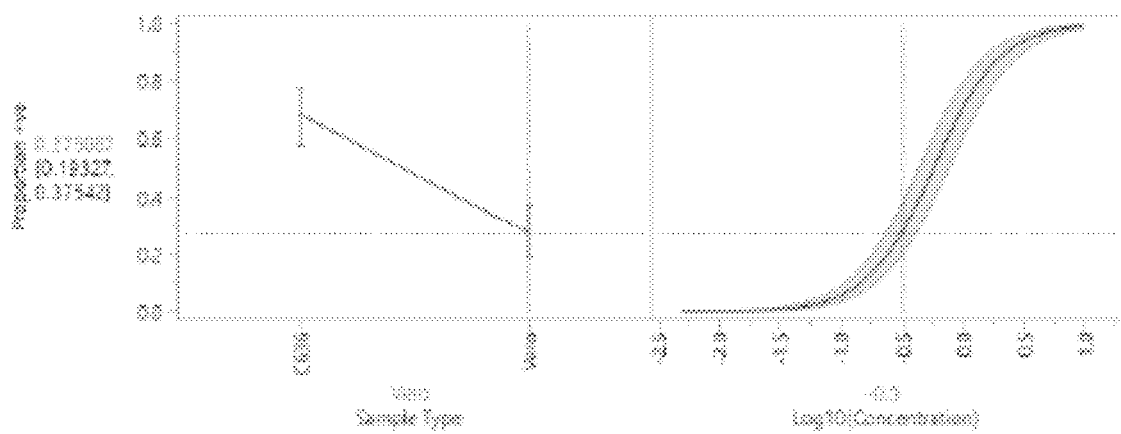
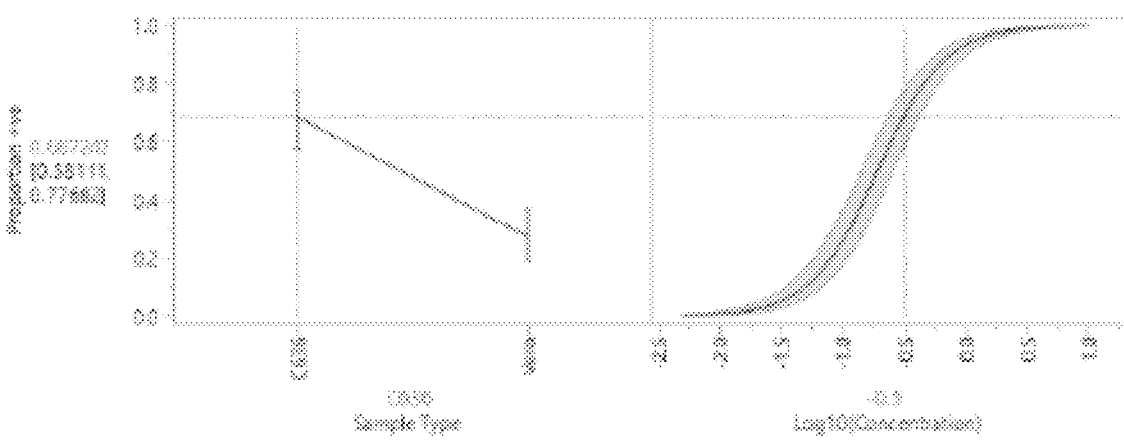

SEQUENCE LISTING

<160> NUMBER OF SEQ ID NOS: 27

<210> SEQ ID NO 1
<211> LENGTH: 351
<212> TYPE: PRT
<213> ORGANISM: Zika virus

<400> SEQUENCE: 1

-continued

```
Asp Val Gly Cys Ser Val Asp Phe Ser Lys Lys Glu Thr Arg Cys Gly
1               5                   10                  15

Thr Gly Val Phe Val Tyr Asn Asp Val Glu Ala Trp Arg Asp Arg Tyr
            20                  25                  30

Lys Tyr His Pro Asp Ser Pro Arg Arg Leu Ala Ala Ala Val Lys Gln
        35                  40                  45

Ala Trp Glu Asp Gly Ile Cys Gly Ile Ser Ser Val Ser Arg Met Glu
    50                  55                  60

Asn Ile Met Trp Arg Ser Val Glu Gly Glu Leu Asn Ala Ile Leu Glu
65                  70                  75                  80

Glu Asn Gly Val Gln Leu Thr Val Val Val Gly Ser Val Lys Asn Pro
                85                  90                  95

Met Trp Arg Gly Pro Gln Arg Leu Pro Val Pro Val Asn Glu Leu Pro
            100                 105                 110

His Gly Trp Lys Ala Trp Gly Lys Ser Tyr Phe Val Arg Ala Ala Lys
        115                 120                 125

Thr Asn Asn Ser Phe Val Val Asp Gly Asp Thr Leu Lys Glu Cys Pro
    130                 135                 140

Leu Lys His Arg Ala Trp Asn Ser Phe Leu Val Glu Asp His Gly Phe
145                 150                 155                 160

Gly Val Phe His Thr Ser Val Trp Leu Lys Val Arg Glu Asp Tyr Ser
                165                 170                 175

Leu Glu Cys Asp Pro Ala Val Ile Gly Thr Ala Val Lys Gly Lys Glu
            180                 185                 190

Ala Val His Ser Asp Leu Gly Tyr Trp Ile Glu Ser Glu Lys Asn Asp
        195                 200                 205

Thr Trp Arg Leu Lys Arg Ala His Leu Ile Glu Met Lys Thr Cys Glu
    210                 215                 220

Trp Pro Lys Ser His Thr Leu Trp Thr Asp Gly Ile Glu Glu Ser Asp
225                 230                 235                 240

Leu Ile Ile Pro Lys Ser Leu Ala Gly Pro Leu Ser His His Asn Thr
                245                 250                 255

Arg Glu Gly Tyr Arg Thr Gln Met Lys Gly Pro Trp His Ser Glu Glu
            260                 265                 270

Leu Glu Ile Arg Phe Glu Glu Cys Pro Gly Thr Lys Val His Val Glu
        275                 280                 285

Glu Thr Cys Gly Thr Arg Gly Pro Ser Leu Arg Ser Thr Thr Ala Ser
    290                 295                 300

Gly Arg Val Ile Glu Glu Trp Cys Cys Arg Glu Cys Thr Met Pro Pro
305                 310                 315                 320

Leu Ser Phe Arg Ala Lys Asp Gly Cys Trp Tyr Gly Met Glu Ile Arg
                325                 330                 335

Pro Arg Lys Glu Pro Glu Ser Asn Leu Val Arg Ser Met Val Thr
            340                 345                 350
```

<210> SEQ ID NO 2
<211> LENGTH: 10675
<212> TYPE: DNA
<213> ORGANISM: Zika virus

<400> SEQUENCE: 2

```
gttgttgatc tgtgtgaatc agactgcgac agttcgagtt tgaagcgaaa gctagcaaca      60
gtatcaacag gttttatttt ggatttggaa acgagagttt ctggtcatga aaaacccaaa     120
```

```
aaagaaatcc ggaggattcc ggattgtcaa tatgctaaaa cgcggagtag cccgtgtgag    180 ccccttggg ggcttgaaga ggctgccagc cggacttctg ctgggtcatg ggcccatcag     240
gatggtcttg gcgattctag cctttttgag attcacggca atcaagccat cactgggtct    300
catcaataga tggggttcag tggggaaaaa agaggctatg gaaacaataa agaagttcaa    360
gaaagatctg gctgccatgc tgagaataat caatgctagg aaggagaaga agagacgagg    420
cgcagatact agtgtcggaa ttgttggcct cctgctgacc acagctatgg cagcggaggt    480
cactagacgt gggagtgcat actatatgta cttggacaga aacgatgctg gggaggccat    540
atcttttcca accacattgg ggatgaataa gtgttatata cagatcatgg atcttggaca    600
catgtgtgat gccaccatga gctatgaatg ccctatgctg gatgaggggg tggaaccaga    660
tgacgtcgat tgttggtgca acacgacgtc aacttgggtt gtgtacgaa cctgccatca     720 caaaaaggt gaagcacgga gatctagaag agctgtgacg ctcccctccc attccaccag    780
gaagctgcaa acgcggtcgc aaacctggtt ggaatcaaga gaatacacaa agcacttgat    840
tagagtcgaa aattggatat tcaggaaccc tggcttcgcg ttagcagcag ctgccatcgc    900
ttggcttttg ggaagctcaa cgagccaaaa agtcatatac ttggtcatga tactgctgat    960
tgccccggca tacagcatca ggtgcatagg agtcagcaat agggactttg tggaaggtat    1020
gtcaggtggg acttgggttg atgttgtctt ggaacatgga ggttgtgtca ccgtaatggc    1080
acaggacaaa ccgactgtcg acatagagct ggttacaaca acagtcagca acatggcgga    1140
ggtaagatcc tactgctatg aggcatcaat atcagacatg gcttctgaca gccgctgccc    1200
aacacaaggt gaagcctacc ttgacaagca atcagacact caatatgtct gcaaaagaac    1260
gttagtggac agaggctggg gaaatggatg tggactttt ggcaaaggga gcctggtgac     1320
atgcgctaag tttgcatgct ccaagaaaat gaccgggaag agcatccagc cagagaatct    1380
ggagtaccgg ataatgctgt cagttcatgg ctcccagcac agtgggatga tcgttaatga    1440
cacaggacat gaaactgatg agaatagagc gaaagttgag ataacgccca attcaccgag    1500
agccgaagcc accctggggg gttttggaag cctaggactt gattgtgaac cgaggacagg    1560
ccttgacttt tcagatttgt attacttgac tatgaataac aagcactggt tggttcacaa    1620
ggagtggttc cacgacattc cattaccttg gcacgctggg gcagacaccg gaactccaca    1680
ctggaacaac aaagaagcac tggtagagtt caaggacgca catgccaaaa ggcaaactgt    1740
cgtggttcta gggagtcaag aaggagcagt tcacacggcc cttgctggag ctctggaggc    1800
tgagatggat ggtgcaaagg gaaggctgtc ctctggccac ttgaaatgtc gcctgaaaat    1860
ggataaactt agattgaagg gcgtgtcata ctccttgtgt actgcagcgt tcacattcac    1920
caagatcccg gctgaaacac tgcacgggac agtcacagtg gaggtacagt acgcagggac    1980
agatggacct tgcaaggttc cagctcagat ggcggtggac atgcaaactc tgaccccagt    2040
tgggaggttg ataaccgcta accccgtaat cactgaaagc actgagaact ctaagatgat    2100
gctggaactt gatccaccat ttgggggactc ttacattgtc ataggagtcg gggagaagaa    2160
gatcacccac cactggcaca ggagtggcag caccattgga aaagcatttg aagccactgt    2220
gagaggtgcc aagagaatgg cagtcttggg agacacagcc tggactttg atcagttgg     2280 aggcgctctc aactcattgg gcaagggcat ccatcaaatt tttggagcag ctttcaaatc    2340
attgtttgga ggaatgtcct ggttctcaca aattctcatt ggaacgttgc tgatgtggtt    2400
gggtctgaac acaaagaatg gatctatttc ccttatgtgc ttggcttag ggggagtgtt     2460 gatcttctta tccacagccg tctctgctga tgtggggtgc tcggtggact tctcaaagaa    2520
```

```
ggagacgaga tgcggtacag gggtgttcgt ctataacgac gttgaagcct ggagggacag    2580
gtacaagtac catcctgact ccccccgtag attggcagca gcagtcaagc aagcctggga    2640
agatggtatc tgcgggatct cctctgtttc aagaatggaa acatcatgt ggagatcagt     2700 agaaggggag ctcaacgcaa tcctggaaga gaatggagtt caactgacgg tcgttgtggg    2760
atctgtaaaa aaccccatgt ggagaggtcc acagagattg cccgtgcctg tgaacgagct    2820
gccccacggc tggaaggctt gggggaaatc gtatttcgtc agagcagcaa agacaaataa    2880
cagctttgtc gtggatggtg acacactgaa ggaatgccca ctcaaacata gagcatggaa    2940
cagctttctt gtggaggatc atgggttcgg ggtatttcac actagtgtct ggctcaaggt    3000
tagagaagat tattcattag agtgtgatcc agccgttatt ggaacagctg ttaagggaaa    3060
ggaggctgta cacagtgatc taggctactg gattgagagt gagaagaatg acacatggag    3120
gctgaagagg gcccatctga tcgagatgaa acatgtgaa tggccaaagt cccacacatt     3180
gtggacagat ggaatagaag agagtgatct gatcataccc aagtctttag ctgggccact    3240
cagccatcac aataccagag agggctacag gacccaaatg aaagggccat ggcacagtga    3300
agagcttgaa attcggtttg aggaatgccc aggcactaag gtccacgtgg aggaaacatg    3360
tggaacaaga ggaccatctc tgagatcaac cactgcaagc ggaagggtga tcgaggaatg    3420
gtgctgcagg gagtgcacaa tgcccccact gtcgttccgg gctaaagatg gctgttggta    3480
tggaatggag ataaggccca ggaaagaacc agaaagcaac ttagtaaggt caatggtgac    3540
tgcaggatca actgatcaca tggaccactt ctcccttgga gtgcttgtga tcctgctcat    3600
ggtgcaggaa gggctgaaga agagaatgac cacaaagatc atcataagca catcaatggc    3660
agtgctggta gctatgatcc tgggaggatt ttcaatgagt gacctggcta agcttgcaat    3720
tttgatgggt gccaccttcg cggaaatgaa cactggagga gatgtagctc atctggcgct    3780
gatagcggca ttcaaagtca gaccagcgtt gctggtatct ttcatcttca gagctaattg    3840
gacaccccgt gaaagcatgc tgctggcctt ggcctcgtgt cttttgcaaa ctgcgatctc    3900
cgccttggaa ggcgacctga tggttctcat caatggtttt gctttggcct ggttggcaat    3960
acgagcgatg gttgttccac gcactgataa catcaccttg gcaatcctgg ctgctctgac    4020
accactggcc cggggcacac tgcttgtggc gtggagagca ggccttgcta cttgcggggg    4080
gtttatgctc ctctctctga agggaaaagg cagtgtgaag aagaacttac catttgtcat    4140
ggccctggga ctaaccgctg tgaggctggt cgaccccatc aacgtggtgg gactgctgtt    4200
gctcacaagg agtgggaagc ggagctggcc ccctagcgaa gtactcacag ctgttggcct    4260
gatatgcgca ttggctggag ggttcgccaa ggcagatata gagatggctg gcccatggc    4320 cgcggtcggt ctgctaattg tcagttacgt ggtctcagga aagagtgtgg acatgtacat    4380
tgaaagagca ggtgacatca tgggaaaaa agatgcggaa gtcactggaa acagtccccg    4440
gctcgatgtg cgcctagatg agagtggtga tttctccctg gtggaggatg acggtccccc    4500
catgagagag atcatactca aggtggtcct gatgaccatc tgtggcatga acccaatagc    4560
catacccttt gcagctggag cgtggtacgt atacgtgaag actggaaaaa ggagtggtgc    4620
tctatgggat gtgcctgctc ccaaggaagt aaaaaagggg gagaccacag atggagtgta    4680
cagagtaatg actcgtagac tgctaggttc aacacaagtt ggagtgggag ttatgcaaga    4740
gggggtcttt cacactatgt ggcacgtcac aaaaggatcc gcgctgagaa gcggtgaagg    4800
gagacttgat ccatactggg gagatgtcaa gcaggatctg gtgtcatact gtggtccatg    4860
```

```
gaagctagat gccgcctggg atgggcacag cgaggtgcag ctcttggccg tgcccccgg   4920 agagagagcg aggaacatcc agactctgcc cggaatattt aagacaaagg atggggacat   4980
tggagcggtt gcgctggatt acccagcagg aacttcagga tctccaatcc tagacaagtg   5040
tgggagagtg ataggacttt atggcaatgg ggtcgtgatc aaaaacggga gttatgttag   5100
tgccatcacc caagggagga gggaggaaga gactcctgtt gagtgcttcg agccctcgat   5160
gctgaagaag aagcagctaa ctgtcttaga cttgcatcct ggagctggga aaaccaggag   5220
agttcttcct gaaatagtcc gtgaagccat aaaaacaaga ctccgtactg tgatcttagc   5280
tccaaccagg gttgtcgctg ctgaaatgga ggaggccctt agagggcttc cagtgcgtta   5340
tatgacaaca gcagtcaatg tcacccactc tggaacagaa atcgtcgact taatgtgcca   5400
tgccaccttc acttcacgtc tactacagcc aatcagagtc cccaactata atctgtatat   5460
tatggatgag gcccacttca cagatccctc aagtatagca gcaagaggat acatttcaac   5520
aagggttgag atgggcgagg cggctgccat cttcatgacc gccacgccac caggaacccg   5580
tgacgcattt ccggactcca actcaccaat tatggacacc gaagtggaag tcccagagag   5640
agcctggagc tcaggctttg attgggtgac ggatcattct ggaaaaacag tttggttttgt   5700 tccaagcgtg aggaacggca atgagatcgc agcttgtctg acaaaggctg aaaacgggt   5760 catacagctc agcagaaaga cttttgagac agagttccag aaaacaaaac atcaagagtg   5820 ggacttttgtc gtgacaactg acatttcaga gatgggcgcc aactttaaag ctgaccgtgt   5880
catagattcc aggagatgcc taaagccggt catacttgat ggcgagagag tcattctggc   5940
tggacccatg cctgtcacac atgccagcgc tgcccagagg agggggcgca taggcaggaa   6000
tcccaacaaa cctggagatg agtatctgta tggaggtggg tgcgcagaga ctgacgaaga   6060
ccatgcacac tggcttgaag caagaatgct ccttgacaat atttacctcc aagatggcct   6120
catagcctcg ctctatcgac ctgaggccga caaagtagca gccattgagg gagagttcaa   6180
gcttaggacg gagcaaagga agacctttgt ggaactcatg aaaagaggag atcttcctgt   6240
ttggctggcc tatcaggttg catctgccgg aataacctac acagatagaa gatggtgctt   6300
tgatggcacg accaacaaca ccataatgga agacagtgtg ccggcagagg tgtggaccag   6360
acacggagag aaaagagtgc tcaaaccgag gtggatggac gccagagttt gttcagatca   6420
tgcggccctg aagtcattca aggagtttgc cgctgggaaa agaggagcgg cttttgagt    6480 gatggaagcc ctgggaacac tgccaggaca catgacagag agattccagg aagccattga   6540
caacctcgct gtgctcatgc gggcagagac tggaagcagg ccttacaaag ccgcggcggc   6600
ccaattgccg gagaccctag agaccataat gcttttgggg ttgctgggaa cagtctcgct   6660
gggaatcttc ttcgtcttga tgaggaacaa gggcataggg aagatgggct ttggaatggt   6720
gactctgggg gccagcgcat ggctcatgtg gctctcggaa attgagccag ccagaattgc   6780
atgtgtcctc attgttgtgt tcctattgct ggtggtgctc atacctgagc cagaaaagca   6840
aagatctccc caggacaacc aaatggcaat catcatcatg gtagcagtag gtcttctggg   6900
cttgattacc gccaatgaac tcggatggtt ggagagaaca aagagtgacc taagccatct   6960
aatgggaagg agagaggagg gggcaaccat aggattctca atggacattg acctgcggcc   7020
agcctcagct tgggccatct atgctgcctt gacaactttc attaccccag ccgtccaaca   7080
tgcagtgacc acctcataca acaactacte cttaatggcg atggccacgc aagctggagt   7140
gttgtttggc atgggcaaag gatgccatt ctacgcatgg gactttggag tcccgctgct   7200
aatgatagct tgctactcac aattaacacc cctgaccta atagtggcca tcattttgct   7260
```

```
cgtggcgcac tacatgtact tgatcccagg gctgcaggca gcagctgcgc gtgctgccca    7320
gaagagaacg gcagctggca tcatgaagaa ccctgttgtg gatggaatag tggtgactga    7380
cattgacaca atgacaattg accccccaagt ggagaaaaag atgggacagg tgctactcat    7440
agcagtagcc gtctccagcg ccatactgtc gcggaccgcc tggggtggg gggaggctgg     7500 ggctctgatc acagccgcaa cttccacttt gtgggaaggc tctccgaaca agtactggaa    7560
ctcctctaca gccacttcac tgtgtaacat ttttagggga agttacttgg ctggagcttc    7620
tctaatctac acagtaacaa gaaacgctgg cttggtcaag agacgtgggg gtggaacagg    7680
agagaccctg ggagagaaat ggaaggcccg cttgaaccag atgtcggccc tggagttcta    7740
ctcctacaaa aagtcaggca tcaccgaggt gtgcagagaa gaggcccgcc gcgccctcaa    7800
ggacggtgtg gcaacgggag gccatgctgt gtcccgagga agtgcaaagc tgagatggtt    7860
ggtggagcgg ggatacctgc agccctatgg aaaggtcatt gatcttggat gtggcagagg    7920
gggctggagt tactacgtcg ccaccatccg caaagttcaa gaagtgaaag gatacacaaa    7980
aggaggccct ggtcatgaag aacccgtgtt ggtgcaaagc tatgggtgga acatagtccg    8040
tcttaagagt ggggtggacg tctttcatat ggcggctgag ccgtgtgaca cgttgctgtg    8100
tgacataggt gagtcatcat ctagtcctga agtggaagaa gcacggacgc tcagagtcct    8160
ctccatggtg ggggattggc ttgaaaaaag accaggagcc ttttgtataa aagtgttgtg    8220
cccatacacc agcactatga tggaaaccct ggagcgactg cagcgtaggt atggggagg     8280 actggtcaga gtgccactct cccgcaactc tacacatgag atgtactggg tctctggagc    8340
gaaaagcaac accataaaaa gtgtgtccac cacgagccag ctcctcttgg ggcgcatgga    8400
cgggcctagg aggccagtga aatatgagga ggatgtgaat ctcggctctg cacgcgggc    8460 tgtggtaagc tgcgctgaag ctcccaacat gaagatcatt ggtaaccgca ttgaaaggat    8520
ccgcagtgag cacgcggaaa cgtggttctt tgacgagaac cacccatata ggacatgggc    8580
ttaccatgga agctatgagg cccccacaca agggtcagcg tcctctctaa taaacggggt    8640
tgtcaggctc ctgtcaaaac cctgggatgt ggtgactgga gtcacaggaa tagccatgac    8700
cgacaccaca ccgtatggtc agcaaagagt tttcaaggaa aaagtggaca ctagggtgcc    8760
agacccccaa gaaggcactc gtcaggttat gagcatggtc tcttcctggt tgtggaaaga    8820
gctaggcaaa cacaaacggc cacgagtctg caccaaagaa gagttcatca acaaggttcg    8880
tagcaatgca gcattagggg caatatttga agaggaaaaa gagtggaaga ctgcagtgga    8940
agctgtgaac gatccaaggt tctgggctct agtggacaag gaaagagagc accacctgag    9000
aggagagtgc cagagctgtg tgtacaacat gatgggaaaa agagaaaaga acaagggga    9060 atttggaaag gccaagggca gccgcgccat ctggtatatg tggctagggg ctagatttct    9120
agagttcgaa gcccttggat tcttgaacga ggatcactgg atgggagag agaactcagg    9180 aggtggtgtt gaagggctgg gattacaaag actcggatat gtcctagaag atgagtcg    9240 tataccagga ggaaggatgt atgcagatga cactgctggc tgggacaccc gcattagcag    9300
gtttgatctg gagaatgaag ctctaatcac caaccaaatg gagaaagggc acagggcctt    9360
ggcattggcc ataatcaagt acacatacca aaacaaagtg gtaaaggtcc ttagaccagc    9420
tgaaaagggg aaaacagtta tggacattat ttcgagacaa gaccaagggg ggagcggaca    9480
agttgtcact tacgctctta acacatttac caacctagtg gtgcaactca ttcggaatat    9540
ggaggctgag gaagttctag agatgcaaga cttgtggctg ctgcggaggt cagagaaagt    9600
```

```
gaccaactgg ttgcagagca acggatggga taggctcaaa cgaatggcag tcagtggaga    9660
tgattgcgtt gtgaagccaa ttgatgatag gtttgcacat gccctcaggt tcttgaatga    9720
tatgggaaaa gttaggaagg acacacaaga gtggaaaccc tcaactggat gggacaactg    9780
ggaagaagtt ccgttttgct cccaccactt caacaagctc catctcaagg acgggaggtc    9840
cattgtggtt ccctgccgcc accaagatga actgattggc cgggcccgcg tctctccagg    9900
ggcgggatgg agcatccggg agactgcttg cctagcaaaa tcatatgcgc aaatgtggca    9960
gctcctttat ttccacagaa gggacctccg actgatggcc aatgccattt gttcatctgt   10020
gccagttgac tgggttccaa ctgggagaac tacctggtca atccatggaa agggagaatg   10080
gatgaccact gaagacatgc ttgtggtgtg aacagagtg tggattgagg agaacgacca    10140
catggaagac aagaccccag ttacgaaatg acagacatt ccctatttgg aaaaaggga    10200 agacttgtgg tgtggatctc tcatagggca cagaccgcgc accacctggg ctgagaacat   10260
taaaaacaca gtcaacatgg tgcgcaggat cataggtgat gaagaaaagt acatggacta   10320
cctatccacc caagttcgct acttgggtga agaagggtct acacctggag tgctgtaagc   10380
accaatctta atgttgtcag gcctgctagt cagccacagc ttggggaaag ctgtgcagcc   10440
tgtgaccccc ccaggagaag ctgggaaacc aagcctatag tcaggccgag aacgccatgg   10500
cacggaagaa gccatgctgc ctgtgagccc ctcagaggac actgagtcaa aaaaccccac   10560
gcgcttggag gcgcaggatg ggaaaagaag gtggcgacct tccccacct tcaatctggg    10620 gcctgaactg gagatcagct gtggatctcc agaagaggga ctagtggtta gagga          10675
```

<210> SEQ ID NO 3
<211> LENGTH: 20
<212> TYPE: DNA
<213> ORGANISM: artificial
<220> FEATURE:
<223> OTHER INFORMATION: oligo 1 (CpG 1826)

<400> SEQUENCE: 3
tccatgacgt tcctgacgtt                                                    20

<210> SEQ ID NO 4
<211> LENGTH: 18
<212> TYPE: DNA
<213> ORGANISM: artificial
<220> FEATURE:
<223> OTHER INFORMATION: oligo 2 (CpG 1758)

<400> SEQUENCE: 4
tctcccagcg tgcgccat                                                      18

<210> SEQ ID NO 5
<211> LENGTH: 30
<212> TYPE: DNA
<213> ORGANISM: artificial
<220> FEATURE:
<223> OTHER INFORMATION: oligo 3

<400> SEQUENCE: 5
accgatgacg tcgccggtga cggcaccacg                                         30

<210> SEQ ID NO 6
<211> LENGTH: 24
<212> TYPE: DNA
<213> ORGANISM: artificial
<220> FEATURE:
<223> OTHER INFORMATION: oligo 4 (CpG 2006)

-continued

```
<400> SEQUENCE: 6
tcgtcgtttt gtcgttttgt cgtt                                          24

<210> SEQ ID NO 7
<211> LENGTH: 20
<212> TYPE: DNA
<213> ORGANISM: artificial
<220> FEATURE:
<223> OTHER INFORMATION: oligo 5 (CpG 1668)

<400> SEQUENCE: 7
tccatgacgt tcctgatgct                                               20

<210> SEQ ID NO 8
<211> LENGTH: 31
<212> TYPE: PRT
<213> ORGANISM: Zika virus

<400> SEQUENCE: 8

Phe Thr Lys Ile Pro Ala Glu Thr Leu His Gly Thr Val Thr Val Glu
1               5                  10                  15

Val Gln Tyr Ala Gly Thr Asp Gly Pro Cys Lys Val Pro Ala Gln
            20                  25                  30

<210> SEQ ID NO 9
<211> LENGTH: 31
<212> TYPE: PRT
<213> ORGANISM: Zika virus

<400> SEQUENCE: 9

Phe Thr Lys Ile Pro Ala Glu Thr Leu His Gly Thr Val Thr Val Glu
1               5                  10                  15

Val Gln Tyr Ala Gly Thr Asp Gly Pro Cys Lys Val Pro Ala Gln
            20                  25                  30

<210> SEQ ID NO 10
<211> LENGTH: 31
<212> TYPE: PRT
<213> ORGANISM: West Nile Virus

<400> SEQUENCE: 10

Phe Leu Gly Thr Pro Ala Asp Thr Gly His Gly Thr Val Val Leu Glu
1               5                  10                  15

Leu Gln Tyr Thr Gly Thr Asp Gly Pro Cys Lys Val Pro Ile Ser
            20                  25                  30

<210> SEQ ID NO 11
<211> LENGTH: 31
<212> TYPE: PRT
<213> ORGANISM: Japanese Encephalitis Virus

<400> SEQUENCE: 11

Phe Ala Lys Asn Pro Ala Asp Thr Gly His Gly Thr Val Val Ile Glu
1               5                  10                  15

Leu Thr Tyr Ser Gly Ser Asp Gly Pro Cys Lys Ile Pro Ile Val
            20                  25                  30

<210> SEQ ID NO 12
<211> LENGTH: 31
<212> TYPE: PRT
<213> ORGANISM: Saint Louis Encephalitis Virus
```

```
<400> SEQUENCE: 12

Phe Ser Lys Asn Pro Ala Asp Thr Gly His Gly Thr Val Ile Val Glu
1               5                   10                  15

Leu Gln Tyr Thr Gly Ser Asn Gly Pro Cys Arg Val Pro Ile Ser
            20                  25                  30

<210> SEQ ID NO 13
<211> LENGTH: 30
<212> TYPE: PRT
<213> ORGANISM: Yellow Fever Virus

<400> SEQUENCE: 13

Phe Val Lys Asn Pro Thr Asp Thr Gly His Gly Thr Val Val Met Gln
1               5                   10                  15

Val Lys Val Ser Lys Gly Ala Pro Cys Arg Ile Pro Val Ile
            20                  25                  30

<210> SEQ ID NO 14
<211> LENGTH: 31
<212> TYPE: PRT
<213> ORGANISM: Dengue virus

<400> SEQUENCE: 14

Leu Glu Lys Glu Val Ala Glu Thr Gln His Gly Thr Val Leu Val Gln
1               5                   10                  15

Val Lys Tyr Glu Gly Thr Asp Ala Pro Cys Lys Ile Pro Phe Ser
            20                  25                  30

<210> SEQ ID NO 15
<211> LENGTH: 31
<212> TYPE: PRT
<213> ORGANISM: Dengue virus

<400> SEQUENCE: 15

Val Val Lys Glu Ile Ala Glu Thr Gln His Gly Thr Ile Val Ile Arg
1               5                   10                  15

Val Gln Tyr Glu Gly Asp Gly Ser Pro Cys Lys Ile Pro Phe Glu
            20                  25                  30

<210> SEQ ID NO 16
<211> LENGTH: 31
<212> TYPE: PRT
<213> ORGANISM: Dengue virus

<400> SEQUENCE: 16

Leu Lys Lys Glu Val Ser Glu Thr Gln His Gly Thr Ile Leu Ile Lys
1               5                   10                  15

Val Glu Tyr Lys Gly Glu Asp Ala Pro Cys Lys Ile Pro Phe Ser
            20                  25                  30

<210> SEQ ID NO 17
<211> LENGTH: 31
<212> TYPE: PRT
<213> ORGANISM: Dengue virus

<400> SEQUENCE: 17

Ile Asp Lys Glu Met Ala Glu Thr Gln His Gly Thr Thr Val Val Lys
1               5                   10                  15

Val Lys Tyr Glu Gly Ala Gly Ala Pro Cys Lys Val Pro Ile Glu
            20                  25                  30
```

-continued

```
<210> SEQ ID NO 18
<211> LENGTH: 29
<212> TYPE: PRT
<213> ORGANISM: Zika virus

<400> SEQUENCE: 18

Ser Val Lys Asn Pro Met Gly Arg Gly Pro Gln Arg Leu Pro Val Pro
1               5                   10                  15

Val Asn Glu Leu Pro His Gly Trp Lys Ala Trp Gly Lys
            20                  25

<210> SEQ ID NO 19
<211> LENGTH: 29
<212> TYPE: PRT
<213> ORGANISM: Zika virus

<400> SEQUENCE: 19

Ser Val Lys Asn Pro Met Trp Arg Gly Pro Gln Arg Leu Pro Val Pro
1               5                   10                  15

Val Asn Glu Leu Pro His Gly Trp Lys Ala Trp Gly Lys
            20                  25

<210> SEQ ID NO 20
<211> LENGTH: 29
<212> TYPE: PRT
<213> ORGANISM: West Nile Virus

<400> SEQUENCE: 20

Lys Gln Glu Gly Met Tyr Lys Ser Ala Pro Lys Arg Leu Thr Ala Thr
1               5                   10                  15

Thr Glu Lys Leu Glu Ile Gly Trp Lys Ala Trp Gly Lys
            20                  25

<210> SEQ ID NO 21
<211> LENGTH: 29
<212> TYPE: PRT
<213> ORGANISM: Japanese Encephalitis Virus

<400> SEQUENCE: 21

Lys Pro Val Gly Arg Tyr Arg Ser Ala Pro Lys Arg Leu Ser Met Thr
1               5                   10                  15

Gln Glu Lys Phe Glu Met Gly Trp Lys Ala Trp Gly Lys
            20                  25

<210> SEQ ID NO 22
<211> LENGTH: 29
<212> TYPE: PRT
<213> ORGANISM: Saint Louis Encephalitis Virus

<400> SEQUENCE: 22

Glu Asp Pro Lys Tyr Tyr Lys Arg Ala Pro Arg Arg Leu Lys Lys Leu
1               5                   10                  15

Glu Asp Glu Leu Asn Tyr Gly Trp Lys Ala Trp Gly Lys
            20                  25

<210> SEQ ID NO 23
<211> LENGTH: 29
<212> TYPE: PRT
<213> ORGANISM: Yellow Fever Virus

<400> SEQUENCE: 23

Asp Pro Lys Asn Val Tyr Gln Arg Gly Thr His Pro Phe Ser Arg Ile
1               5                   10                  15
```

```
Arg Asp Gly Leu Gln Tyr Gly Trp Lys Thr Trp Gly Lys
            20                  25

<210> SEQ ID NO 24
<211> LENGTH: 29
<212> TYPE: PRT
<213> ORGANISM: Dengue virus

<400> SEQUENCE: 24

Asp Val Ser Gly Ile Leu Ala Gln Gly Lys Lys Met Ile Arg Pro Gln
1               5                   10                  15

Pro Met Glu His Lys Tyr Ser Trp Lys Ser Trp Gly Lys
            20                  25

<210> SEQ ID NO 25
<211> LENGTH: 29
<212> TYPE: PRT
<213> ORGANISM: Dengue virus

<400> SEQUENCE: 25

Asp Ile Lys Gly Ile Met Gln Ala Gly Lys Arg Ser Leu Arg Pro Gln
1               5                   10                  15

Pro Thr Glu Leu Lys Tyr Ser Trp Lys Thr Trp Gly Lys
            20                  25

<210> SEQ ID NO 26
<211> LENGTH: 29
<212> TYPE: PRT
<213> ORGANISM: Dengue virus

<400> SEQUENCE: 26

Asp Ile Thr Gly Val Leu Glu Gln Gly Lys Arg Thr Leu Thr Pro Gln
1               5                   10                  15

Pro Met Glu Leu Lys Tyr Ser Trp Lys Thr Trp Gly Lys
            20                  25

<210> SEQ ID NO 27
<211> LENGTH: 29
<212> TYPE: PRT
<213> ORGANISM: Dengue virus

<400> SEQUENCE: 27

Asp Val Lys Gly Val Leu Thr Lys Gly Lys Arg Ala Leu Thr Pro Pro
1               5                   10                  15

Val Asn Asp Leu Lys Tyr Ser Trp Lys Thr Trp Gly Lys
            20                  25
```

METHOD FOR INACTIVATING ZIKA VIRUS AND FOR DETERMINING THE COMPLETENESS OF INACTIVATION

This is a National Phase Application filed under 35 U.S.C. 371 as a national stage of PCT/US2018/059227, filed Nov. 5, 2018, an application claiming the benefit of U.S. Provisional Application No. 62/581,500, filed Nov. 3, 2017 and U.S. Provisional Application No. 62/592,995, filed Nov. 30, 2017, the content of each of which is hereby incorporated by reference in its entirety.

STATEMENT REGARDING FEDERALLY-SPONSORED RESEARCH

This invention was made with government support under Contract No. HHS0100201600015C with the Department of Health and Human Services, Office of the Assistant Secretary for Preparedness and Response, Biomedical Advanced Research and Development Authority. This invention was created in the performance of a Cooperative Research and Development Agreement with the Centers for Disease Control and Prevention, an Agency of the Department of Health and Human Services. The Government of the United States has certain rights in the invention.

FIELD OF THE INVENTION

The Sequence Listing submitted in text format (.txt) on May 4, 2020, named "SequenceListingaspublished.txt", (created on Friday, May 1, 2020, 25 KB), is incorporated herein by reference.

The present disclosure relates to methods for inactivating a Zika virus which can be used in vaccines and immunogenic compositions. The present disclosure also relates to a method for determining the completeness of inactivation of an arbovirus preparation.

BACKGROUND

Zika virus, a flavivirus classified with other mosquito-borne viruses (e.g., yellow fever, dengue, West Nile, and Japanese encephalitis viruses) within the Flaviviridae family has spread rapidly in a hemispheric-wide epidemic since the virus was introduced into Brazil in 2013. The virus has reached the Central and North Americas, including territories of the United States, consequently now threatening the continental US. Indeed, Zika virus strain PRVABC59 was isolated from serum from a person who had traveled to Puerto Rico in 2015. The genome of this strain has been sequenced at least three times (See Lanciotti et al. Emerg. Infect. Dis. 2016 May; 22(5):933-5 and GenBank Accession Number KU501215.1; GenBank Accession Number KX087101.3; and Yun et al. Genome Announc. 2016 Aug. 18; 4(4) and GenBank Accession Number ANK57897.1).

Initially isolated in 1947 in Uganda, the virus was first linked to human disease in 1952, and has been recognized sporadically as a cause of mild, self-limited febrile illness in Africa and Southeast Asia (Weaver et al. (2016) Antiviral Res. 130:69-80; Faria et al. (2016) Science. 352(6283):345-349). However, in 2007, an outbreak appeared in the North Pacific island of Yap, and then disseminated from island to island across the Pacific, leading to an extensive outbreak in 2013-2014 in French Polynesia, spreading then to New Caledonia, the Cook Islands, and ultimately, to Easter Island. An Asian lineage virus was subsequently transferred to the Western Hemisphere by routes that remain undetermined (Faria et al. (2016) Science. 352(6283):345-349). The virus may be transmitted zoonotically by *Aedes aegypti, A. albopictus*, and possibly by *A. hensilli* and *A. polynieseinsis* (Weaver et al. (2016) Antiviral Res. 130:69-80). Additionally, it is thought that other vectors for transmitting the virus may exist, and the virus may be transmitted by blood transfusion, transplacentally, and/or through sexual transmission.

In late 2015, a significant increase in fetal abnormalities (e.g., microcephaly) and Guillain-Barre syndrome (GBS) in areas of widespread Zika virus infection raised alarm that Zika virus might be much more virulent than originally thought, prompting the World Health Organization (WHO) to declare a Public Health Emergency of International Concern (PHEIC) (Heymann et al. (2016) Lancet 387(10020):719-21). While Zika virus poses a substantial public health threat, no FDA-approved vaccine or treatment currently exists, and the only preventative measures for controlling Zika virus involve managing mosquito populations.

In recent efforts to characterize a recombinant Zika virus for the development of a potential vaccine, a non-human cell adapted Zika virus was identified that harbors a mutation in the viral Envelope protein at position 330 (Weger-Lucarelli et al. 2017. Journal of Virology). The authors of this study found that full-length infectious cDNA clones of Zika virus strain PRVABC59 were genetically unstable when amplified during cloning, and opted to split the viral genome to address the observed instability, developing and applying a two plasmid system. However, a two plasmid system for the development of a Zika vaccine is less desirable.

BRIEF SUMMARY

Thus, there is a need to develop vaccines and immunogenic compositions for treating and/or preventing Zika virus infection that utilize a genetically stable Zika virus. One option for the development of a vaccine is to inactivate a whole virus and use this inactivated whole virus for the vaccination of subjects. However, during the development of an inactivated viral vaccine, a key safety assurance is to be certain that no infectious virus remains in the drug product or drug substance. Developing an effective inactivation process and sensitive analytics to measure and determine if infectious virions remain is a key safety aspect for the development of a purified inactivated virus derived from any wild-type virus, but certainly with a pathogenic/encephalitic virus that could cause fetal abnormalities.

The present disclosure is based, at least in part, on the surprising finding that Zika virus can efficiently be inactivated with a low concentration of formaldehyde which is applied to the virus for a relatively short time at room temperature. Additionally, an assay was developed which allows to determine with a high sensitivity whether infectious virions are still present after inactivation.

Accordingly, certain aspects of the present disclosure relate to a method for inactivating a Zika virus preparation comprising:

(a) isolating the Zika virus preparation from one or more cells cultured in vitro, wherein the cells are used to produce the virus preparation; and (b) treating the Zika virus preparation with 0.005% to 0.02% w/v of formaldehyde.

In some embodiments, the cells are non-human cells. In some embodiments, the Zika virus preparation is treated with 0.01% formaldehyde. In some embodiments, the Zika virus preparation is treated for eight to twelve days, such as for ten days. In some embodiments, the Zika virus preparation is treated at a temperature of 15° C. to 30° C., such as a temperature of 22° C.

The method may further comprise a step (c) of determining the completeness of inactivation. In some embodiments, step (c) comprises:

(i) inoculating cultured insect cells with a Zika virus preparation treated with 0.005% to 0.02% w/v of formaldehyde and incubating the insect cells for a first period of time, thereby producing an insect cell supernatant;
(ii) inoculating cultured mammalian cells with the insect cell supernatant produced in (i) and incubating the mammalian cells for a second period of time; and
(iii) determining whether the Zika virus preparation contains a residual replicating virus that produces a cytopathic effect on the mammalian cells.

In some embodiments, the insect cells are selected from CCL-125 cells, Aag-2 cells, RML-12 cells, C6/36 cells, C7-10 cells, AP-61 cells, A.t. GRIP-1 cells, A.t. GRIP-2 cells, A.t. GRIP-3 cells, UM-AVE1 cells, Mos.55 cells, Sua1B cells, 4a-3B cells, Mos.42 cells, MSQ43 cells, LSB-AA695BB cells, NIID-CTR cells and TRA-171 cells, such as C6/36 cells.

In some embodiments, the first period of time is 3 to 7 days.

In some embodiments, the mammalian cells are selected from VERO cells, LLC-MK2 cells, MDBK cells, MDCK cells, ATCC CCL34 MDCK (NBL2) cells, MDCK 33016 (deposit number DSM ACC 2219 as described in WO97/37001) cells, BHK21-F cells, HKCC cells, and Chinese hamster ovary cells (CHO cells), such as VERO cells.

In some embodiments, the second period of time is 3 to 14 days.

The method may further comprise a step (d) of neutralizing the formaldehyde-treated Zika virus preparation with sodium metabisulfite, such as neutralizing the formaldehyde-treated Zika virus preparation at least five, at least seven, at least nine, at least 11, or at least 14 days after formaldehyde treatment.

The method may further comprise a step (e) of preparing a pharmaceutical composition comprising the inactivated Zika virus.

In some embodiments, the treated Zika virus preparation is mixed with an adjuvant. The adjuvant may be selected from the group consisting of aluminum salts, toll-like receptor (TLR) agonists, monophosphoryl lipid A (MLA), synthetic lipid A, lipid A mimetics or analogs, MLA derivatives, cytokines, saponins, muramyl dipeptide (MDP) derivatives, CpG oligos, lipopolysaccharide (LPS) of gram-negative bacteria, polyphosphazenes, emulsions, virosomes, cochleates, poly(lactide-co-glycolides) (PLG) microparticles, poloxamer particles, microparticles, liposomes, Complete Freund's Adjuvant (CFA), and Incomplete Freund's Adjuvant (IFA).

In some embodiments, the adjuvant is an aluminum salt, such as aluminum phosphate, aluminum hydroxide, potassium aluminum sulfate, and Alhydrogel 85.

In some embodiments, at least 75%, at least 85%, at least 90%, at least 95%, at least 96%, at least 97%, at least 98%, at least 99%, or 100% of one or more antigens in the treated virus preparation are adsorbed to the adjuvant.

In some embodiments, the Zika virus comprises a mutation at position 98 of SEQ ID NO: 1 or at a position corresponding to position 98 of SEQ ID NO: 1, such as a Trp98Gly mutation in SEQ ID NO: 1.

In some embodiments, the Zika virus does not comprise a mutation in the envelope protein (E). In some embodiments, the sequence encoding the envelope protein is the same as the corresponding sequence in SEQ ID NO: 2.

Some aspects of the present disclosure relate to a pharmaceutical composition comprising an inactivated Zika virus obtainable by any of the methods disclosed herein.

Some aspects of the present disclosure relate to a pharmaceutical composition comprising an inactivated Zika virus and having a residual formalin content of less than 0.5 µg/ml.

In some embodiments, the pharmaceutical composition is obtainable by any of the methods disclosed herein.

Some aspects of the present disclosure relate to a method for determining the residual formalin content in a pharmaceutical composition comprising an inactivated virus, comprising the steps of:

(a) providing a pharmaceutical composition comprising a virus which has been treated with formaldehyde;
(b) mixing the pharmaceutical composition of (a) with phosphoric acid and 2,4-dinitrophenyl-hydrazine (DNPH), thereby providing a mixture;
(c) incubating the mixture of (b) under suitable conditions; and
(d) analyzing the mixture for the presence of residual formalin.

In some embodiments, the pharmaceutical composition contains an adjuvant. In some embodiments, the pharmaceutical composition contains aluminum hydroxide as adjuvant. In some embodiments, the pharmaceutical composition contains 0.1 mg/ml to 1.0 mg/ml aluminum hydroxide as adjuvant. In some embodiments, the pharmaceutical composition contains 0.4 mg/ml aluminum hydroxide as adjuvant.

In some embodiments, a volume of 1 ml of the pharmaceutical composition of (a) is mixed with 20 µl of 15 to 25% (v/v) phosphoric acid and 50 µl of 0.9 to 1.1 mg/ml DNPH. In some embodiments, a volume of 1 ml of the pharmaceutical composition of (a) is mixed with 20 µl of 20% (v/v) phosphoric acid and 50 µl of 1.0 mg/ml DNPH.

In some embodiments, the mixture of the pharmaceutical composition of (a) with phosphoric acid and 2,4-dinitrophenylhydrazine (DNPH) is incubated at room temperature. In some embodiments, the mixture of the pharmaceutical composition of (a) with phosphoric acid and 2,4-dinitrophenylhydrazine (DNPH) is incubated for 10 to 30 minutes. In some embodiments, the mixture of the pharmaceutical composition of (a) with phosphoric acid and 2,4-dinitrophenylhydrazine (DNPH) is incubated at room temperature for 20 minutes.

In some embodiments, the mixture of the pharmaceutical composition of (a) with phosphoric acid and 2,4-dinitrophenylhydrazine (DNPH) is analyzed by HPLC. In some embodiments, the HPLC is reversed-phase HPLC. In some embodiments, a mixture of water and acetonitrile (1:1, v/v) is used as a mobile phase in HPLC. In some embodiments, the detection wavelength is 360 nm.

In some embodiments, the virus is an inactivated Zika virus. In some embodiments, the inactivated Zika virus has been treated with 0.01% (w/v) formaldehyde for 10 days at 22° C. In some embodiments, the Zika virus comprises a mutation at position 98 of SEQ ID NO: 1 or at a position corresponding to position 98 of SEQ ID NO: 1, such as a Trp98Gly mutation in SEQ ID NO: 1.

Some aspects of the present disclosure relate to a method for determining the completeness of inactivation of an arbovirus preparation, comprising the steps of:

(i) inoculating cultured insect cells with an arbovirus preparation which was subjected to an inactivation step and incubating the insect cells for a first period of time, thereby producing an insect cell supernatant;
(ii) inoculating cultured mammalian cells with the insect cell supernatant produced in (i) and incubating the mammalian cells for a second period of time; and
(iii) determining whether the arbovirus preparation contains a residual replicating virus that produces a cytopathic effect on the mammalian cells.

In some embodiments, the arbovirus is a flavivirus or an alphavirus. In some embodiments, the arbovirus is a Zika virus, a West Nile virus, a Yellow Fever virus, a Japanese Encephalitis virus, tick borne encephalitis virus, a dengue virus, a St. Louis Encephalitis virus, a Chikungunya virus, a O'nyong'nyong virus or a Mayarovirus.

In some embodiments, the arbovirus preparation was subjected to an inactivation step with detergent, formalin, hydrogen peroxide, beta-propiolactone (BPL), binary ethylamine (BEI), acetyl ethyleneimine, methylene blue, or psoralen.

In some embodiments, the insect cells are selected from CCL-125 cells, Aag-2 cells, RML-12 cells, C6/36 cells, C7-10 cells, AP-61 cells, A.t. GRIP-1 cells, A.t. GRIP-2 cells, A.t. GRIP-3 cells, UM-AVE1 cells, Mos.55 cells, Sua1B cells, 4a-3B cells, Mos.42 cells, MSQ43 cells, LSB-AA695BB cells, NIID-CTR cells and TRA-171 cells, such as C6/36 cells.

In some embodiments, the first period of time is 3 to 7 days.

In some embodiments, the mammalian cells are selected from VERO cells, LLC-MK2 cells, MDBK cells, MDCK cells, ATCC CCL34 MDCK (NBL2) cells, MDCK 33016 (deposit number DSM ACC 2219 as described in WO97/37001) cells, BHK21-F cells, HKCC cells, and Chinese hamster ovary cells (CHO cells), such as VERO cells.

In some embodiments, the second period of time is 3 to 14 days.

In some embodiments, the method is capable of detecting less than 1.0 TCID50 of the arbovirus.

BRIEF DESCRIPTION OF THE DRAWINGS

FIG. 6 shows an amino acid sequence alignment comparing the envelope glycoprotein sequence of Zika virus near residue 330 from Zika virus strains PRVABC59 P6e (SEQ ID NO: 8) and PRVABC59 (SEQ ID NO: 9) with several other flaviviruses (WNV (SEQ ID NO: 10); JEV (SEQ ID NO: 11); SLEV (SEQ ID NO: 12); YFV (SEQ ID NO: 13); DENV 1 16007 (SEQ ID NO: 14); DENV 2 16681 (SEQ ID NO: 15); DENV 3 16562 (SEQ IDNO: 16); and DENV 4 1036 (SEQ ID NO: 17)).

FIG. 12A shows the schedule of dosing of CD-1 mice with vaccine formulations derived from the ZIKAV PRVABC59 P6b and P6e clones. PBS was used as placebo.

FIG. 12B shows the serum ZIKAV neutralizing antibody titers of CD-1 mice immunized as described in FIG. 12A using vaccine formulations derived from ZIKAV PRVABC59 P6b and P6e clones. ZIKAV neutralizing antibody titers were determined by Reporter Virus Particle (RVP) neutralization assay. Solid lines represent the geometric mean of a group. The limit of detection (1.93 $\log_{10}$) is represented by a dashed line.

Figure 23:
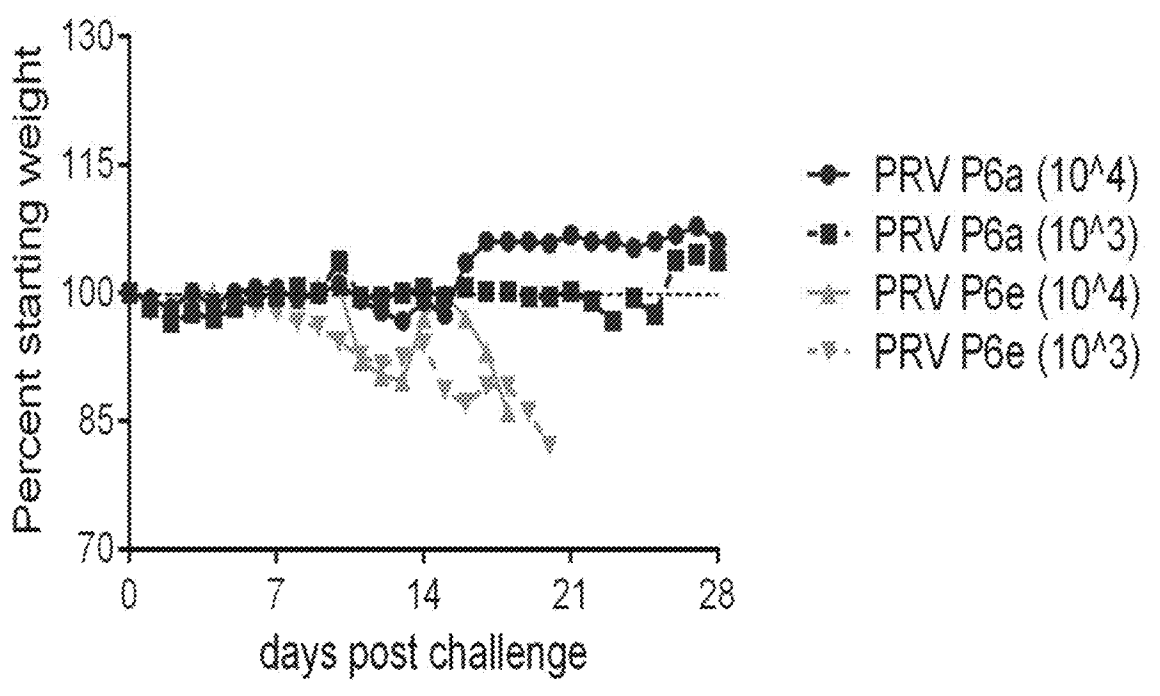

FIG. 23 shows the mean body weight as expressed in percentage of starting weight at time of invention after infection with Zika virus preMVS stocks of P6a and P6e. The dashed line represents 100% of starting weight for reference.

FIG. 26 shows a comparison of C6/36 and Vero sensitivity in the assay as demonstrated with an input virus titer of 0.31 TCID50.

DETAILED DESCRIPTION

General Techniques

Figure 1:
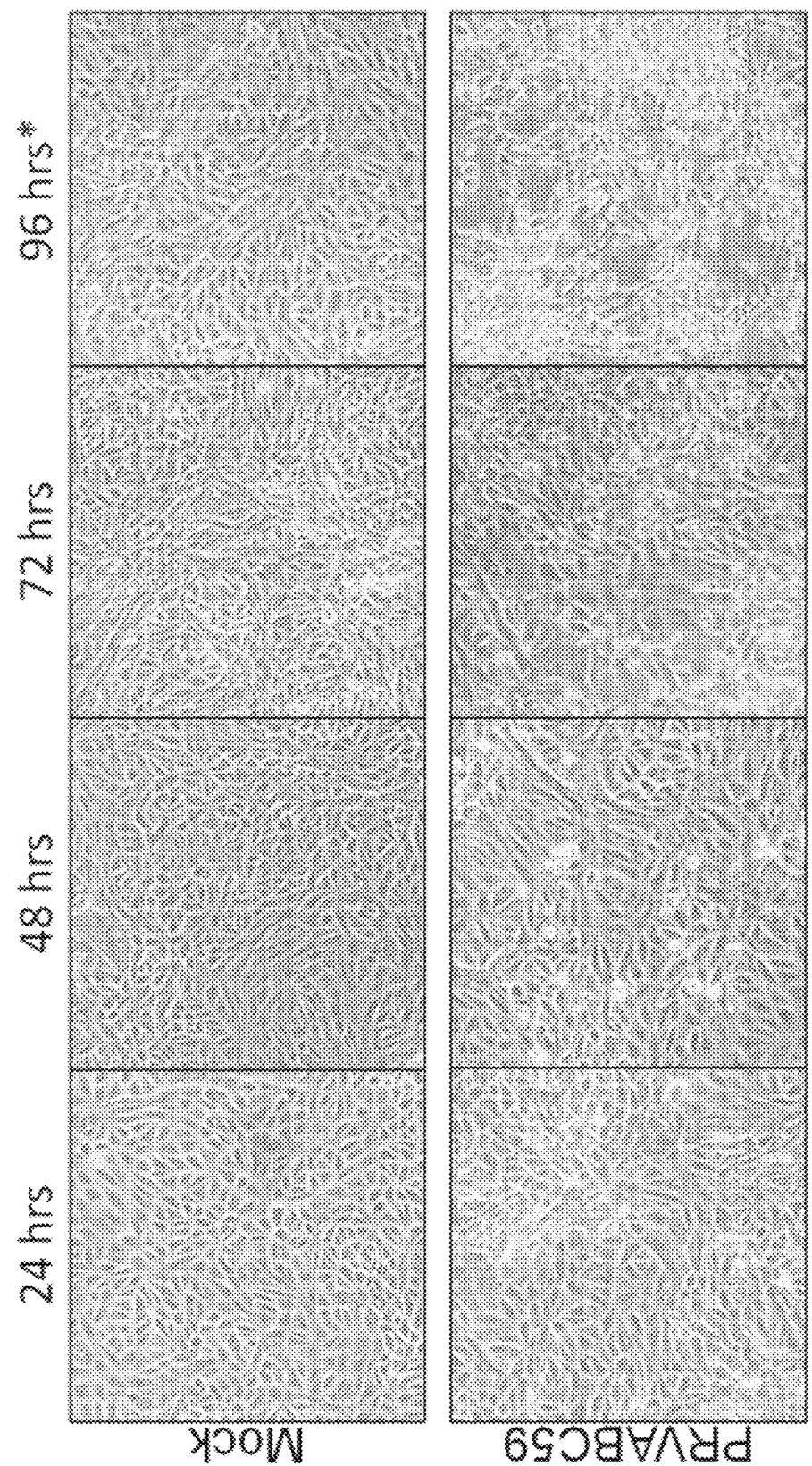
FIG. 1 shows bright field microscopy images of Vero cell monolayers mock infected (top) or infected with ZIKAV strain PRVABC59 (bottom).
Figure 2:
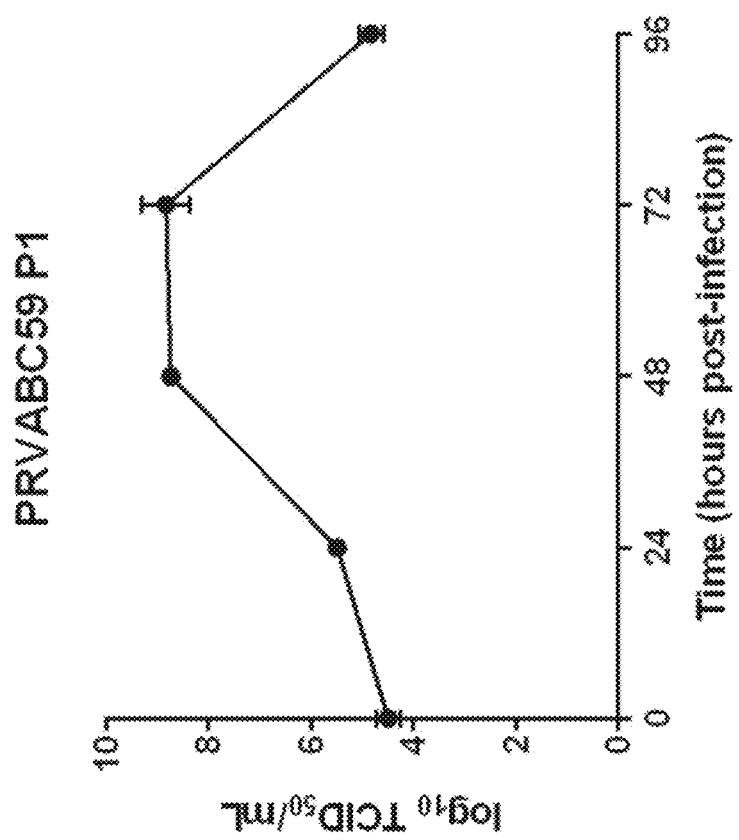
FIG. 2 shows growth kinetics of ZIKAV PRVABC59 P1 on Vero cell monolayers, as determined by $TCID_{50}$.
Figure 3:
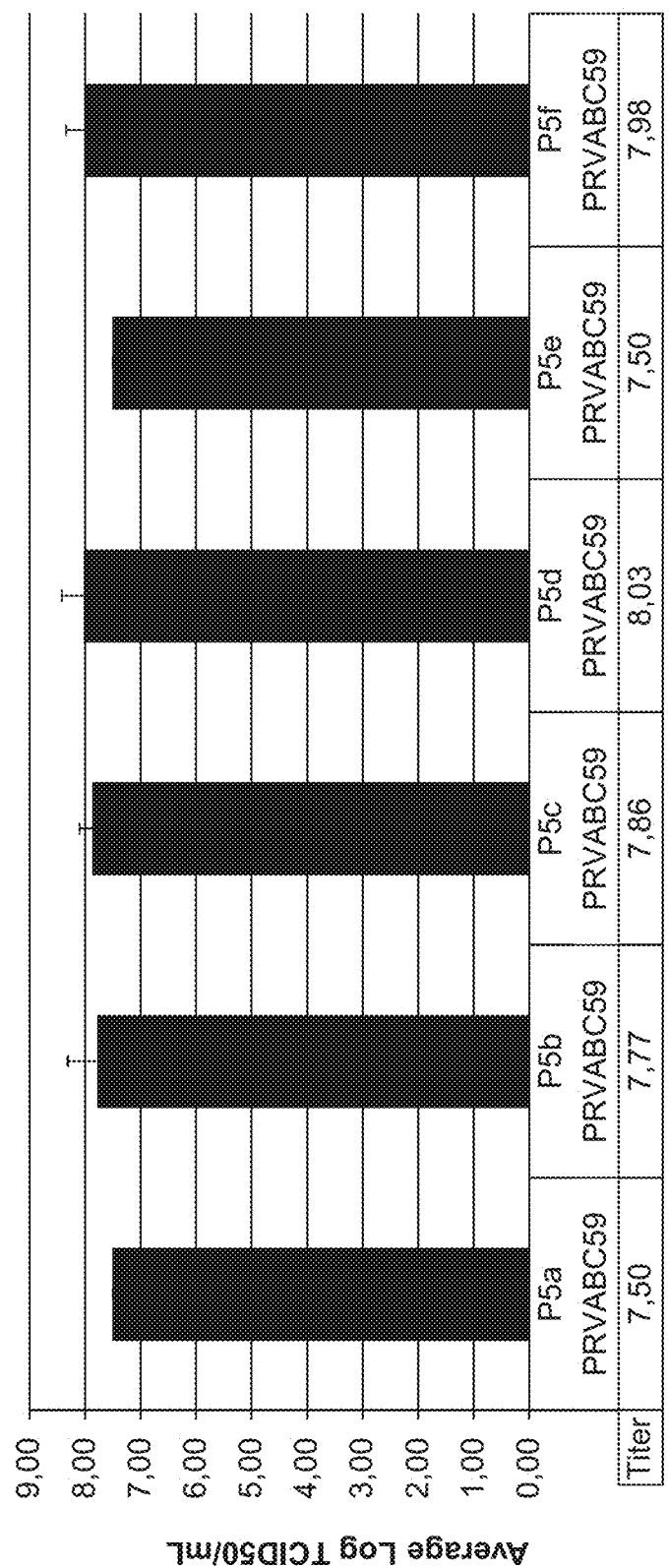
FIG. 3 shows potency assay testing ($TCID_{50}$) of Zika virus PRVABC59 P5 clones a-f.

The techniques and procedures described or referenced herein are generally well understood and commonly employed using conventional methodology by those skilled in the art, such as, for example, the widely utilized methodologies described in Sambrook et al., *Molecular Cloning: A Laboratory Manual* 3d edition (2001) Cold Spring Harbor Laboratory Press, Cold Spring Harbor, N.Y.; *Current Protocols in Molecular Biology* (F. M. Ausubel, et al. eds., (2003)); the series *Methods in Enzymology* (Academic Press, Inc.): *PCR 2: A Practical Approach* (M. J. MacPherson, B. D. Hames and G. R. Taylor eds. (1995)), Harlow and Lane, eds. (1988) *Antibodies, A Laboratory Manual*, and *Animal Cell Culture* (R. I. Freshney, ed. (1987)); *Oligonucleotide Synthesis* (M. J. Gait, ed., 1984); *Methods in Molecular Biology*, Humana Press; *Cell Biology: A Laboratory Notebook* (J. E. Cellis, ed., 1998) Academic Press; *Animal Cell Culture* (R. I. Freshney), ed., 1987); *Introduction to Cell and Tissue Culture* (J. P. Mather and P. E. Roberts, 1998) Plenum Press; *Cell and Tissue Culture: Laboratory Procedures* (A. Doyle, J. B. Griffiths, and D. G. Newell, eds., 1993-8) J. Wiley and Sons; *Handbook of Experimental Immunology* (D. M. Weir and C. C. Blackwell, eds.); *Gene Transfer Vectors for Mammalian Cells* (J. M. Miller and M. P. Calos, eds., 1987); *PCR: The Polymerase Chain Reaction*, (Mullis et al., eds., 1994); *Current Protocols in Immunology* (J. E. Coligan et al., eds., 1991); *Short Protocols in Molecular Biology* (Wiley and Sons, 1999); *Immunobiology* (C. A. Janeway and P. Travers, 1997); *Antibodies* (P. Finch, 1997); *Antibodies: A Practical Approach* (D. Catty, ed., IRL Press, 1988-1989); *Monoclonal Antibodies: A Practical Approach* (P. Shepherd and C. Dean, eds., Oxford University Press, 2000); *Using Antibodies: A Laboratory Manual* (E. Harlow and D. Lane (Cold Spring Harbor Laboratory Press, 1999); and *The Antibodies* (M. Zanetti and J. D. Capra, eds., Harwood Academic Publishers, 1995).

Zika Virus

Certain aspects of the present disclosure relate to a purified inactivated whole Zika virus that may be useful in vaccines and/or immunogenic compositions.

Zika virus (ZIKV) is a mosquito-borne flavivirus first isolated from a sentinel rhesus monkey in the Zika Forest in Uganda in 1947. Since that time, isolations have been made from humans in both Africa and Asia, and more recently, the Americas. ZIKV is found in two (possibly three) lineages: an African lineage (possibly separate East and West African lineages) and an Asian lineage. Accordingly, examples of suitable Zika viruses of the present disclosure include, without limitation, viruses from the African and/or Asian lineages. In some embodiments, the Zika virus is an African lineage virus. In some embodiments, the Zika virus is an Asian lineage virus. Additionally, multiple strains within the African and Asian lineages of Zika virus have been previously identified. Any one or more suitable strains of Zika virus known in the art may be used in the present disclosure, including, for examples, strains Mr 766, ArD 41519, IbH 30656, P6-740, EC Yap, FSS13025, ArD 7117, ArD 9957, ArD 30101, ArD 30156, ArD 30332, HD 78788, ArD 127707, ArD 127710, ArD 127984, ArD 127988, ArD 127994, ArD 128000, ArD 132912, 132915, ArD 141170, ArD 142623, ArD 149917, ArD 149810, ArD 149938, ArD 157995, ArD 158084, ArD 165522, ArD 165531, ArA 1465, ArA 27101, ArA 27290, ArA 27106, ArA 27096, ArA 27407, ArA 27433, ArA 506/96, ArA 975-99, Ara 982-99, ArA 986-99, ArA 2718, ArB 1362, Nigeria68, Malaysia66, Kedougou84, Suriname, MR1429, PRVABC59, ECMN2007, DakAr41524, H/PF/2013, R103451, 103344, 8375, JMB-185, ZIKV/H, sapiens/Brazil/Natal/2015, SPH2015, ZIKV/Hu/Chiba/S36/2016, and/or Cuba2017. In some embodiments, strain PRVABC59 is used in the present disclosure.

In some embodiments, an example of a Zika virus genome sequence is set forth below as SEQ ID NO: 2:

```
  1  gttgttgatc tgtgtgaatc agactgcgac agttcgagtt tgaagcgaaa gctagcaaca
 61  gtatcaacag gttttatttt ggatttggaa acgagagttt ctggtcatga aaacccaaa
121  aaagaaatcc ggaggattcc ggattgtcaa tatgctaaaa cgcggagtag cccgtgtgag
181  ccccttggg ggcttgaaga ggctgccagc cggacttctg ctgggtcatg ggcccatcag
241  gatggtcttg gcgattctag ccttttgag attcacggca atcaagccat cactgggtct
301  catcaataga tggggttcag tggggaaaaa agaggctatg gaaacaataa agaagttcaa
361  gaaagatctg gctgccatgc tgagaataat caatgctagg aaggagaaga gagacgagg
421  cgcagatact agtgtcggaa ttgttggcct cctgctgacc acagctatgg cagcggaggt
481  cactagacgt gggagtgcat actatatgta cttggacaga aacgatgctg gggaggccat
541  atcttttcca accacattgg ggatgaataa gtgttatata cagatcatgg atcttggaca
```

-continued

```
 601 catgtgtgat gccaccatga gctatgaatg ccctatgctg gatgaggggg tggaaccaga
 661 tgacgtcgat tgttggtgca acacgacgtc aacttgggtt gtgtacggaa cctgccatca
 721 caaaaaaggt gaagcacgga gatctagaag agctgtgacg ctcccctccc attccaccag
 781 gaagctgcaa acgcggtcgc aaacctggtt ggaatcaaga gaatacacaa agcacttgat
 841 tagagtcgaa aattggatat tcaggaaccc tggcttcgcg ttagcagcag ctgccatcgc
 901 ttggcttttg ggaagctcaa cgagccaaaa agtcatatac ttggtcatga tactgctgat
 961 tgccccggca tacagcatca ggtgcatagg agtcagcaat agggactttg tggaaggtat
1021 gtcaggtggg acttgggttg atgttgtctt ggaacatgga ggttgtgtca ccgtaatggc
1081 acaggacaaa ccgactgtcg acatagagct ggttacaaca acagtcagca acatggcgga
1141 ggtaagatcc tactgctatg aggcatcaat atcagacatg gcttctgaca gccgctgccc
1201 aacacaaggt gaagcctacc ttgacaagca atcagacact caatatgtct gcaaaagaac
1261 gttagtggac agaggctggg gaaatggatg tggactttt ggcaaaggga gcctggtgac
1321 atgcgctaag tttgcatgct ccaagaaaat gaccgggaag agcatccagc cagagaatct
1381 ggagtaccgg ataatgctgt cagttcatgg ctcccagcac agtgggatga tcgttaatga
1441 cacaggacat gaaactgatg agaatagagc gaaagttgag ataacgccca attcaccgag
1501 agccgaagcc accctggggg gttttggaag cctaggactt gattgtgaac cgaggacagg
1561 ccttgacttt tcagatttgt attacttgac tatgaataac aagcactggt tggttcacaa
1621 ggagtggttc cacgacattc cattaccttg gcacgctggg gcagacaccg gaactccaca
1681 ctggaacaac aaagaagcac tggtagagtt caaggacgca catgccaaaa ggcaaactgt
1741 cgtggttcta gggagtcaag aaggagcagt tcacacggcc cttgctggag ctctggaggc
1801 tgagatggat ggtgcaaagg gaaggctgtc ctctggccac ttgaaatgtc gcctgaaaat
1861 ggataaactt agattgaagg gcgtgtcata ctccttgtgt actgcagcgt tcacattcac
1921 caagatcccg gctgaaacac tgcacgggac agtcacagtg gaggtacagt acgcagggac
1981 agatggacct tgcaaggttc cagctcagat ggcggtggac atgcaaactc tgaccccagt
2041 tgggaggttg ataaccgcta accccgtaat cactgaaagc actgagaact ctaagatgat
2101 gctggaactt gatccaccat ttggggactc ttacattgtc ataggagtcg gggagaagaa
2161 gatcacccac cactggcaca ggagtggcag caccattgga aaagcatttg aagccactgt
2221 gagaggtgcc aagagaatgg cagtcttggg agacacagcc tgggactttg gatcagttgg
2281 aggcgctctc aactcattgg gcaagggcat ccatcaaatt tttggagcag ctttcaaatc
2341 attgtttgga ggaatgtcct ggttctcaca aattctcatt ggaacgttgc tgatgtggtt
2401 gggtctgaac acaaagaatg gatctatttc ccttatgtgc ttggccttag gggagtgtt
2461 gatcttctta tccacagccg tctctgctga tgtggggtgc tcggtggact tctcaaagaa
2521 ggagacgaga tgcggtacag gggtgttcgt ctataacgac gttgaagcct ggaggacag
2581 gtacaagtac catcctgact ccccccgtag attggcagca gcagtcaagc aagcctggga
2641 agatggtatc tgcgggatct cctctgtttc aagaatggaa aacatcatgt ggagatcagt
2701 agaagggag ctcaacgcaa tcctggaaga gaatggagtt caactgacgg tcgttgtggg
2761 atctgtaaaa aaccccatgt ggagaggtcc acagagattg cccgtgcctg tgaacgagct
2821 gccccacggc tggaaggctt gggggaaatc gtatttcgtc agagcagcaa agacaaataa
2881 cagctttgtc gtggatggtg acacactgaa ggaatgccca ctcaaacata gagcatgaa
2941 cagctttctt gtggaggatc atgggttcgg ggtatttcac actagtgtct ggctcaaggt
```

-continued

```
3001 tagagaagat tattcattag agtgtgatcc agccgttatt ggaacagctg ttaagggaaa
3061 ggaggctgta cacagtgatc taggctactg gattgagagt gagaagaatg acacatggag
3121 gctgaagagg gcccatctga tcgagatgaa acatgtgaa tggccaaagt cccacacatt
3181 gtggacagat ggaatagaag agagtgatct gatcatacc aagtctttag ctgggccact
3241 cagccatcac aataccagag agggctacag gacccaaatg aaagggccat ggcacagtga
3301 agagcttgaa attcggtttg aggaatgccc aggcactaag gtccacgtgg aggaaacatg
3361 tggaacaaga ggaccatctc tgagatcaac cactgcaagc ggaagggtga tcgaggaatg
3421 gtgctgcagg gagtgcacaa tgcccccact gtcgttccgg gctaaagatg gctgttggta
3481 tggaatggag ataaggccca ggaaagaacc agaaagcaac ttagtaaggt caatggtgac
3541 tgcaggatca actgatcaca tggaccactt ctcccttgga gtgcttgtga tcctgctcat
3601 ggtgcaggaa gggctgaaga agagaatgac cacaaagatc atcataagca catcaatggc
3661 agtgctggta gctatgatcc tgggaggatt ttcaatgagt gacctggcta agcttgcaat
3721 tttgatgggt gccaccttcg cggaaatgaa cactggagga gatgtagctc atctggcgct
3781 gatagcggca ttcaaagtca gaccagcgtt gctggtatct ttcatcttca gagctaattg
3841 gacacccgt gaaagcatgc tgctggcctt ggcctcgtgt cttttgcaaa ctgcgatctc
3901 cgccttggaa ggcgacctga tggttctcat caatggtttt gctttggcct ggttggcaat
3961 acgagcgatg gttgttccac gcactgataa catcaccttg gcaatcctgg ctgctctgac
4021 accactggcc cggggcacac tgcttgtggc gtggagagca ggccttgcta cttgcggggg
4081 gtttatgctc ctctctctga agggaaaagg cagtgtgaag aagaacttac catttgtcat
4141 ggccctggga ctaaccgctg tgaggctggt cgaccccatc aacgtggtgg gactgctgtt
4201 gctcacaagg agtgggaagc ggagctggcc ccctagcgaa gtactcacag ctgttggcct
4261 gatatgcgca ttggctggag ggttcgccaa ggcagatata gagatggctg ggcccatggc
4321 cgcggtcggt ctgctaattg tcagttacgt ggtctcagga aagagtgtgg acatgtacat
4381 tgaaagagca ggtgacatca catgggaaaa agatgcggaa gtcactggaa acagtccccg
4441 gctcgatgtg gcgctagatg agagtggtga tttctccctg gtggaggatg acggtccccc
4501 catgagagag atcatactca aggtggtcct gatgaccatc tgtggcatga cccaatagc
4561 catacccttt gcagctggag cgtggtacgt atacgtgaag actggaaaaa ggagtggtgc
4621 tctatgggat gtgcctgctc ccaaggaagt aaaaaagggg gagaccacag atggagtgta
4681 cagagtaatg actcgtagac tgctaggttc aacacaagtt ggagtgggag ttatgcaaga
4741 gggggtcttt cacactatgt ggcacgtcac aaaaggatcc gcgctgagaa gcggtgaagg
4801 gagacttgat ccatactggg gagatgtcaa gcaggatctg gtgtcatact gtggtccatg
4861 gaagctagat gccgcctggg atgggcacag cgaggtgcag ctcttggccg tgccccccgg
4921 agagagagcg aggaacatcc agactctgcc cggaatattt aagacaaagg atggggacat
4981 tggagcggtt gcgctggatt acccagcagg aacttcagga tctccaatcc tagacaagtg
5041 tgggagagtg ataggacttt atggcaatgg ggtcgtgatc aaaaacggga gttatgttag
5101 tgccatcacc caagggagga gggaggaaga gactcctgtt gagtgcttcg agccctcgat
5161 gctgaagaag aagcagctaa ctgtcttaga cttgcatcct ggagctggga aaaccaggag
5221 agttcttcct gaaatagtcc gtgaagccat aaaaacaaga ctccgtactg tgatcttagc
5281 tccaaccagg gttgtcgctg ctgaaatgga ggaggccctt agagggcttc cagtgcgtta
5341 tatgacaaca gcagtcaatg tcacccactc tggaacagaa atcgtcgact aatgtgcca
5401 tgccaccttc acttcacgtc tactacagcc aatcagagtc cccaactata atctgtatat
```

-continued

```
5461  tatggatgag gcccacttca cagatccctc aagtatagca gcaagaggat acatttcaac
5521  aagggttgag atgggcgagg cggctgccat cttcatgacc gccacgccac caggaacccg
5581  tgacgcattt ccggactcca actcaccaat tatggacacc gaagtggaag tcccagagag
5641  agcctggagc tcaggctttg attgggtgac ggatcattct ggaaaaacag tttggtttgt
5701  tccaagcgtg aggaacggca atgagatcgc agcttgtctg acaaaggctg aaaacgggt
5761  catacagctc agcagaaaga cttttgagac agagttccag aaaacaaaac atcaagagtg
5821  ggactttgtc gtgacaactg acatttcaga gatgggcgcc aactttaaag ctgaccgtgt
5881  catagattcc aggagatgcc taaagccggt catacttgat ggcgagagag tcattctggc
5941  tggacccatg cctgtcacac atgccagcgc tgcccagagg agggggcgca taggcaggaa
6001  tcccaacaaa cctggagatg agtatctgta tggaggtggg tgcgcagaga ctgacgaaga
6061  ccatgcacac tggcttgaag caagaatgct ccttgacaat atttacctcc aagatggcct
6121  catagcctcg ctctatcgac ctgaggccga caaagtagca gccattgagg gagagttcaa
6181  gcttaggacg gagcaaagga agacctttgt ggaactcatg aaaagaggag atcttcctgt
6241  ttggctggcc tatcaggttg catctgccgg aataacctac acagatagaa gatggtgctt
6301  tgatggcacg accaacaaca ccataatgga agacagtgtg ccggcagagg tgtggaccag
6361  acacggagag aaaagagtgc tcaaaccgag gtggatggac gccagagttt gttcagatca
6421  tgcggccctg aagtcattca aggagtttgc cgctgggaaa agaggagcgg cttttggagt
6481  gatggaagcc ctgggaacac tgccaggaca catgacagag agattccagg aagccattga
6541  caacctcgct gtgctcatgc gggcagagac tggaagcagg ccttacaaag ccgcggcggc
6601  ccaattgccg gagaccctag agaccataat gcttttgggg ttgctgggaa cagtctcgct
6661  gggaatcttc ttcgtcttga tgaggaacaa gggcataggg aagatgggct ttggaatggt
6721  gactcttggg ccagcgcat ggctcatgtg gctctcggaa attgagccag ccagaattgc
6781  atgtgtcctc attgttgtgt tcctattgct ggtggtgctc atacctgagc cagaaaagca
6841  aagatctccc caggacaacc aaatggcaat catcatcatg gtagcagtag gtcttctggg
6901  cttgattacc gccaatgaac tcggatggtt ggagagaaca aagagtgacc taagccatct
6961  aatgggaagg agagaggagg gggcaaccat aggattctca atggacattg acctgcggcc
7021  agcctcagct tgggccatct atgctgcctt gacaactttc attaccccag ccgtccaaca
7081  tgcagtgacc acctcataca acaactactc cttaatggcg atggccacgc aagctggagt
7141  gttgtttggc atgggcaaag gatgccatt ctacgcatgg gactttggag tcccgctgct
7201  aatgataggt tgctactcac aattaacacc cctgacccta atagtggcca tcattttgct
7261  cgtggcgcac tacatgtact tgatcccagg gctgcaggca gcagctgcgc gtgctgccca
7321  gaagagaacg gcagctggca tcatgaagaa ccctgttgtg gatggaatag tggtgactga
7381  cattgacaca atgacaattg accccaagt ggagaaaaag atgggacagg tgctactcat
7441  agcagtagcc gtctccagcg ccatactgtc gcggaccgcc tgggggtggg gggaggctgg
7501  ggctctgatc acagccgcaa cttccacttt gtgggaaggc tctccgaaca agtactggaa
7561  ctcctctaca gccacttcac tgtgtaacat ttttagggga agttacttgg ctggagcttc
7621  tctaatctac acagtaacaa gaaacgctgg cttggtcaag agacgtgggg gtggaacagg
7681  agagaccctg ggagagaaat ggaaggcccg cttgaaccag atgtcggccc tggagttcta
7741  ctcctacaaa aagtcaggca tcaccgaggt gtgcagagaa gaggcccgcc gcgccctcaa
7801  ggacggtgtg gcaacgggag gccatgctgt gtcccgagga agtgcaaagc tgagatggtt
```

-continued

```
 7861 ggtggagcgg ggatacctgc agccctatgg aaaggtcatt gatcttggat gtggcagagg
 7921 gggctggagt tactacgtcg ccaccatccg caaagttcaa gaagtgaaag gatacacaaa
 7981 aggaggccct ggtcatgaag aacccgtgtt ggtgcaaagc tatgggtgga acatagtccg
 8041 tcttaagagt ggggtggacg tctttcatat ggcggctgag ccgtgtgaca cgttgctgtg
 8101 tgacataggt gagtcatcat ctagtcctga agtggaagaa gcacggacgc tcagagtcct
 8161 ctccatggtg ggggattggc ttgaaaaaag accaggagcc ttttgtataa aagtgttgtg
 8221 cccatacacc agcactatga tggaaaccct ggagcgactg cagcgtaggt atggggagg
 8281 actggtcaga gtgccactct cccgcaactc tacacatgag atgtactggg tctctggagc
 8341 gaaaagcaac accataaaaa gtgtgtccac cacgagccag ctcctcttgg ggcgcatgga
 8401 cgggcctagg aggccagtga aatatgagga ggatgtgaat ctcggctctg gcacgcgggc
 8461 tgtggtaagc tgcgctgaag ctcccaacat gaagatcatt ggtaaccgca ttgaaaggat
 8521 ccgcagtgag cacgcggaaa cgtggttctt tgacgagaac cacccatata ggacatgggc
 8581 ttaccatgga agctatgagg cccccacaca agggtcagcg tcctctctaa taaacggggt
 8641 tgtcaggctc ctgtcaaaac cctgggatgt ggtgactgga gtcacaggaa tagccatgac
 8701 cgacaccaca ccgtatggtc agcaaagagt tttcaaggaa aagtggaca ctagggtgcc
 8761 agacccccaa gaaggcactc gtcaggttat gagcatggtc tcttcctggt tgtggaaaga
 8821 gctaggcaaa cacaaacggc cacgagtctg caccaaagaa gagttcatca acaaggttcg
 8881 tagcaatgca gcattagggg caatatttga gaggaaaaa gagtggaaga ctgcagtgga
 8941 agctgtgaac gatccaaggt tctgggctct agtggacaag aaagagagc accacctgag
 9001 aggagagtgc cagagctgtg tgtacaacat gatgggaaaa agagaaaaga acaagggga
 9061 atttggaaag gccaagggca gccgcgccat ctggtatatg tggctagggg ctagatttct
 9121 agagttcgaa gcccttggat tcttgaacga ggatcactgg atggggagag agaactcagg
 9181 aggtggtgtt gaagggctgg gattacaaag actcggatat gtcctagaag agatgagtcg
 9241 tataccagga ggaaggatgt atgcagatga cactgctggc tgggacaccc gcattagcag
 9301 gtttgatctg gagaatgaag ctctaatcac caaccaaatg gagaaaggc acagggcctt
 9361 ggcattggcc ataatcaagt acacatacca aaacaaagtg gtaaaggtcc ttagaccagc
 9421 tgaaaaaggg aaaacagtta tggacattat ttcgagacaa gaccaaaggg ggagcggaca
 9481 agttgtcact tacgctctta acacatttac caacctagtg gtgcaactca ttcggaatat
 9541 ggaggctgag gaagttctag agatgcaaga cttgtggctg ctgcggaggt cagagaaagt
 9601 gaccaactgg ttgcagagca acggatggga taggctcaaa cgaatggcag tcagtggaga
 9661 tgattgcgtt gtgaagccaa ttgatgatag gtttgcacat gccctcaggt tcttgaatga
 9721 tatgggaaaa gttaggaagg acacacaaga gtggaaaccc tcaactggat gggacaactg
 9781 ggaagaagtt ccgttttgct cccaccactt caacaagctc atctcaagg acgggaggtc
 9841 cattgtggtt ccctgccgcc accaagatga actgattggc cgggcccgcg tctctccagg
 9901 ggcgggatgg agcatccggg agactgcttg cctagcaaaa tcatatgcgc aaatgtggca
 9961 gctccttat ttccacagaa gggacctccg actgatggcc aatgccattt gttcatctgt
10021 gccagttgac tgggttccaa ctgggagaac tacctggtca atccatggaa agggagaatg
10081 gatgaccact gaagacatgc ttgtggtgtg aacagagtg tggattgagg agaacgacca
10141 catggaagac aagaccccag ttacgaaatg gacagacatt ccctatttgg gaaaagggga
10201 agacttgtgg tgtggatctc tcatagggca cagaccgcgc accacctggg ctgagaacat
10261 taaaaacaca gtcaacatgg tgcgcaggat cataggtgat gaagaaaagt acatggacta
```

```
10321  cctatccacc caagttcgct acttgggtga agaagggtct acacctggag tgctgtaagc 10381  accaatctta atgttgtcag gcctgctagt cagccacagc ttggggaaag ctgtgcagcc 10441  tgtgaccccc ccaggagaag ctgggaaacc aagcctatag tcaggccgag aacgccatgg 10501  cacggaagaa gccatgctgc ctgtgagccc ctcagaggac actgagtcaa aaaaccccac 10561  gcgcttggag gcgcaggatg ggaaaagaag gtggcgacct tccccaccct tcaatctggg 10621  gcctgaactg gagatcagct gtggatctcc agaagaggga ctagtggtta gagga
```

In some embodiments, the Zika virus may comprise the genome sequence of GenBank Accession number KU501215.1. In some embodiments, the Zika virus is from strain PRVABC59. In some embodiments the genome sequence of GenBank Accession number KU501215.1 comprises the sequence of SEQ ID NO: 2. In some embodiments, the Zika virus may comprise a genomic sequence that has at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity with the sequence of SEQ ID NO: 2.

In some embodiments, the Zika virus may comprise at least one polypeptide encoded by the sequence of SEQ ID NO: 2. In some embodiments, the Zika virus may comprise at least one polypeptide having an amino acid sequence that has at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity with an amino acid sequence encoded by the sequence of SEQ ID NO: 2.

Accordingly, in some embodiments, inactivated Zika viruses of the present disclosure may be used in any of the vaccines and/or immunogenic compositions disclosed herein. For example, inactivated Zika viruses of the present disclosure may be used to provide one or more antigens useful for treating or preventing Zika virus infection in a subject in need thereof and/or for inducing an immune response, such as a protective immune response, against Zika virus in a subject in need thereof.

The Zika virus used in the present disclosure may be obtained from one or more cells in cell culture (e.g., via plaque purification). Any suitable cells known in the art for producing Zika virus may be used, including, for example, insect cells (e.g., mosquito cells such as CCL-125 cells, Aag-2 cells, RML-12 cells, C6/36 cells, C7-10 cells, AP-61 cells, A.t. GRIP-1 cells, A.t. GRIP-2 cells, A.t. GRIP-3 cells, UM-AVE1 cells, Mos.55 cells, Sua1B cells, 4a-3B cells, Mos.42 cells, MSQ43 cells, LSB-AA695BB cells, NIID-CTR cells, TRA-171, cells, and additional cells or cell lines from mosquito species such as *Aedes aegypti, Aedes albopictus, Aedes pseudoscutellaris, Aedes triseriatus, Aedes vexans, Anopheles gambiae, Anopheles stephensi, Anopheles albimus, Culex quinquefasciatus, Culex theileri, Culex tritaeniorhynchus, Culex bitaeniorhynchus,* and/or *Toxorhynchites amboinensis*), and mammalian cells (e.g., VERO cells (from monkey kidneys), LLC-MK2 cells (from monkey kidneys), MDBK cells, MDCK cells, ATCC CCL34 MDCK (NBL2) cells, MDCK 33016 (deposit number DSM ACC 2219 as described in WO97/37001) cells, BHK21-F cells, HKCC cells, or Chinese hamster ovary cells (CHO cells). In some embodiments, the Zika virus (e.g., a Zika virus clonal isolate) is produced from a non-human cell. In some embodiments, the Zika virus (e.g., a Zika virus clonal isolate) is produced from an insect cell. In some embodiments, the Zika virus (e.g., a Zika virus clonal isolate) is produced from a mosquito cell. In some embodiments, the Zika virus (e.g., a Zika virus clonal isolate) is produced from a mammalian cell. In some embodiments, the Zika virus (e.g., a Zika virus clonal isolate) is produced from a VERO cell.

Zika viruses possess a positive sense, single-stranded RNA genome encoding both structural and nonstructural polypeptides. The genome also contains non-coding sequences at both the 5'- and 3'-terminal regions that play a role in virus replication. Structural polypeptides encoded by these viruses include, without limitation, capsid (C), precursor membrane (prM), and envelope (E). Non-structural (NS) polypeptides encoded by these viruses include, without limitation, NS1, NS2A, NS2B, NS3, NS4A, NS4B, and NS5.

In certain embodiments, the Zika virus includes a mutation in Zika virus Non-structural protein 1 (NS1). In some embodiments, the Zika virus contains a Trp98Gly mutation at position 98 of SEQ ID NO: 1, or at a position corresponding to position 98 of SEQ ID NO: 1.

In some embodiments, the mutation is within the NS1 polypeptide. The amino acid sequence of a wild-type, NS1 polypeptide from an exemplary Zika virus strain is set forth as:

(SEQ ID NO: 1)
DVGCSVDFSKKETRCGTGVFVYNDVEAWRDRYKYHPDSPRRLAAAVKQAW

EDGICGISSVSRMENIMWRSVEGELNAILEENGVQLTVVVGSVKNPMWRG

PQRLPVPVNELPHGWKAWGKSYFVRAAKTNNSFVVDGDTLKECPLKHRAW

NSFLVEDHGFGVFHTSVWLKVREDYSLECDPAVIGTAVKGKEAVHSDLGY

WIESEKNDTWRLKRAHLIEMKTCEWPKSHTLWTDGIEESDLIIPKSLAGP

LSHHNTREGYRTQMKGPWHSEELEIRFEECPGTKVHVEETCGTRGPSLRS

TTASGRVIEEWCCRECTMPPLSFRAKDGCWYGMEIRPRKEPESNLVRSMV

T.

In some embodiments, the amino acid sequence of the NS1 polypeptide has at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity with the sequence of SEQ ID NO: 1. In some embodiments, the amino acid sequence of the NS1 polypeptide may be from the amino acid sequence encoded by the sequence of GenBank Accession number KU501215.1 (SEQ ID NO: 2). In some embodiments, the amino acid sequence of the NS1 polypeptide may be amino acid positions 795 to 1145 of the amino acid sequence encoded by the sequence of GenBank Accession number KU501215.1. In some embodiments, the amino acid sequence of the NS1 polypeptide may be from Zika virus strain PRVABC59.

"Sequence Identity", "% sequence identity", "% identity", "% identical" or "sequence alignment" means a comparison of a first amino acid sequence to a second amino acid sequence, or a comparison of a first nucleic acid sequence to a second nucleic acid sequence and is calculated as a percentage based on the comparison. The result of this calculation can be described as "percent identical" or "percent ID."

Generally, a sequence alignment can be used to calculate the sequence identity by one of two different approaches. In the first approach, both mismatches at a single position and gaps at a single position are counted as non-identical positions in final sequence identity calculation. In the second approach, mismatches at a single position are counted as non-identical positions in final sequence identity calculation; however, gaps at a single position are not counted (ignored) as non-identical positions in final sequence identity calculation. In other words, in the second approach gaps are ignored in final sequence identity calculation. The difference between these two approaches, i.e. counting gaps as non-identical positions vs ignoring gaps, at a single position can lead to variability in the sequence identity value between two sequences.

In some embodiments, a sequence identity is determined by a program, which produces an alignment, and calculates identity counting both mismatches at a single position and gaps at a single position as non-identical positions in final sequence identity calculation. For example program Needle (EMBOS), which has implemented the algorithm of Needleman and Wunsch (Needleman and Wunsch, 1970, J. Mol. Biol. 48: 443-453), and which calculates sequence identity per default settings by first producing an alignment between a first sequence and a second sequence, then counting the number of identical positions over the length of the alignment, then dividing the number of identical residues by the length of an alignment, then multiplying this number by 100 to generate the % sequence identity [% sequence identity=(# of Identical residues/length of alignment)×100)].

A sequence identity can be calculated from a pairwise alignment showing both sequences over the full length, so showing the first sequence and the second sequence in their full length ("Global sequence identity"). For example, program Needle (EMBOSS) produces such alignments; % sequence identity=(# of identical residues/length of alignment)×100)].

A sequence identity can be calculated from a pairwise alignment showing only a local region of the first sequence or the second sequence ("Local Identity"). For example, program Blast (NCBI) produces such alignments; % sequence identity=(# of Identical residues/length of alignment)×100)].

The sequence alignment is preferably generated by using the algorithm of Needleman and Wunsch (J. Mol. Biol. (1979) 48, p. 443-453). Preferably, the program "NEEDLE" (The European Molecular Biology Open Software Suite (EMBOSS)) is used with the programs default parameter (gap open=10.0, gap extend=0.5 and matrix=EBLOSUM62 for proteins and matrix=EDNAFULL for nucleotides). Then, a sequence identity can be calculated from the alignment showing both sequences over the full length, so showing the first sequence and the second sequence in their full length ("Global sequence identity"). For example: % sequence identity=(# of identical residues/length of alignment)×100)].

In some embodiments, the mutation occurs at one or more amino acid positions within the NS1 polypeptide. In some embodiments, the mutation occurs at position 98 of SEQ ID NO: 1, or at a position corresponding to position 98 of SEQ ID NO: 1 when aligned to SEQ ID NO: 1 using a pairwise alignment algorithm. In some embodiments, the mutation at position 98 is a tryptophan to glycine substitution.

Figure 7:
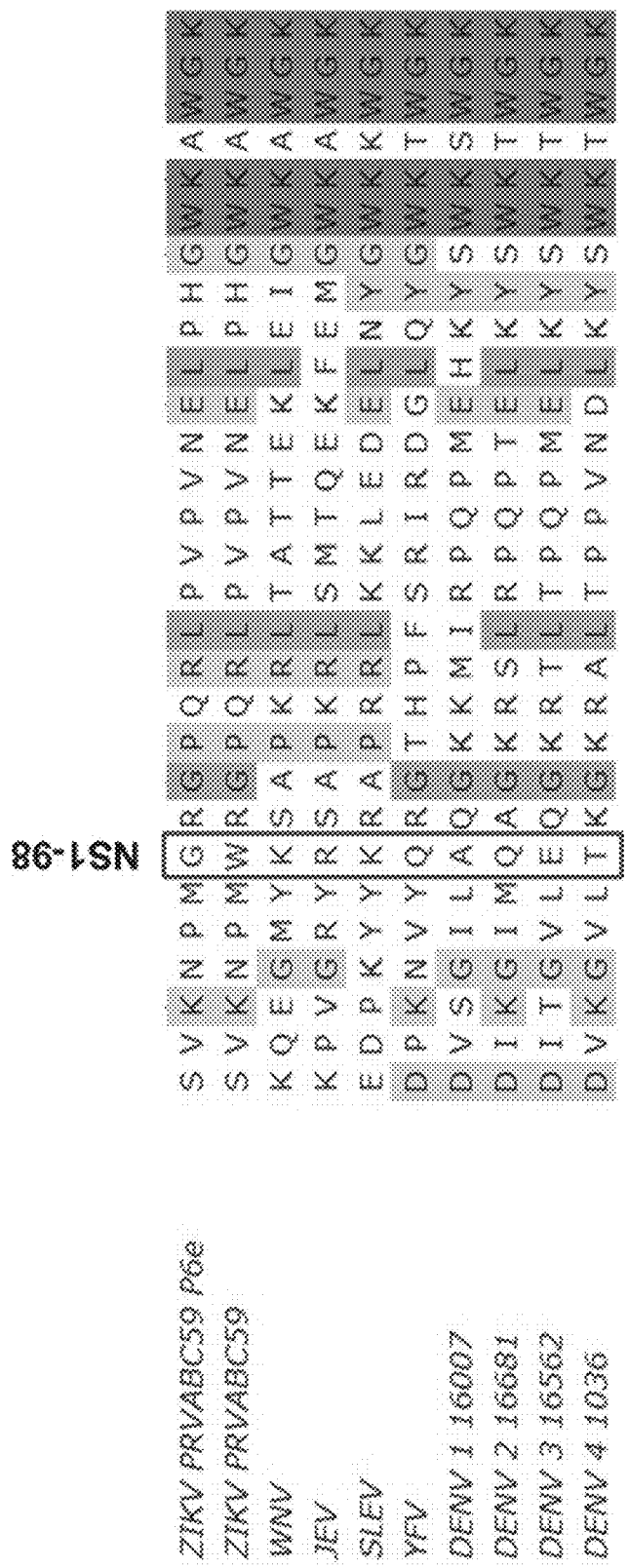
FIG. 7 shows an amino acid sequence alignment comparing the NS1 protein sequence of Zika virus near residue 98 from Zika virus strains PRVABC59 P6e (SEQ ID NO: 18) and PRVABC59 (SEQ ID NO: 19) with several other flaviviruses (WNV (SEQ ID NO: 20); JEV (SEQ ID NO: 21); SLEV (SEQ ID NO: 22); YFV (SEQ ID NO: 23); DENV 1 16007 (SEQ ID NO: 24); DENV 2 16681 (SEQ ID NO: 25); DENV 3 16562 (SEQ IDNO: 26); and DENV 4 1036 (SEQ ID NO: 27)).

In some embodiments, the Zika virus comprises a mutation at position 98 of SEQ ID NO: 1, or at a position corresponding to position 98 of SEQ ID NO: 1. A position corresponding to position 98 of SEQ ID NO: 1 can be determined by aligning the amino acid sequence of an NS-1 protein to SEQ ID NO: 1 using a pairwise alignment algorithm Amino acid residues in viruses other than Zika virus which correspond to the tryptophan residue at position 98 of SEQ ID NO: 1 are shown in FIG. 7 of the present application where these residues are boxed. In some embodiments, the mutation at position 98 is a tryptophan to glycine substitution. In some embodiments, the mutation at position 98 is a tryptophan to glycine substitution at position 98 of SEQ ID NO: 1.

In some embodiments, the Zika virus contains a mutation within the NS1 protein, and at least one mutation within one or more of the C, prM, E, NS1, NS2A, NS2B, NS3, NS4A, NS4B, and NS5 viral proteins. In some embodiments, the Zika virus contains one or more mutations within the NS1 protein, and does not contain at least one mutation within one or more of the C, prM, E, NS1, NS2A, NS2B, NS3, NS4A, NS4B, and NS5 viral proteins. In some embodiments, the Zika virus contains a mutation within the NS1 protein and does not contain at least one mutation within the envelope protein E. In some embodiments, whole, inactivated virus contains at least one mutation in Zika virus Non-structural protein 1 (NS1), and does not include a mutation in Zika virus envelope protein E (Env). In some embodiments, the Zika virus contains a mutation at position 98 of SEQ ID NO: 1, or at a position corresponding to position 98 of SEQ ID NO: 1 and does not contain any mutation within the envelope protein E. In some embodiments, whole, inactivated Zika virus contains a mutation at position 98 of SEQ ID NO: 1, or at a position corresponding to position 98 of SEQ ID NO: 1 and does not include a mutation in Zika virus envelope protein E (Env). In some embodiments, whole, inactivated virus contains at least one mutation in Zika virus Non-structural protein 1 (NS1) and the sequence encoding the envelope protein is the same as the corresponding sequence in SEQ ID No. 2. In some embodiments, the Zika virus contains a mutation at position 98 of SEQ ID NO: 1, or at a position corresponding to position 98 of SEQ ID NO: 1 and the sequence encoding the envelope protein is the same as the corresponding sequence in SEQ ID NO. 2. In some embodiments, whole, inactivated Zika virus contains a mutation at position 98 of SEQ ID NO: 1, or at a position corresponding to position 98 of SEQ ID NO: 1 and the sequence encoding the envelope protein is the same as the corresponding sequence in SEQ ID NO: 2.

In some embodiments, the Zika virus contains at least one mutation that enhances genetic stability as compared to a Zika virus lacking the at least one mutation. In some embodiments, the Zika virus contains at least one mutation that enhances viral replication as compared to a Zika virus lacking the at least one mutation. In some embodiments, the Zika virus contains at least one mutation that reduces or otherwise inhibits the occurrence of undesirable mutations, such as within the envelope protein E (Env) of the Zika virus.

In the above embodiments of the present disclosure, an exemplary pairwise alignment algorithm is the Needleman-Wunsch global alignment algorithm, using default parameters (e.g. with Gap opening penalty=10.0, and with Gap extension penalty=0.5, using the EBLOSUM62 scoring matrix). This algorithm is conveniently implemented in the needle tool in the EMBOSS package.

In some embodiments, the inactivated Zika virus may be used in vaccines and immunogenic compositions. For example, the inactivated Zika virus may be useful for treating or preventing Zika virus infection in a subject in need thereof and/or inducing an immune response, such as a protective immune response, against Zika virus in a subject in need thereof.

Production of Vaccines and Immunogenic Compositions

Other aspects of the present disclosure relate to Zika virus vaccines and immunogenic compositions containing a purified inactivated whole virus, such as a Zika virus with a mutation which is a tryptophan to glycine substitution at position 98 of SEQ ID NO: 1 or at a position corresponding to position 98 of SEQ ID NO: 1 as described herein. In some embodiments, the vaccine or immunogenic composition comprises a purified inactivated whole Zika virus comprising a Trp98Gly mutation at position 98 of SEQ ID NO: 1, or at a position corresponding to position 98 of SEQ ID NO: 1, wherein the Zika virus is derived from strain PRVABC59. In some embodiments, the vaccine or immunogenic composition comprises a purified inactivated whole Zika virus comprising a Trp98Gly mutation at position 98 of SEQ ID NO: 1, or at a position corresponding to position 98 of SEQ ID NO: 1, wherein the Zika virus is derived from strain PRVABC59 comprising the genomic sequence according to SEQ ID NO: 2. In one embodiment, the vaccines and immunogenic compositions contain a plaque purified clonal Zika virus isolate. Such vaccines and immunogenic compositions may be useful, for example, for treating or preventing Zika virus infection in a subject in need thereof and/or inducing an immune response, such as a protective immune response, against Zika virus in a subject in need thereof.

Production of vaccines and/or immunogenic compositions of the present disclosure includes growth of Zika virus. Growth in cell culture is a method for preparing vaccines and/or immunogenic compositions of the present disclosure. Cells for viral growth may be cultured in suspension or in adherent conditions.

Cell lines suitable for growth of the at least one virus of the present disclosure are preferably of mammalian origin, and include, but are not limited to: insect cells (e.g., mosquito cells as described herein, VERO cells (from monkey kidneys), horse, cow (e.g. MDBK cells), sheep, dog (e.g. MDCK cells from dog kidneys, ATCC CCL34 MDCK (NBL2) or MDCK 33016, deposit number DSM ACC 2219 as described in WO97/37001), cat, and rodent (e.g. hamster cells such as BHK21-F, HKCC cells, or Chinese hamster ovary cells (CHO cells)), and may be obtained from a wide variety of developmental stages, including for example, adult, neonatal, fetal, and embryo. In certain embodiments, the cells are immortalized (e.g. PERC.6 cells, as described in WO 01/38362 and WO 02/40665, and as deposited under ECACC deposit number 96022940). In preferred embodiments, mammalian cells are utilized, and may be selected from and/or derived from one or more of the following non-limiting cell types: fibroblast cells (e.g. dermal, lung), endothelial cells (e.g. aortic, coronary, pulmonary, vascular, dermal microvascular, umbilical), hepatocytes, keratinocytes, immune cells (e.g. T cell, B cell, macrophage, NK, dendritic), mammary cells (e.g. epithelial), smooth muscle cells (e.g. vascular, aortic, coronary, arterial, uterine, bronchial, cervical, retinal pericytes), melanocytes, neural cells (e.g. astrocytes), prostate cells (e.g. epithelial, smooth muscle), renal cells (e.g. epithelial, mesangial, proximal tubule), skeletal cells (e.g. chondrocyte, osteoclast, osteoblast), muscle cells (e.g. myoblast, skeletal, smooth, bronchial), liver cells, retinoblasts, and stromal cells. WO 97/37000 and WO 97/37001 describe production of animal cells and cell lines that are capable of growth in suspension and in serum free media and are useful in the production and replication of viruses.

Culture conditions for the above cell types are known and described in a variety of publications. Alternatively culture medium, supplements, and conditions may be purchased commercially, such as for example, described in the catalog and additional literature of Cambrex Bioproducts (East Rutherford, N.J.).

In certain embodiments, the cells used in the methods described herein are cultured in serum free and/or protein free media. A medium is referred to as a serum-free medium in the context of the present disclosure, if it does not contain any additives from serum of human or animal origin. Protein-free is understood to mean cultures in which multiplication of the cells occurs with exclusion of proteins, growth factors, other protein additives and non-serum proteins, but can optionally include proteins such as trypsin or other proteases that may be necessary for viral growth. The cells growing in such cultures naturally contain proteins themselves.

Known serum-free media include Iscove's medium, Ultra-CHO medium (BioWhittaker) or EX-CELL (JRH Bioscience). Ordinary serum-containing media include Eagle's Basal Medium (BME) or Minimum Essential Medium (MEM) (Eagle, Science, 130, 432 (1959)) or Dulbecco's Modified Eagle Medium (DMEM or EDM), which are ordinarily used with up to 10% fetal calf serum or similar additives. Optionally, Minimum Essential Medium (MEM) (Eagle, Science, 130, 432 (1959)) or Dulbecco's Modified Eagle Medium (DMEM or EDM) may be used without any serum containing supplement. Protein-free media like PF-CHO (JHR Bioscience), chemically-defined media like ProCHO 4CDM (BioWhittaker) or SMIF 7 (Gibco/BRL Life Technologies) and mitogenic peptides like Primactone, Pepticase or HyPep™ (all from Quest International) or lactalbumin hydrolysate (Gibco and other manufacturers) are also adequately known in the prior art. The media additives based on plant hydrolysates have the special advantage that contamination with viruses, mycoplasma or unknown infectious agents can be ruled out.

Cell culture conditions (temperature, cell density, pH value, etc.) are variable over a very wide range owing to the suitability of the cell line employed according to the present disclosure and can be adapted to the requirements of particular viral strains.

The method for propagating virus in cultured cells generally includes the steps of inoculating the cultured cells with the strain to be cultured, cultivating the infected cells for a desired time period for virus propagation, such as for example as determined by virus titer or antigen expression (e.g. between 24 and 168 hours after inoculation) and collecting the propagated virus. In some embodiments, the virus is collected via plaque purification. The cultured cells are inoculated with a virus (measured by PFU or TCID50)

to cell ratio of 1:500 to 1:1, preferably 1:100 to 1:5. The virus is added to a suspension of the cells or is applied to a monolayer of the cells, and the virus is absorbed on the cells for at least 10 minutes, at least 20 minutes, at least 30 minutes, at least 40 minutes, at least 50 minutes, at least 60 minutes but usually less than 300 minutes at 25° C. to 40° C., preferably 28° C. to 38° C. The infected cell culture (e.g. monolayers) may be removed either by harvesting the supernatant (free of cells), freeze-thawing or by enzymatic action to increase the viral content of the harvested culture supernatants. The harvested fluids are then either inactivated or stored frozen. Cultured cells may be infected at a multiplicity of infection ("MOI") of about 0.0001 to 10, preferably 0.002 to 5, more preferably to 0.001 to 2. Still more preferably, the cells are infected at an MOI of about 0.01. During infection the ratio of culture medium to the area of the cell culture vessel may be lower than during the culture of the cells. Keeping this ratio low maximizes the likelihood that the virus will infect the cells. The supernatant of the infected cells may be harvested from 30 to 60 hours post infection, or 3 to 10 days post infection. In certain preferred embodiments, the supernatant of the infected cells is harvested 3 to 7 days post infection. More preferably, the supernatant of the infected cells is harvested 3 to 5 days post infection. In some embodiments, proteases (e.g., trypsin) may be added during cell culture to allow viral release, and the proteases may be added at any suitable stage during the culture. Alternatively, in certain embodiments, the supernatant of infected cell cultures may be harvested and the virus may be isolated or otherwise purified from the supernatant.

The viral inoculum and the viral culture are preferably free from (i.e. will have been tested for and given a negative result for contamination by) herpes simplex virus, respiratory syncytial virus, parainfluenza virus 3, SARS coronavirus, adenovirus, rhinovirus, reoviruses, polyomaviruses, birnaviruses, circoviruses, and/or parvoviruses (WO 2006/027698).

Where virus has been grown on a cell line then it is standard practice to minimize the amount of residual cell line DNA in the final vaccine, in order to minimize any oncogenic activity of the host cell DNA. Contaminating DNA can be removed during vaccine preparation using standard purification procedures e.g. chromatography, etc. Removal of residual host cell DNA can be enhanced by nuclease treatment e.g. by using a DNase. A convenient method for reducing host cell DNA contamination disclosed in references (Lundblad (2001) Biotechnology and Applied Biochemistry 34:195-197, *Guidance for Industry: Bioanalytical Method Validation*. U.S. Department of Health and Human Services Food and Drug Administration Center for Drug Evaluation and Research (CDER) Center for Veterinary Medicine (CVM). May 2001) involves a two-step treatment, first using a DNase (e.g. Benzonase), which may be used during viral growth, and then a cationic detergent (e.g. CTAB), which may be used during virion disruption. Removal by β-propiolactone treatment can also be used. In one embodiment, the contaminating DNA is removed by benzonase treatment of the culture supernatant.

Production of Antigens

The Zika virus may be produced and/or purified or otherwise isolated by any suitable method known in the art. In one embodiment, the antigen of the present disclosure is a purified inactivated whole Zika virus.

In some embodiments, inactivated viruses, can be produced as described in the above section entitled "Production of Vaccines and Immunogenic Compositions."

In certain embodiments, the Zika virus of the present disclosure may be produced by culturing a non-human cell. Cell lines suitable for production of Zika virus of the present disclosure may include insect cells (e.g., any of the mosquito cells described herein). Cell lines suitable for production of Zika virus of the present disclosure may also be cells of mammalian origin, and include, but are not limited to: VERO cells (from monkey kidneys), horse, cow (e.g. MDBK cells), sheep, dog (e.g. MDCK cells from dog kidneys, ATCC CCL34 MDCK (NBL2) or MDCK 33016, deposit number DSM ACC 2219 as described in WO 97/37001), cat, and rodent (e.g. hamster cells such as BHK21-F, HKCC cells, or Chinese hamster ovary cells (CHO cells)), and may be obtained from a wide variety of developmental stages, including for example, adult, neonatal, fetal, and embryo. In certain embodiments, the cells are immortalized (e.g. PERC.6 cells, as described in WO 01/38362 and WO 02/40665, and as deposited under ECACC deposit number 96022940). In preferred embodiments, mammalian cells are utilized, and may be selected from and/or derived from one or more of the following non-limiting cell types: fibroblast cells (e.g. dermal, lung), endothelial cells (e.g. aortic, coronary, pulmonary, vascular, dermal microvascular, umbilical), hepatocytes, keratinocytes, immune cells (e.g. T cell, B cell, macrophage, NK, dendritic), mammary cells (e.g. epithelial), smooth muscle cells (e.g. vascular, aortic, coronary, arterial, uterine, bronchial, cervical, retinal pericytes), melanocytes, neural cells (e.g. astrocytes), prostate cells (e.g. epithelial, smooth muscle), renal cells (e.g. epithelial, mesangial, proximal tubule), skeletal cells (e.g. chondrocyte, osteoclast, osteoblast), muscle cells (e.g. myoblast, skeletal, smooth, bronchial), liver cells, retinoblasts, and stromal cells. WO 97/37000 and WO 97/37001 describe production of animal cells and cell lines that are capable of growth in suspension and in serum free media and are useful in the production of viral antigens. In certain embodiments, the non-human cell is cultured in serum-free media.

Virus Inactivation

Certain embodiments of the present disclosure relate to Zika virus vaccines and/or immunogenic compositions containing a purified inactivated Zika virus. The term "inactivated Zika virus" as used herein is intended to comprise a Zika virus which has been treated with an inactivating method such as treatment with an effective amount of formalin. In particular, the inactivated Zika virus is obtainable/obtained from a method wherein the Zika virus is treated with formaldehyde in an amount of about 0.01% w/v for 10 days at a temperature of 20° C. to 24° C. The inactivated Zika virus is no longer able to infect host cells which can be infected with a Zika virus which has not been inactivated. In one embodiment, the inactivated Zika virus is no longer able to infect VERO cells and to exert a cytopathic effect on the VERO cells.

The term "purified Zika virus" means that the Zika virus has been subjected to a purification process as described below. The purified Zika virus has a lower content of host cell proteins such as Vero cell proteins and host cell DNA such as Vero cell DNA than a non-purified Zika virus. The purity of the purified Zika virus can be determined by size exclusion chromatography. The main peak of the purified Zika virus in the size exclusion chromatography may be more than 85% of the total area under the curve in the size exclusion chromatography, or more than 90% of the total area under the curve in the size exclusion chromatography, or more than 95% of the total area under the curve in the size exclusion chromatography. Such results are considered as "purified" Zika virus.

The term "purified inactivated whole Zika virus" thus refers to a Zika virus obtainable/obtained from a method wherein the purified Zika virus is treated with formaldehyde in an amount of 0.01% w/v for 10 days at a temperature of 20° C. to 24° C. and provides a main peak of at least 85% of the total area under the curve in the size exclusion chromatography. In certain embodiments the purified inactivated whole Zika virus is a clonal isolate obtained/obtainable by plaque purification.

Methods of inactivating or killing viruses to destroy their ability to infect mammalian cells, but do not destroy the secondary, tertiary or quaternary structure and immunogenic epitopes of the virus are known in the art. Such methods include both chemical and physical means. Suitable means for inactivating a virus include, without limitation, treatment with an effective amount of one or more agents selected from detergents, formalin (also referred to herein as "formaldehyde"), hydrogen peroxide, beta-propiolactone (BPL), binary ethylamine (BEI), acetyl ethyleneimine, heat, electromagnetic radiation, x-ray radiation, gamma radiation, ultraviolet radiation (UV radiation), UV-A radiation, UV-B radiation, UV-C radiation, methylene blue, psoralen, carboxyfullerene (C60), hydrogen peroxide and any combination of any thereof. As already mentioned above, for the purpose of the present application the terms "formalin" and "formaldehyde" are used interchangeably.

In certain embodiments of the present disclosure the at least one virus is chemically inactivated. Agents for chemical inactivation and methods of chemical inactivation are well-known in the art and described herein. In some embodiments, the at least one virus is chemically inactivated with one or more of BPL, hydrogen peroxide, formalin, or BEI. In certain embodiments where the at least one virus is chemically inactivated with BPL, the virus may contain one or more modifications. In some embodiments, the one or more modifications may include a modified nucleic acid. In some embodiments, the modified nucleic acid is an alkylated nucleic acid. In other embodiments, the one or more modifications may include a modified polypeptide. In some embodiments, the modified polypeptide contains a modified amino acid residue including one or more of a modified cysteine, methionine, histidine, aspartic acid, glutamic acid, tyrosine, lysine, serine, and threonine.

In certain embodiments where the at least one virus is chemically inactivated with formalin, the inactivated virus may contain one or more modifications. In some embodiments, the one or more modifications may include a modified polypeptide. In some embodiments, the one or more modifications may include a cross-linked polypeptide. In some embodiments where the at least one virus is chemically inactivated with formalin, the vaccine or immunogenic composition further includes formalin. In certain embodiments where the at least one virus is chemically inactivated with BEI, the virus may contain one or more modifications. In some embodiments, the one or more modifications may include a modified nucleic acid. In some embodiments, the modified nucleic acid is an alkylated nucleic acid.

In some embodiments where the at least one virus is chemically inactivated with formalin, any residual unreacted formalin may be neutralized with sodium metabisulfite, may be dialyzed out, and/or may be buffer exchanged to remove the residual unreacted formalin. In some embodiments, the sodium metabisulfite is added in excess. In some embodiments, the solutions may be mixed using a mixer, such as an in-line static mixer, and subsequently filtered or further purified (e.g., using a cross flow filtrations system).

Certain embodiments of the present disclosure relate to a method for inactivating a Zika virus preparation. In some embodiments, the method involves (a) isolating the Zika virus preparation from one or more cells cultured in vitro that are used to produce the virus preparation and (b) treating the virus preparation with from about 0.005% to about 0.02% v/v formaldehyde.

In some embodiments, the cells are non-human cells. Suitable non-human mammalian cells include, but are not limited to, VERO cells, LLC-MK2 cells, MDBK cells, MDCK cells, ATCC CCL34 MDCK (NBL2) cells, MDCK 33016 (deposit number DSM ACC 2219 as described in WO97/37001) cells, BHK21-F cells, HKCC cells, and Chinese hamster ovary cells (CHO cells). In some embodiments, the mammalian cells are Vero cells.

In certain embodiments of the method, the Zika virus preparation is treated with formalin at a temperature that ranges from about 2° C. to about 42° C. For example, the Zika virus preparation may be treated with formalin at a temperature that ranges from about 2° C. to about 42° C., about 2° C. to about 8° C., about 15° C. to about 37° C., about 17° C. to about 27° C., about 20° C. to about 25° C., or at a temperature of about 2° C., about 4° C., about 8° C., about 10° C., about 15° C., about 17° C., about 18° C., about 19° C., about 20° C., about 21° C., about 22° C., about 23° C., about 24° C., about 25° C., about 26° C., about 27° C., about 28° C., about 29° C., about 30° C., about 37° C., or about 42° C. In some embodiments, the Zika virus preparation is treated with formalin at a temperature of 15° C. to 30° C. In some embodiments, the Zika virus preparation is treated with formalin at a temperature of 18° C. to 25° C. In some embodiments, the Zika virus preparation is treated with formalin at room temperature. In some embodiments, the Zika virus preparation is treated with formalin at a temperature of 22° C.

In some embodiments, the Zika virus preparation is treated with formalin for at least about 1 day. For example, the Zika virus preparation may be treated with formalin for at least about 1 day, at least about 2 days, at least about 3 days, at least about 4 days, at least about 5 days, at least about 6 days, at least about 7 days, at least about 8 days, at least about 9 days, at least about 10 days, at least about 11 days, at least about 12 days, at least about 13 days, at least about 14 days, at least about 15 days, at least about 16 days, at least about 17 days, at least about 18 days, at least about 19 days, at least about 20 days, at least about 21 days, at least about 22 days, at least about 23 days, at least about 24 days, at least about 25 days, at least about 26 days, at least about 27 days, at least about 28 days, at least about 29 days, at least about 30 days, or more. In some embodiments, the Zika virus preparation is treated with formalin for at least about 9 days. In some embodiments, the Zika virus preparation is treated with formalin for at least about 11 days. In some embodiments, the Zika virus preparation is treated with formalin for at least about 14 days. In some embodiments, the Zika virus preparation is treated with formalin for at least about 20 days. In some embodiments, the Zika virus preparation is treated with formalin for at least about 30 days. In some embodiments, the Zika virus preparation is treated with formalin for eight to twelve days. In some embodiments, the Zika virus preparation is treated with formalin for nine to eleven days. In some embodiments, the Zika virus preparation is treated with formalin for ten days.

In the middle of the inactivation treatment period, the mixture of the virus preparation and the formalin may be filtered to remove aggregates. After filtration the mixture of the virus preparation and the formalin is transferred to a new vessel and further treated with formalin until the end of the inactivation treatment period. In some embodiments, the mixture of the virus preparation and the formalin is filtered after four to six days of formalin treatment, if the overall formalin treatment period is eight to twelve days. In some embodiments, the mixture of the virus preparation and the formalin is filtered after five to six days of formalin treatment, if the overall formalin treatment period is nine to eleven days. In some embodiments, the mixture of the virus preparation and the formalin is filtered after five days of formalin treatment, if the overall formalin treatment period is ten days. A suitable filter for this step is a 0.2 μm filter.

In some embodiments, the Zika virus preparation is treated with 0.005 to 0.02% (w/v) formalin for eight to twelve days at a temperature of 15° C. to 30° C. In some embodiments, the Zika virus preparation is treated with 0.008 to 0.015% (w/v) formalin for nine to eleven days at a temperature of 18° C. to 25° C. In some embodiments, the Zika virus preparation is treated with 0.01% (w/v) formalin for ten days at a temperature of 22° C.

An inactivated whole Zika virus preparation is considered to be obtainable/obtained from a method wherein the Zika virus is treated with formaldehyde in an amount that ranges from about 0.02% w/v for 14 days at a temperature of 22° C. In some embodiments, an inactivated whole Zika virus preparation is considered to be obtainable/obtained from a method wherein the Zika virus is treated with formaldehyde in an amount of about 0.01% w/v for 10 days at a temperature of 22° C.

In some embodiments, the method further involves neutralizing unreacted formalin with an effective amount of sodium metabisulfite. In some embodiments, the effective amount of sodium metabisulfite ranges from about 0.01 mM to about 100 mM. For example, the sodium metabisulfite may be added at an effective concentration of from about 0.01 mM to about 100 mM, from about 0.1 mM to about 50 mM, from about 0.5 mM to about 20 mM, or from about 1 mM to about 10 mM, or at a concentration of about 0.01 mM, about 0.05 mM, about 0.1 mM, about 0.25 mM, about 0.5 mM, about 0.75 mM, about 1 mM, about 2 mM, about 3 mM, about 4 mM, about 5 mM, about 6 mM, about 7 mM, about 8 mM, about 9 mM, about 10 mM, about 20 mM, about 30 mM about 40 mM, about 50 mM, about 75 mM or about 100 mM. In some embodiments, the formalin is neutralized with about 2 mM sodium metabisulfite.

In some embodiments, the Zika virus preparation is treated with hydrogen peroxide. In some embodiments, the Zika virus preparation is treated with hydrogen peroxide at concentrations ranging from 0.1 to 3%, or 0.1 to 1% at any temperature from 20° C. to 30° C. for 5 to 120 minutes. In some embodiments, the Zika virus preparation is treated with hydrogen peroxide at a final concentration of 0.01% for 60 minutes or less.

In some embodiments, the method involves (a) isolating the Zika virus preparation from one or more cells cultured in vitro that are used to produce the virus preparation; (b) purifying the virus preparation by one or more purification steps; (c) treating the virus preparation with an effective amount of formalin; (d) neutralizing the virus preparation with an effective amount of sodium metabisulfite; and (e) preparing a pharmaceutical composition comprising the inactivated Zika virus. Any method of purifying a virus preparation known in the art may be employed to isolate the Zika virus, including, without limitation, using cross flow filtration (CFF), multimodal chromatography, size exclusion chromatography, cation exchange chromatography, and/or anion exchange chromatography. In some embodiments, the virus preparation is isolated by cross flow filtration (CFF). In some embodiments, the virus preparation is purified to a high degree in an amount that is about 70%, about 75%, about 80%, about 85%, about 90%, about 91%, about 92%, about 93%, about 94%, about 95% about 96%, about 97%, about 98%, about 99%, or more.

In some embodiments, the Zika virus may be selected from the group of strains consisting of strains Mr 766, ArD 41519, IbH 30656, P6-740, EC Yap, FSS13025, ArD 7117, ArD 9957, ArD 30101, ArD 30156, ArD 30332, HD 78788, ArD 127707, ArD 127710, ArD 127984, ArD 127988, ArD 127994, ArD 128000, ArD 132912, 132915, ArD 141170, ArD 142623, ArD 149917, ArD 149810, ArD 149938, ArD 157995, ArD 158084, ArD 165522, ArD 165531, ArA 1465, ArA 27101, ArA 27290, ArA 27106, ArA 27096, ArA 27407, ArA 27433, ArA 506/96, ArA 975-99, Ara 982-99, ArA 986-99, ArA 2718, ArB 1362, Nigeria68, Malaysia66, Kedougou84, Suriname, MR1429, PRVABC59, ECMN2007, DakAr41524, H/PF/2013, R103451, 103344, 8375, JMB-185, ZIKV/H, sapiens/Brazil/Natal/2015, SPH2015, ZIKV/Hu/Chiba/S36/2016, Thailand SV0127/14, Philippine COC C0740, Brazil Fortaleza 2015 and Cuba2017.

In certain embodiments, the Zika virus includes a mutation in Zika virus Non-structural protein 1 (NS1). In some embodiments, the Zika virus contains a Trp98Gly mutation at position 98 of SEQ ID NO: 1, or at a position corresponding to position 98 of SEQ ID NO: 1. In some embodiments, the vaccine or immunogenic composition comprises a purified inactivated whole Zika virus comprising a Trp98Gly mutation at position 98 of SEQ ID NO: 1, or at a position corresponding to position 98 of SEQ ID NO: 1, wherein the Zika virus is derived from strain PRVABC59. In some embodiments, the vaccine or immunogenic composition comprises a purified inactivated whole Zika virus comprising a Trp98Gly mutation at position 98 of SEQ ID NO: 1, or at a position corresponding to position 98 of SEQ ID NO: 1, wherein the Zika virus is derived from strain PRVABC59 comprising the genomic sequence according to SEQ ID NO: 2. In some embodiments, the vaccine or immunogenic composition comprises a purified inactivated whole Zika which differs from strain PRVABC59 in a Trp98Gly mutation at position 98 of SEQ ID NO: 1.

The vaccines and/or immunogenic compositions of the present disclosure containing one or more antigens from at least one inactivated Zika virus may be useful for treating or preventing Zika virus infection in a subject in need thereof and/or inducing an immune response, such as a protective immune response, against Zika virus in a subject in need thereof.

Determining Completeness of Inactivation

Other aspects of the present disclosure relate to methods for determining the completeness of inactivation of an arbovirus preparation by using the sequential infection of two different cell types. This method has a surprisingly low limit of detection (LOD) compared to an assay which only uses one cell type and also compared to other methods, such as the TCID50 method. Further, this method avoids the use of animals to determine infectivity of the inactivated virus.

The method for determining the completeness of inactivation of an arbovirus preparation comprises the following steps:
(i) inoculating cultured insect cells with an arbovirus preparation which was subjected to an inactivation step and incubating the insect cells for a first period of time, thereby producing an insect cell supernatant;
(ii) inoculating cultured mammalian cells with the insect cell supernatant produced in (i) and incubating the mammalian cells for a second period of time; and
(iii) determining whether the virus preparation contains a residual replicating virus that produces a cytopathic effect on the mammalian cells.

Arboviruses are viruses which are transmitted to humans by arthropods. They include viruses from the genera flavivirus, togavirus and bunyavirus. The arbovirus preparation examined by the method disclosed herein contains an arbovirus which is able to infect mammalian cells, in particular Vero cells, and to cause a cytopathic effect on these cells. In some embodiments, the arbovirus is selected from a Zika virus, a West Nile virus, a Yellow Fever virus, a Japanese Encephalitis virus, a dengue virus, a St. Louis Encephalitis virus, tick-borne encephalitis virus, a Chikungunya virus, a O'nyong'nyong virus or a Mayarovirus. In some embodiments, the arbovirus is a Zika virus.

In some embodiments, the Zika virus may be selected from the group of strains consisting of strains Mr 766, ArD 41519, IbH 30656, P6-740, EC Yap, FSS13025, ArD 7117, ArD 9957, ArD 30101, ArD 30156, ArD 30332, HD 78788, ArD 127707, ArD 127710, ArD 127984, ArD 127988, ArD 127994, ArD 128000, ArD 132912, 132915, ArD 141170, ArD 142623, ArD 149917, ArD 149810, ArD 149938, ArD 157995, ArD 158084, ArD 165522, ArD 165531, ArA 1465, ArA 27101, ArA 27290, ArA 27106, ArA 27096, ArA 27407, ArA 27433, ArA 506/96, ArA 975-99, Ara 982-99, ArA 986-99, ArA 2718, ArB 1362, Nigeria68, Malaysia66, Kedougou84, Suriname, MR1429, PRVABC59, ECMN2007, DakAr41524, H/PF/2013, R103451, 103344, 8375, JMB-185, ZIKV/H, sapiens/Brazil/Natal/2015, SPH2015, ZIKV/Hu/Chiba/S36/2016, Thailand SV0127/14, Philippine COC C0740, Brazil Fortaleza 2015 and Cuba2017.

In certain embodiments, the Zika virus includes a mutation in Zika virus Non-structural protein 1 (NS1). In some embodiments, the Zika virus contains a Trp98Gly mutation at position 98 of SEQ ID NO: 1, or at a position corresponding to position 98 of SEQ ID NO: 1. In some embodiments, the vaccine or immunogenic composition comprises a purified inactivated whole Zika virus comprising a Trp98Gly mutation at position 98 of SEQ ID NO: 1, or at a position corresponding to position 98 of SEQ ID NO: 1, wherein the Zika virus is derived from strain PRVABC59. In some embodiments, the vaccine or immunogenic composition comprises a purified inactivated whole Zika virus comprising a Trp98Gly mutation at position 98 of SEQ ID NO: 1, or at a position corresponding to position 98 of SEQ ID NO: 1, wherein the Zika virus is derived from strain PRVABC59 comprising the genomic sequence according to SEQ ID NO: 2. In some embodiments, the vaccine or immunogenic composition comprises a purified inactivated whole Zika which differs from strain PRVABC59 in a Trp98Gly mutation at position 98 of SEQ ID NO: 1.

The cultured insect cells are inoculated with the arbovirus preparation by adding the arbovirus preparation to the insect cell culture which contains insect cells and growth medium. The inoculated insect cells are then incubated for a first period of time with the arbovirus preparation under suitable conditions. In some embodiments, the first period of time is three to seven days. In some embodiments, the first period of time is five to seven days. In some embodiments, the first period of time is six days. Hence, in some embodiments the inoculated insect cells are incubated with the arbovirus preparation for three to seven days. In some embodiments, the inoculated insect cells are incubated with the arbovirus preparation for five to seven days. In some embodiments, the inoculated insect cells are incubated with the arbovirus preparation for six days. During the incubation, any live virus will be secreted into the insect cell supernatant.

The insect cells used may be any insect cells which can be infected by the arbovirus to be investigated and whose viability is not altered by virus infection. The insect cells are selected such that the virus does not have a cytopathic effect on the cells. Suitable insect cells include, but are not limited to, CCL-125 cells, Aag-2 cells, RML-12 cells, C6/36 cells, C7-10 cells, AP-61 cells, A.t. GRIP-1 cells, A.t. GRIP-2 cells, A.t. GRIP-3 cells, UM-AVE1 cells, Mos.55 cells, Sua1B cells, 4a-3B cells, Mos.42 cells, MSQ43 cells, LSB-AA695BB cells, NIID-CTR cells and TRA-171 cells. In some embodiments, the insect cells are C6/36 cells.

The insect cell supernatant produced by incubating the insect cells with the arbovirus preparation is then used to inoculate cultured mammalian cells. For inoculation the insect cell supernatant is transferred to the mammalian cells and incubated with the mammalian cells for 60 to 120 minutes or for 80 to 100 minutes or for 90 minutes. After the inoculation cell culture medium is added and the mammalian cells are incubated with the insect cell supernatant for a second period of time under suitable conditions. In some embodiments, the second period of time is three to 14 days. In some embodiments, the second period of time is five to twelve days. In some embodiments, the second period of time is six to ten days. In some embodiments, the second period of time is seven to nine days. In some embodiments, the second period of time is eight days. Hence, in some embodiments the inoculated mammalian cells are incubated with the insect cell supernatant for three to 14 days. In some embodiments, the inoculated mammalian cells are incubated with the insect cell supernatant for five to twelve days. In some embodiments, the inoculated mammalian cells are incubated with the insect cell supernatant for seven to nine days. In some embodiments, the inoculated mammalian cells are incubated with the insect cell supernatant for eight days. During the incubation, any live virus will exert a cytopathic effect on the mammalian cells. During the incubation, any residual replicating virus will exert a cytopathic effect on the mammalian cells such as Vero cells.

The mammalian cells used may be any mammalian cells which can be infected by the arbovirus to be investigated and on which the virus exerts a cytopathic effect. Suitable mammalian cells include, but are not limited to, VERO cells, LLC-MK2 cells, MDBK cells, MDCK cells, ATCC CCL34 MDCK (NBL2) cells, MDCK 33016 (deposit number DSM ACC 2219 as described in WO97/37001) cells, BHK21-F cells, HKCC cells, and Chinese hamster ovary cells (CHO cells). In some embodiments, the mammalian cells are Vero cells.

In some embodiments, the method for determining the completeness of inactivation of an arbovirus preparation comprises the following steps:
(i) inoculating C6/36 cells with an arbovirus preparation which was subjected to an inactivation step and incubating the insect cells for a first period of time, thereby producing a C6/36 cell supernatant;
(ii) inoculating cultured mammalian cells with the C6/36 cell supernatant produced in (i) and incubating the mammalian cells for a second period of time; and
(iii) determining whether the virus preparation contains a residual replicating virus that produces a cytopathic effect on the mammalian cells.

In some embodiments, the method for determining the completeness of inactivation of an arbovirus preparation comprises the following steps:
(i) inoculating cultured insect cells with an arbovirus preparation which was subjected to an inactivation step and incubating the insect cells for a first period of time, thereby producing an insect cell supernatant;
(ii) inoculating Vero cells with the insect cell supernatant produced in (i) and incubating the mammalian cells for a second period of time; and
(iii) determining whether the virus preparation contains a residual replicating virus that produces a cytopathic effect on the mammalian cells.

In some embodiments, the method for determining the completeness of inactivation of an arbovirus preparation comprises the following steps:
(i) inoculating C6/36 cells with an arbovirus preparation which was subjected to an inactivation step and incubating the insect cells for a first period of time, thereby producing an C6/36 cell supernatant;
(ii) inoculating Vero cells with the C6/36 cell supernatant produced in (i) and incubating the mammalian cells for a second period of time; and
(iii) determining whether the virus preparation contains a residual replicating virus that produces a cytopathic effect on the mammalian cells.

In some embodiments, the method for determining the completeness of inactivation of a Zika virus preparation comprises the following steps:
(i) inoculating C6/36 cells with an arbovirus preparation which was subjected to an inactivation step and incubating the insect cells for a first period of time, thereby producing an C6/36 cell supernatant;
(ii) inoculating Vero cells with the C6/36 cell supernatant produced in (i) and incubating the mammalian cells for a second period of time; and
(iii) determining whether the virus preparation contains a residual replicating virus that produces a cytopathic effect on the mammalian cells.

In some embodiments, the method for determining the completeness of inactivation of a Zika virus preparation comprises the following steps:
(i) inoculating C6/36 cells with an arbovirus preparation which was subjected to an inactivation step and incubating the insect cells for three to seven days, thereby producing an C6/36 cell supernatant;
(ii) inoculating Vero cells with the C6/36 cell supernatant produced in (i) and incubating the mammalian cells for a second period of time; and
(iii) determining whether the virus preparation contains a residual replicating virus that produces a cytopathic effect on the mammalian cells.

In some embodiments, the method for determining the completeness of inactivation of a Zika virus preparation comprises the following steps:
(i) inoculating C6/36 cells with an arbovirus preparation which was subjected to an inactivation step and incubating the insect cells for a first period of time, thereby producing an C6/36 cell supernatant;
(ii) inoculating Vero cells with the C6/36 cell supernatant produced in (i) and incubating the mammalian cells for three to 14 days; and
(iii) determining whether the virus preparation contains a residual replicating virus that produces a cytopathic effect on the mammalian cells.

In some embodiments, the method for determining the completeness of inactivation of a Zika virus preparation comprises the following steps:
(i) inoculating C6/36 cells with an arbovirus preparation which was subjected to an inactivation step and incubating the insect cells for three to seven days, thereby producing an C6/36 cell supernatant;
(ii) inoculating Vero cells with the C6/36 cell supernatant produced in (i) and incubating the mammalian cells for three to 14 days; and
(iii) determining whether the virus preparation contains a residual replicating virus that produces a cytopathic effect on the mammalian cells.

In some embodiments, the method for determining the completeness of inactivation of a Zika virus preparation comprises the following steps:
(i) inoculating C6/36 cells with an arbovirus preparation which was subjected to an inactivation step and incubating the insect cells for six days, thereby producing an C6/36 cell supernatant;
(ii) inoculating Vero cells with the C6/36 cell supernatant produced in (i) and incubating the mammalian cells for eight days; and
(iii) determining whether the virus preparation contains a residual replicating virus that produces a cytopathic effect on the mammalian cells.

At the end of the second period of time it is determined whether the virus preparation has a cytopathic effect on the mammalian cells. A cytopathic effect is any change in the cell structure caused by viral invasion, infection, and budding from the cells during viral replication. In the method of the present disclosure, the cytopathic effect is determined by a change in the media color from pink to orange or yellow, if the cells are cultured in a medium containing phenol red, or by a microscopic examination of the mammalian cells. If the microscopic examination of the mammalian cells shows that the cells round, begin to pull away from the tissue culture vessel (plate, well or flask), or clear from the tissue culture plate/flask, it is considered that a cytopathic effect is present. Other indicia of a cytopathic effect include the fusion of adjacent cells to form syncytia and the appearance of nuclear or cytoplasmic inclusion bodies.

As discussed above, the method disclosed herein has a very low limit of detection. With this method a virus content of less than 1.0 $TCID_{50}$ can be detected. In some embodiments, a virus content of less than 0.8 $TCID_{50}$ can be detected. In some embodiments, a virus content of less than 0.5 $TCID_{50}$ can be detected. In some embodiments, a virus content of less than 0.2 $TCID_{50}$ can be detected. In some embodiments, a virus content of less than 0.1 $TCID_{50}$ can be detected.

The above method for determining the completeness of inactivation can be used in any method of inactivating an arbovirus. In one embodiment, the method for inactivating an arbovirus preparation comprises:
(a) isolating the arbovirus preparation from one or more cells cultured in vitro, wherein the cells are used to produce the arbovirus preparation;
(b) treating the arbovirus preparation with 0.005% to 0.02% w/v of formaldehyde;
(c) determining the completeness of inactivation by:
(i) inoculating cultured insect cells with a virus preparation treated according to step (b) and incubating the insect cells for a first period of time, thereby producing a supernatant;

(ii) inoculating cultured mammalian cells with the supernatant produced in (i) and incubating the mammalian cells for a second period of time; and
(iii) determining whether the arbovirus preparation contains a residual replicating virus that produces a cytopathic effect on the mammalian cells.

In some embodiments, the method for inactivating an arbovirus preparation comprises:
(a) isolating the arbovirus preparation from one or more cells cultured in vitro, wherein the cells are used to produce the arbovirus preparation;
(b) treating the arbovirus preparation with 0.1 to 3% hydrogen peroxide at a temperature of 20° C. to 30° C. for 5 to 120 minutes;
(c) determining the completeness of inactivation by:
 (i) inoculating cultured insect cells with a virus preparation treated according to step (b) and incubating the insect cells for a first period of time, thereby producing a supernatant;
 (ii) inoculating cultured mammalian cells with the supernatant produced in (i) and incubating the mammalian cells for a second period of time; and
 (iii) determining whether the arbovirus preparation contains a residual replicating virus that produces a cytopathic effect on the mammalian cells.

In some embodiments, the method for inactivating an arbovirus preparation comprises:
(a) isolating the arbovirus preparation from one or more cells cultured in vitro, wherein the cells are used to produce the arbovirus preparation;
(b) treating the arbovirus preparation with 0.01% hydrogen peroxide at a temperature of 20° C. to 30° C. for 60 minutes;
(c) determining the completeness of inactivation by:
 (i) inoculating cultured insect cells with a virus preparation treated according to step (b) and incubating the insect cells for a first period of time, thereby producing a supernatant;
 (ii) inoculating cultured mammalian cells with the supernatant produced in (i) and incubating the mammalian cells for a second period of time; and
 (iii) determining whether the arbovirus preparation contains a residual replicating virus that produces a cytopathic effect on the mammalian cells.

The above method for determining the completeness of inactivation can be used in any method of inactivating a Zika virus. In one embodiment, the method for inactivating a Zika virus preparation comprises:
(a) isolating the Zika virus preparation from one or more cells cultured in vitro, wherein the cells are used to produce the Zika virus preparation;
(b) treating the Zika virus preparation with 0.005% to 0.02% w/v of formaldehyde;
(c) determining the completeness of inactivation by:
 (i) inoculating cultured insect cells with the Zika virus preparation treated according to step (b) and incubating the insect cells for a first period of time, thereby producing a supernatant;
 (ii) inoculating cultured mammalian cells with the supernatant produced in (i) and incubating the mammalian cells for a second period of time; and
 (iii) determining whether the Zika virus preparation contains a residual replicating virus that produces a cytopathic effect on the mammalian cells.

In some embodiments, the method of inactivating a Zika virus preparation comprises:
(a) isolating the Zika virus preparation from one or more cells cultured in vitro, wherein the cells are used to produce the Zika virus preparation;
(b) treating the virus Zika preparation with 0.1 to 3% hydrogen peroxide at a temperature of 20° C. to 30° C. for 5 to 120 minutes;
(c) determining the completeness of inactivation by:
 (i) inoculating cultured insect cells with the Zika virus preparation treated according to step (b) and incubating the insect cells for a first period of time, thereby producing a supernatant;
 (ii) inoculating cultured mammalian cells with the supernatant produced in (i) and incubating the mammalian cells for a second period of time; and
 (iii) determining whether the Zika virus preparation contains a residual replicating virus that produces a cytopathic effect on the mammalian cells.

In some embodiments, the method of inactivating a Zika virus preparation comprises:
(a) isolating the Zika virus preparation from one or more cells cultured in vitro, wherein the cells are used to produce the Zika virus preparation;
(b) treating the Zika virus preparation with 0.01% hydrogen peroxide at a temperature of 20° C. to 30° C. for 60 minutes;
(c) determining the completeness of inactivation by:
 (i) inoculating insect cells with the Zika virus preparation treated according to step (b) and incubating the insect cells for a first period of time, thereby producing a supernatant;
 (ii) inoculating mammalian cells with the supernatant produced in (i) and incubating the mammalian cells for a second period of time; and
 (iii) determining whether the Zika virus preparation contains a residual replicating virus that produces a cytopathic effect on the mammalian cells.

In some embodiments, the method of inactivating a Zika virus preparation comprises:
(a) isolating the Zika virus preparation from one or more cells cultured in vitro, wherein the cells are used to produce the Zika virus preparation;
(b) treating the Zika virus preparation with 0.05% formalin at a temperature of 20° C. to 30° C., such as 22° C., for seven days;
(c) determining the completeness of inactivation by:
 (i) inoculating cultured insect cells with the Zika virus preparation treated according to step (b) and incubating the insect cells for a first period of time, thereby producing a supernatant;
 (ii) inoculating cultured mammalian cells with the supernatant produced in (i) and incubating the mammalian cells for a second period of time; and
 (iii) determining whether the virus preparation contains a residual replicating virus that produces a cytopathic effect on the mammalian cells.

In some embodiments, the cells are non-human cells. Suitable non-human mammalian cells include, but are not limited to, VERO cells, LLC-MK2 cells, MDBK cells, MDCK cells, ATCC CCL34 MDCK (NBL2) cells, MDCK 33016 (deposit number DSM ACC 2219 as described in WO97/37001) cells, BHK21-F cells, HKCC cells, and Chinese hamster ovary cells (CHO cells). In some embodiments, the mammalian cells are Vero cells.

Adjuvants

Other aspects of the present disclosure relate to Zika virus vaccines and/or immunogenic compositions containing one or more antigens from at least one Zika virus described herein in combination with one or more adjuvants. In some embodiments, the vaccines and/or immunogenic compositions contain a purified inactivated whole Zika virus such as a Zika virus with a mutation which is a tryptophan to glycine substitution at position 98 of SEQ ID NO: 1 or at a position corresponding to position 98 of SEQ ID NO: 1 as described herein in combination with one or more adjuvants. In some embodiments, the vaccine or immunogenic composition comprises a purified inactivated whole Zika virus comprising a Trp98Gly mutation at position 98 of SEQ ID NO: 1, or at a position corresponding to position 98 of SEQ ID NO: 1, wherein the Zika virus is derived from strain PRVABC59 in combination with one or more adjuvants. In some embodiments, the vaccine or immunogenic composition comprises a purified inactivated whole Zika virus comprising a Trp98Gly mutation at position 98 of SEQ ID NO: 1, or at a position corresponding to position 98 of SEQ ID NO: 1, wherein the Zika virus is derived from strain PRVABC59 comprising the genomic sequence according to SEQ ID NO: 2 in combination with one or more adjuvants. In one embodiment, the vaccines and immunogenic compositions contain a plaque purified clonal Zika virus isolate in combination with one or more adjuvants. Such adjuvanted vaccines and/or immunogenic compositions of the present disclosure may be useful for treating or preventing Zika virus infection in a subject in need thereof and/or inducing an immune response, such as a protective immune response, against Zika virus in a subject in need thereof.

Various methods of achieving an adjuvant effect for vaccines are known and may be used in conjunction with the Zika virus vaccines and/or immunogenic compositions disclosed herein. General principles and methods are detailed in "The Theory and Practical Application of Adjuvants", 1995, Duncan E. S. Stewart-Tull (ed.), John Wiley & Sons Ltd, ISBN 0-471-95170-6, and also in "Vaccines: New Generation Immunological Adjuvants", 1995, Gregoriadis G et al. (eds.), Plenum Press, New York, ISBN 0-306-45283-9.

Exemplary adjuvants may include, but are not limited to, aluminum salts, calcium phosphate, toll-like receptor (TLR) agonists, monophosphoryl lipid A (MLA), MLA derivatives, synthetic lipid A, lipid A mimetics or analogs, cytokines, saponins, muramyl dipeptide (MDP) derivatives, CpG oligos, lipopolysaccharide (LPS) of gram-negative bacteria, polyphosphazenes, emulsions (oil emulsions), chitosan, vitamin D, stearyl or octadecyl tyrosine, virosomes, cochleates, poly(lactide-co-glycolides) (PLG) microparticles, poloxamer particles, microparticles, liposomes, Complete Freund's Adjuvant (CFA), and Incomplete Freund's Adjuvant (IFA). In some embodiments, the adjuvant is an aluminum salt.

In some embodiments, the adjuvant includes at least one of alum, aluminum phosphate, aluminum hydroxide, potassium aluminum sulfate, and Alhydrogel 85. In some embodiments, aluminum salt adjuvants of the present disclosure have been found to increase adsorption of the antigens of the Zika virus vaccines and/or immunogenic compositions of the present disclosure. Accordingly, in some embodiments, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or about 100% of the antigen is adsorbed to the aluminum salt adjuvant.

Certain embodiments of the present disclosure include a method for preparing an adjuvanted Zika virus vaccine or immunogenic composition, which involves (a) mixing the vaccine or immunogenic composition with an aluminum salt adjuvant, with the vaccine or immunogenic composition including one or more antigens from at least one Zika virus described herein and (b) incubating the mixture under suitable conditions for a period of time that ranges from about 1 hour to about 24 hours (e.g., about 16 hours to about 24 hours), with at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or about 100% of the antigen adsorbed to the aluminum salt adjuvant. In certain embodiments of the method, the at least one Zika virus is a Zika virus comprising a non-human cell adaptation mutation (e.g., a non-human cell adaptation mutation in protein NS1 such as a Trp98Gly mutation). In some embodiments, the at least one Zika virus is a purified inactivated whole Zika virus comprising a Trp98Gly mutation at position 98 of SEQ ID NO: 1, or at a position corresponding to position 98 of SEQ ID NO: 1, wherein the Zika virus is derived from strain PRVABC59. In some embodiments, the Zika virus is a purified inactivated whole Zika virus comprising a Trp98Gly mutation at position 98 of SEQ ID NO: 1, or at a position corresponding to position 98 of SEQ ID NO: 1, wherein the Zika virus is derived from strain PRVABC59 comprising the genomic sequence according to SEQ ID NO: 2.

Virus Purification

Further aspects of the present disclosure relate to methods of purifying Zika virus. In some embodiments, the method includes inoculating a plurality of cells with an inoculum containing a population of Zika viruses, and obtaining from one or more of the inoculated cells a Zika virus clonal isolate by plaque purification. In some embodiments, the cells are non-human cells (e.g., insect cells, mammalian cells, etc.). In some embodiments, the cells are insect cells (such as any of the mosquito cells/cell lines described herein). In some embodiments, the cells are mammalian cells (such as any of the mammalian cells/cell lines described herein). In some embodiments, the mammalian cells are monkey cells.

In some embodiments, the population of Zika virus is heterogeneous (e.g., comprising two or more genotypes). In some embodiments, the population of Zika viruses comprises a Zika virus clinical isolate (e.g., from strain PRVABC59) and/or one or more Zika viruses that have been previously passaged in cell culture. In some embodiments, plaque purification (e.g., as described herein) allows for the substantial and/or complete separation of a (genetically homogenous) clonal isolate from a heterogeneous viral population. In some embodiments, the monkey cells are from a VERO cell line (e.g., VERO 10-87 cells). In some embodiments, the inoculum comprises human serum. In some embodiments, the inoculum comprises one or more adventitious agents (e.g., one or more contamination viruses). In some embodiments, plaque purification (e.g., as described herein) allows for the substantial and/or complete purification of a (genetically homogenous) clonal isolate away from one or more adventitious agents.

In some embodiments, the methods described for isolating and/or purifying a Zika virus clonal includes one or more (e.g., one or more, two or more, three or more, four or more, five or more, etc.) additional plaque purifications of the Zika virus clonal isolate. In some embodiments, the methods described for isolating and/or purifying a Zika virus clonal isolate includes passaging the Zika virus clonal isolate one or more (e.g., one or more, two or more, three or more, four or more, five or more, etc.) times in cell culture (e.g., in insect cells such as a mosquito cell line and/or in mammalian cells such as a VERO cell line).

Further aspects of the present disclosure relate to methods of purifying Zika virus for the preparation of a vaccine or immunogenic composition. In some embodiments, the methods include one or more (e.g., one or more, two or more, three or more, four or more, five or more, or six) steps of (in any order, including the following order): performing depth filtration of a sample or preparation containing a Zika virus; buffer exchanging and/or diluting a sample containing a Zika virus (e.g., by cross flow filtration (CFF)) to produce a retentate; binding a sample comprising a Zika virus to an ion exchange membrane (e.g., an anion exchange membrane, a cation exchange membrane) to produce a bound fraction, where the bound fraction comprises the Zika virus, and eluting the bound fraction from the ion exchange membrane; treating a sample containing a Zika virus with an effective amount of any of the chemical inactivators described herein; neutralizing a sample containing a chemically inactivated Zika virus with sodium metabisulfite; and/or purifying a neutralized sample comprising a chemically inactivated Zika virus (e.g., by cross flow filtration (CFF)). In some embodiments, the method includes the steps of (a) passing a sample containing a Zika virus through a first depth filter to produce a first eluate, where the first eluate contains the Zika virus; (b) buffer exchanging and/or diluting the first eluate by cross flow filtration (CFF) to produce a first retentate, where the first retentate contains the Zika virus; (c) binding the first retentate to an ion exchange membrane to produce a first bound fraction, where the first bound fraction contains the Zika virus, and eluting the first bound fraction from the ion exchange membrane to produce a second eluate, where the second eluate contains the Zika virus; (d) passing the second eluate through a second depth filter to produce a second retentate, wherein the second retentate contains the Zika virus; (e) treating the second retentate with an effective amount of a chemical inactivator; (f) neutralizing the treated second retentate with sodium metabisulfite; and (g) purifying the neutralized second retentate by cross flow filtration (CFF).

Formulations of Vaccines and/or Immunogenic Compositions

Further aspects of the present disclosure relate to formulations of vaccines and/or immunogenic compositions of the present disclosure containing one or more antigens from a Zika virus described herein. In some embodiments, the Zika virus is a purified inactivated whole Zika virus. In some embodiments, the purified inactivated whole Zika virus comprises a mutation at position 98 of SEQ ID NO: 1, or at a position corresponding to position 98 of SEQ ID NO: 1. In some embodiments, the purified inactivated whole Zika virus comprises a Trp98Gly mutation at position 98 of SEQ ID NO: 1, or at a position corresponding to position 98 of SEQ ID NO: 1. In some embodiments, the purified inactivated whole Zika virus comprises a Trp98Gly mutation at position 98 of SEQ ID NO: 1, or at a position corresponding to position 98 of SEQ ID NO: 1, wherein the Zika virus is derived from strain PRVABC59. In some embodiments, the purified inactivated whole Zika virus comprises a Trp98Gly mutation at position 98 of SEQ ID NO: 1, or at a position corresponding to position 98 of SEQ ID NO: 1, wherein the Zika virus is derived from strain PRVABC59 comprising the genomic sequence according to SEQ ID NO: 2.

Such vaccines and/or immunogenic compositions of the present disclosure containing one or more antigens from a Zika virus described herein may be useful for treating or preventing Zika virus infection in a subject in need thereof and/or inducing an immune response, such as a protective immune response, against Zika virus in a subject in need thereof.

Typically, vaccines and/or immunogenic compositions of the present disclosure are prepared as injectables either as liquid solutions or suspensions; solid forms suitable for solution in, or suspension in, liquid prior to injection may also be prepared. Such preparations may also be emulsified or produced as a dry powder. The active immunogenic ingredient is often mixed with excipients which are pharmaceutically acceptable and compatible with the active ingredient. Suitable excipients are, for example, water, saline, dextrose, sucrose, glycerol, ethanol, or the like, and combinations thereof. In addition, if desired, the vaccine or immunogenic composition may contain auxiliary substances such as wetting or emulsifying agents, pH buffering agents, or adjuvants which enhance the effectiveness of the vaccine or immunogenic composition.

Vaccines or immunogenic compositions may be conventionally administered parenterally, by injection, for example, either subcutaneously, transcutaneously, intradermally, subdermally or intramuscularly. Additional formulations which are suitable for other modes of administration include suppositories and, in some cases, oral, peroral, intranasal, buccal, sublingual, intraperitoneal, intravaginal, anal and intracranial formulations. For suppositories, traditional binders and carriers may include, for example, polyalkalene glycols or triglycerides; such suppositories may be formed from mixtures containing the active ingredient in the range of 0.5% to 10%, or even 1-2%. In certain embodiments, a low melting wax, such as a mixture of fatty acid glycerides or cocoa butter is first melted and the Zika virus vaccine and/or immunogenic composition described herein is dispersed homogeneously, for example, by stirring. The molten homogeneous mixture is then poured into conveniently sized molds and allowed to cool and to solidify.

The vaccines and/or immunogenic compositions of the present disclosure may be administered in a manner compatible with the dosage formulation, and in such amount as will be therapeutically effective and immunogenic. The quantity to be administered depends on the subject to be treated, including, e.g., the capacity of the individual's immune system to mount an immune response, and the degree of protection desired. Suitable dosage ranges may include, for example, from about 0.1 µg to about 100 µg of the purified inactivated whole Zika virus. The amount of the purified inactivated Zika virus can be determined by a Bradford assay (Bradford et al. (1976) Anal. Biochem. 72: 248-254) using defined amounts of recombinant Zika envelope protein to establish the standard curve.

Suitable regimens for initial administration and booster shots are also variable but are typified by an initial administration followed by subsequent inoculations or other administrations.

The manner of application may be varied widely. Any of the conventional methods for administration of a vaccine or immunogenic composition are applicable. These include oral application on a solid physiologically acceptable base or in a physiologically acceptable dispersion, parenterally, by injection or the like. The dosage of the vaccine or immunogenic composition will depend on the route of administration and may vary according to the age of the person to be vaccinated and the formulation of the antigen. The vaccine or immunogenic composition can have a unit dosage volume of more than 0.5 mL, of 0.5 mL or of less than 0.5 mL, as described herein. For instance, it can be administered at a volume of 0.25 mL.

To control tonicity, it is preferred to include a physiological salt, such as a sodium salt. Sodium chloride (NaCl) is preferred, which may be present at between 1 and 20 mg/ml. Other salts that may be present include potassium chloride, potassium dihydrogen phosphate, disodium phosphate dehydrate, magnesium chloride, calcium chloride, etc.

Vaccines and/or immunogenic compositions of the present disclosure may include one or more buffers. Typical buffers include: a phosphate buffer; a Tris buffer; a borate buffer; a succinate buffer; a histidine buffer (particularly with an aluminum hydroxide adjuvant); or a citrate buffer. Buffers will typically be included in the 5-20 mM range The pH of a vaccine or immunogenic composition will generally be between 5.0 and 8.5 or 5.0 and 8.1, and more typically between 6.0 and 8.5 e.g. between 6.0 and 8.0, between 6.5 and 8.0, between 6.5 and 7.5, between 7.0 and 8.5, between 7.0 and 8.0, or between 7.0 and 7.8. A manufacturing process of the present disclosure may therefore include a step of adjusting the pH of the bulk vaccine prior to packaging.

The vaccine or immunogenic composition is preferably sterile. It is preferably non pyrogenic, e.g. containing <1 EU (endotoxin unit, a standard measure) per dose, and preferably <0.1 EU per dose. It is preferably gluten free.

In certain embodiments, the vaccines and/or immunogenic compositions of the present disclosure may include a detergent in an effective concentration. In some embodiments, an effective amount of detergent may include without limitation, about 0.00005% v/v to about 5% v/v or about 0.0001% v/v to about 1% v/v. In certain embodiments, an effective amount of detergent is about 0.001% v/v, about 0.002% v/v, about 0.003% v/v, about 0.004% v/v, about 0.005% v/v, about 0.006% v/v, about 0.007% v/v, about 0.008% v/v, about 0.009% v/v, or about 0.01% v/v. Without wishing to be bound by theory, detergents help maintain the vaccines and/or immunogenic compositions of the present disclosure in solution and help to prevent the vaccines and/or immunogenic compositions from aggregating.

Suitable detergents include, for example, polyoxyethylene sorbitan ester surfactant (known as 'Tweens'), octoxynol (such as octoxynol-9 (Triton X 100) or t-octylphenoxypolyethoxyethanol), cetyl trimethyl ammonium bromide ('CTAB'), and sodium deoxycholate. The detergent may be present only at trace amounts. Other residual components in trace amounts could be antibiotics (e.g. neomycin, kanamycin, polymyxin B). In some embodiments, the detergent contains polysorbate. In some embodiments, the effective concentration of detergent includes ranges from about 0.00005% v/v to about 5% v/v.

The vaccines and/or immunogenic compositions are preferably stored at between 2° C. and 8° C. They should ideally be kept out of direct light. The antigen and emulsion will typically be in admixture, although they may initially be presented in the form of a kit of separate components for extemporaneous admixing. Vaccines and/or immunogenic compositions will generally be in aqueous form when administered to a subject.

Methods of the Present Disclosure

Further aspects of the present disclosure relate to methods for using vaccines and/or immunogenic compositions described herein containing a purified inactivated whole Zika virus, such as a Zika virus with a mutation which is a tryptophan to glycine substitution at position 98 of SEQ ID NO: 1 or at a position corresponding to position 98 of SEQ ID NO: 1 as described herein) to treat or prevent Zika virus in a subject in need thereof and/or induce an immune response to Zika virus in a subject in need thereof. Further aspects of the present disclosure relate to methods for using vaccines and/or immunogenic compositions described herein containing a purified inactivated whole Zika virus with a mutation which is a tryptophan to glycine substitution at position 98 of SEQ ID NO: 1 or at a position corresponding to position 98 of SEQ ID NO: 1 to treat or prevent Zika virus in a subject in need thereof and/or to induce an immune response to Zika virus in a subject in need thereof. Further aspects of the present disclosure relate to methods for using vaccines and/or immunogenic compositions described herein containing a purified inactivated whole Zika virus with a mutation which is a tryptophan to glycine substitution at position 98 of SEQ ID NO:1 or at a position corresponding to position 98 of SEQ ID NO: 1, wherein the Zika virus is derived from strain PRVABC59, to treat or prevent Zika virus in a subject in need thereof and/or to induce an immune response to Zika virus in a subject in need thereof. Further aspects of the present disclosure relate to methods for using vaccines and/or or immunogenic compositions described herein containing a purified inactivated whole Zika virus with a mutation which is a tryptophan to glycine substitution at position 98 of SEQ ID NO: 1 or at a position corresponding to position 98 of SEQ ID NO: 1, wherein the Zika virus is derived from strain PRVABC59 comprising the genomic sequence according to SEQ ID NO: 2 to treat or prevent Zika virus in a subject in need thereof and/or to induce an immune response to Zika virus in a subject in need thereof.

In some embodiments, the present disclosure relates to methods for treating or preventing Zika virus infection in a subject in need thereof by administering to the subject a purified inactivated whole Zika virus, such as a Zika virus with a mutation which is a tryptophan to glycine substitution at position 98 of SEQ ID NO: 1 or at a position corresponding to position 98 of SEQ ID NO: 1 as described herein.

In some embodiments, the present disclosure relates to methods for treating or preventing Zika virus infection in a subject in need thereof by administering to the subject a therapeutically effective amount of a vaccine and/or immunogenic composition of the present disclosure containing a purified inactivated whole Zika virus with a mutation which is a tryptophan to glycine substitution at position 98 of SEQ ID NO: 1 or at a position corresponding to position 98 of SEQ ID NO: 1. In some embodiments, the present disclosure relates to methods for treating or preventing Zika virus infection in a subject in need thereof by administering to the subject a therapeutically effective amount of a vaccine and/or immunogenic composition of the present disclosure containing a purified inactivated whole Zika virus with a mutation which is a tryptophan to glycine substitution at position 98 of SEQ ID NO: 1 or at a position corresponding to position 98 of SEQ ID NO: 1, wherein the Zika virus is derived from strain PRVABC59. In some embodiments, the present disclosure relates to methods for treating or preventing Zika virus infection in a subject in need thereof by administering to the subject a therapeutically effective amount of a vaccine and/or immunogenic composition of the present disclosure containing a purified inactivated whole Zika virus with a mutation which is a tryptophan to glycine substitution at position 98 of SEQ ID NO: 1 or at a position corresponding to position 98 of SEQ ID NO: 1, wherein the Zika virus is derived from strain PRVABC59 comprising the genomic sequence according to SEQ ID NO: 2.

In some embodiments, the present disclosure relates to methods for inducing an immune response to Zika virus in a subject in need thereof by administering to the subject a therapeutically effective amount of a vaccine and/or or immunogenic composition of the present disclosure containing a purified inactivated whole Zika virus, such as a Zika virus with a mutation which is a tryptophan to glycine substitution at position 98 of SEQ ID NO: 1 or at a position corresponding to position 98 of SEQ ID NO: 1 as described herein). In some embodiments, the present disclosure relates to methods for inducing an immune response to Zika virus in a subject in need thereof by administering to the subject a therapeutically effective amount of a vaccine and/or or immunogenic composition of the present disclosure containing a purified inactivated whole Zika virus with a mutation which is a tryptophan to glycine substitution at position 98 of SEQ ID NO: 1 or at a position corresponding to position 98 of SEQ ID NO: 1, wherein the Zika virus is derived from strain PRVABC59. In some embodiments, the present disclosure relates to methods for inducing an immune response to Zika virus in a subject in need thereof by administering to the subject a therapeutically effective amount of a vaccine and/or or immunogenic composition of the present disclosure containing a purified inactivated whole Zika virus with a mutation which is a tryptophan to glycine substitution at position 98 of SEQ ID NO: 1 or at a position corresponding to position 98 of SEQ ID NO: 1, wherein the Zika virus is derived from strain PRVABC59 comprising the genomic sequence according to SEQ ID NO: 2.

In some embodiments, the administering step induces a protective immune response against Zika virus in the subject. In some embodiments, the subject is a human. In some embodiments, the subject is pregnant or intends to become pregnant.

In some embodiments, the administering step includes one or more administrations. Administration can be by a single dose schedule or a multiple dose (prime-boost) schedule. In a multiple dose schedule the various doses may be given by the same or different routes e.g. a parenteral prime and mucosal boost, a mucosal prime and parenteral boost, etc. Typically they will be given by the same route. Multiple doses will typically be administered at least 1 week apart (e.g. about 2 weeks, about 3 weeks, about 4 weeks, about 5 weeks, about 6 weeks, about 7 weeks, about 8 weeks, about 9 weeks, about 10 weeks, about 11 weeks, about 12 weeks, about 16 weeks, etc.). Giving two doses separated by from 25-30 days (e.g. 28 days) is particularly useful.

The methods of the present disclosure include administration of a therapeutically effective amount or an immunogenic amount of the Zika virus vaccines and/or immunogenic compositions of the present disclosure. A therapeutically effective amount or an immunogenic amount may be an amount of the vaccines and/or immunogenic compositions of the present disclosure that will induce a protective immunological response in the uninfected, infected or unexposed subject to which it is administered. Such a response will generally result in the development in the subject of a secretory, cellular and/or antibody-mediated immune response to the vaccine. Usually, such a response includes, but is not limited to one or more of the following effects; the production of antibodies from any of the immunological classes, such as immunoglobulins A, D, E, G or M; the proliferation of B and T lymphocytes; the provision of activation, growth and differentiation signals to immunological cells; expansion of helper T cell, suppressor T cell, and/or cytotoxic T cell.

Preferably, the therapeutically effective amount or immunogenic amount is sufficient to bring about treatment or prevention of disease symptoms. The exact amount necessary will vary depending on the subject being treated; the age and general condition of the subject to be treated; the capacity of the subject's immune system to synthesize antibodies; the degree of protection desired; the severity of the condition being treated; the particular Zika virus antigen selected and its mode of administration, among other factors. An appropriate therapeutically effective amount or immunogenic amount can be readily determined by one of skill in the art. A therapeutically effective amount or immunogenic amount will fall in a relatively broad range that can be determined through routine trials.

The present disclosure will be more fully understood by reference to the following Examples. They should not, however, be construed as limiting any aspect or scope of the present disclosure in any way.

EXAMPLES

Example 1: Clonal Zika Virus Strain Generation

This example describes the production of Zika virus (ZIKAV) strains with a known research history.
Materials and Methods
Vero Cell Maintenance One vial of WHO Vero 10-87 cells was rapidly thawed in a water bath and directly inoculated into 19 mL pre-warmed DMEM (Dulbecco's modified minimal essential medium) containing penicillin-streptomycin, L-glutamine 40 mM, and 10% FBS in a T-75 cm$^2$ flask at 36° C.+/2° C., at 5% CO$_2$. Cells were allowed to grow to confluency and subcultured using TryplE. This flask was expanded to two T-185 cm$^2$ flasks, grown to confluency and subcultured to 31 xT-185 cm$^2$ flasks and grown until the cells reached 100% confluency. Cells were harvested by trypsinization, centrifuged at 800×g for 10 minutes, and resuspended in DMEM containing 10% FBS and 10% DMSO at a concentration of 1.9×10$^7$ cells/mL. One vial of the Vero cells was rapidly thawed and resuscitated as described above into a T-75 cm$^2$ flask. These were subcultured twice to produce a cell bank in 13×T-185 cm$^2$ flasks. After trypsinization, the cells were centrifuged at 800×g and resuspended in freezing media (DMEM containing 10% FBS, and 10% DMSO) at a concentration of 4.68×10$^5$ cells/mL. This cell bank was aliquoted into cryovials.

The Vero cells were grown and maintained in DMEM containing penicillin-streptomycin, L-glutamine and 10% FBS (cDMEM-10%-FBS). TryplExpress was used to maintain and trypsinize cells. Two days before viral adsorption, 6-well plates were seeded with 4-5×10$^5$ cells/well in 3 mL of cDMEM-10%-FBS or 7×10$^5$ cells in T-25 cm$^2$ flasks in 5 mL cDMEM-10%-FBS, or 1×10$^4$ cells/well in 96-well plates in 0.1 mL cDMEM-10%-FBS. Incubators were monitored daily to maintain indicated temperatures. The Vero cell lines were stored in liquid nitrogen.
Plaque Assay Viral titers were determined by plaque titration in freshly confluent monolayers of Vero cells grown in 6-well plates. Frozen aliquots were thawed and ten-fold dilution series of the aliquots were made in cDMEM-0%-FBS in 96-well plates. The diluted viruses were maintained on ice prior to inoculation of the Vero cell monolayers. At the time of assay, the growth medium was aspirated from the 6-well plate, and 100 μL of each virus dilution was added to the wells. Virus was adsorbed for 60 min at 36° C.±2° C., at 5% CO$_2$, with frequent (every 10 min) rocking of the plates to prevent drying of the cell sheets. Following viral adsorption, 4 mL of a first agarose overlay (1×cDMEM-2%-FBS+0.8% agarose) maintained at 40-41° C. was added to each well. The agarose was allowed to solidify for 30 min at room temperature, and the plates were then incubated upside down for 4-6 days at 36° C.+/2° C., at 5% $CO_2$. Two mL of a second agarose overlay containing 160 μg/mL of neutral red vital dye was added on day 4. Plaques were visualized on days 5 and 6.

Virus Quantification by TCID50 Assay

Viral titers were also determined by titration in freshly confluent monolayers of Vero cells grown in 96-well plates. Frozen aliquots were thawed and ten-fold dilution series of the aliquots were made in cDMEM-2%-FBS diluent in 96-well plates. The diluted viruses were maintained on ice prior to inoculation of the Vero cell monolayers. At the time of assay, the growth medium was aspirated from the 96-well plate, and 100 μL of each virus dilution was added to the wells. The plates were incubated for 5 days at 36° C.+/2° C., at 5% $CO_2$. The 50% Tissue Culture Infective Dose (TCID50) titer was calculated using the Reed/Muench calculator.

Test Articles

Figure 4:
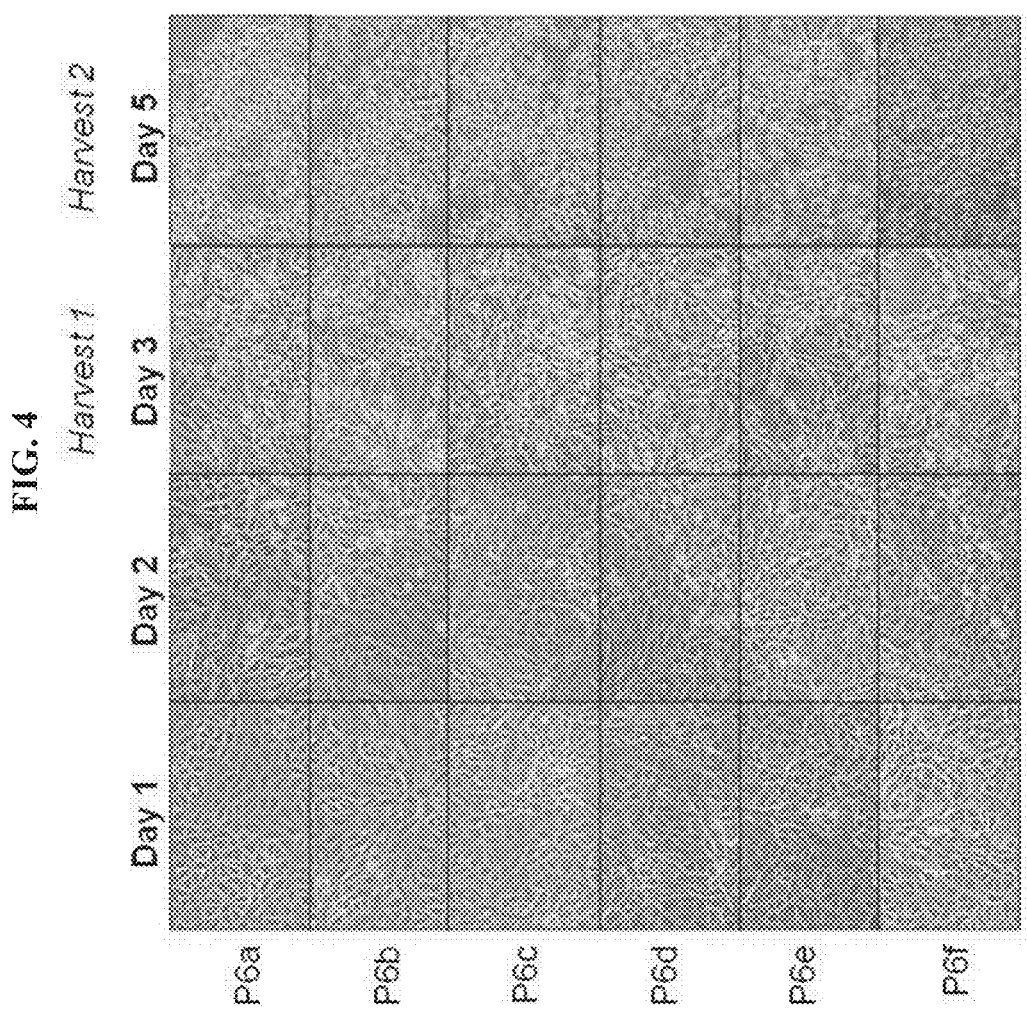
FIG. 4 shows bright-field microscopy images depicting the cytopathic effect (CPE) of growth of Zika virus PRVABC59 P6 clones a-f on Vero cell monolayers.

Zika virus strain PRVABC59 (one 0.5 mL vial on dry ice) was received from the Centers for Disease Control and Prevention (CDC) Zika virus identification was confirmed through RT-PCR. The strain tested negative for Alphavirus and mycoplasma contamination by PCR. This information is summarized in Table 1.

C.±2° C., at 5% $CO_2$, then 20 mL of cDMEM-0%-FBS was applied for viral amplification at 36° C.±2° C., at 5% $CO_2$. The cell layer was monitored daily for cytopathic effect (CPE) following inoculation (FIG. 1). The supernatant was harvested after 96 hours by collecting the media and clarifying by centrifugation (600×g, 4° C., 10 min). The harvest was stabilized by adding trehalose to a final concentration of 18% w/v. The bulk was aliquoted into 0.5 mL cryovials and stored at −80° C.

The stabilized P1 harvest was analyzed for the presence of infectious virus on Vero cell monolayers by a TCID50 assay. Growth kinetics were monitored by taking daily aliquots beginning on hour 0. Peak titer was reached by hour 72 (FIG. 2).

P1 material was plaque-purified by titrating the harvest from day 3 on 6-well monolayers of Vero cells. Plaques were visualized on day 6, and 10 plaques to be isolated were identified by drawing a circle around a distinct and separate plaque on the bottom of the plastic plate. Plaques were picked by extracting the plug of agarose using a sterile wide bore pipette while scraping the bottom of the well and rinsing with cDMEM-10%-FBS. The agarose plug was added to 0.5 mL of cDMEM-10%-FBS, vortexed, labeled as PRVABC59 P2a-j and placed in an incubator overnight at 36° C.±2° C., at 5% $CO_2$.

TABLE 1

PRVABC59 strain information

| Strain | Isolation Information | Patient information | Prep info | Analyses | PFU |
|---|---|---|---|---|---|
| PRVABC59 (Asian) | Human serum; travel to Puerto Rico in 2015 | None provided | Passage: Vero(2)C6/36(1) Prep: 29 Jan. 2016 Host: C6/36 | Sequencing by ion torrent: gene accession #KU501215 PFU by plaque assay Identity by RT-PCR (—) For alphaviruses by PCR (—) for mycoplasma by ATCC and ABM PCR | 6.7 log pfu/mL |

Sequencing

A QIAampViral RNA Mini Spin kit was used to extract RNA from stabilized virus harvests of each isolate according to manufacturer protocols. Extracted RNA from each isolate was used to create and amplify 6 cDNA fragments encompassing the entire Zika viral genome. Amplified cDNA fragments were analyzed for size and purity on a 1% Agarose/TBE gel and subsequently gel purified using a Qiagen Quick Gel Extraction Kit. An ABI 3130XL Genetic Analyzer sequencer was used to conduct automatic sequencing reactions. Lasergene SeqMan software was used to analyze sequencing data.

Results

A ZIKAV strain with a known research history that was relevant to the current ZIKAV outbreak in the America's was sought. For this reason, ZIKAV strain PRVABC59 was chosen. To generate a well-characterized virus adapted for growth in Vero cells, the ZIKAV PRVABC59 was first amplified in Vero cells (P1).

Flasks of Vero cells (T-175 $cm^2$), 100% confluent, were infected at an MOI of 0.01 in 4 mL of cDMEM-0%-FBS. Virus was adsorbed to the monolayer for 60 minutes at 36°

Three plaques (PRVABC59 P2a-c) were carried forward for additional purification. Each isolate was plated neat in duplicate onto a fresh 6-well monolayer of Vero cells. This P2/P3 transition was plaque purified, and labeled PRVABC59 P3a-j.

Six plaques (PRVABC59 P3a-f) were carried forward for a final round of purification. Each isolate was plated neat in duplicate onto a fresh 6-well monolayer of Vero cells. This P3/P4 transition was plaque purified, and labeled PRVABC59 P4a-j.

Six plaques (PRVABC59 P4a-f) from the P4 plaque purification were blind passaged on monolayers of Vero cells in T-25 $cm^2$ flasks. Each plaque pick was diluted in 2 mL cDMEM-0%-FBS −1 mL was adsorbed for 1 hour at 36° C.±2° C., at 5% $CO_2$; the other 1 mL was stabilized with trehalose (18% v/v final) and stored at <−60° C. Following virus adsorption, cDMEM-0%-FBS was added to each flask and allowed to grow at 36° C.±2° C., at 5% $CO_2$ for 4 days. Virus supernatants were harvested, clarified by centrifugation (600×g, 4C, 10 min), stabilized in 18% trehalose and aliquoted and stored at <−60° C. This P5 seed was tested by TCID50 for Zika virus potency (FIG. 3).

Confluent monolayers of T-175 cm² flasks of Vero cells were infected with each of the six clones of PRVABC59 (P5a-f) at an MOI of 0.01 in 4 mL cDMEM-0%-FBS. The virus was allowed to adsorb for 60 minutes at 36° C.+/2° C., at 5% $CO_2$, after which 20 mL of cDMEM-0%-FBS was added to each flask and allowed to grow at 36° C.+/2° C., at 5% $CO_2$. Vero cell monolayer health and CPE was monitored daily. Virus was harvested on days 3 and 5 as indicated (FIG. 4). The P6 strain harvests from days 3 and 5 were pooled, stabilized with 18% trehalose, aliquoted and stored <−60° C.

Figure 5:
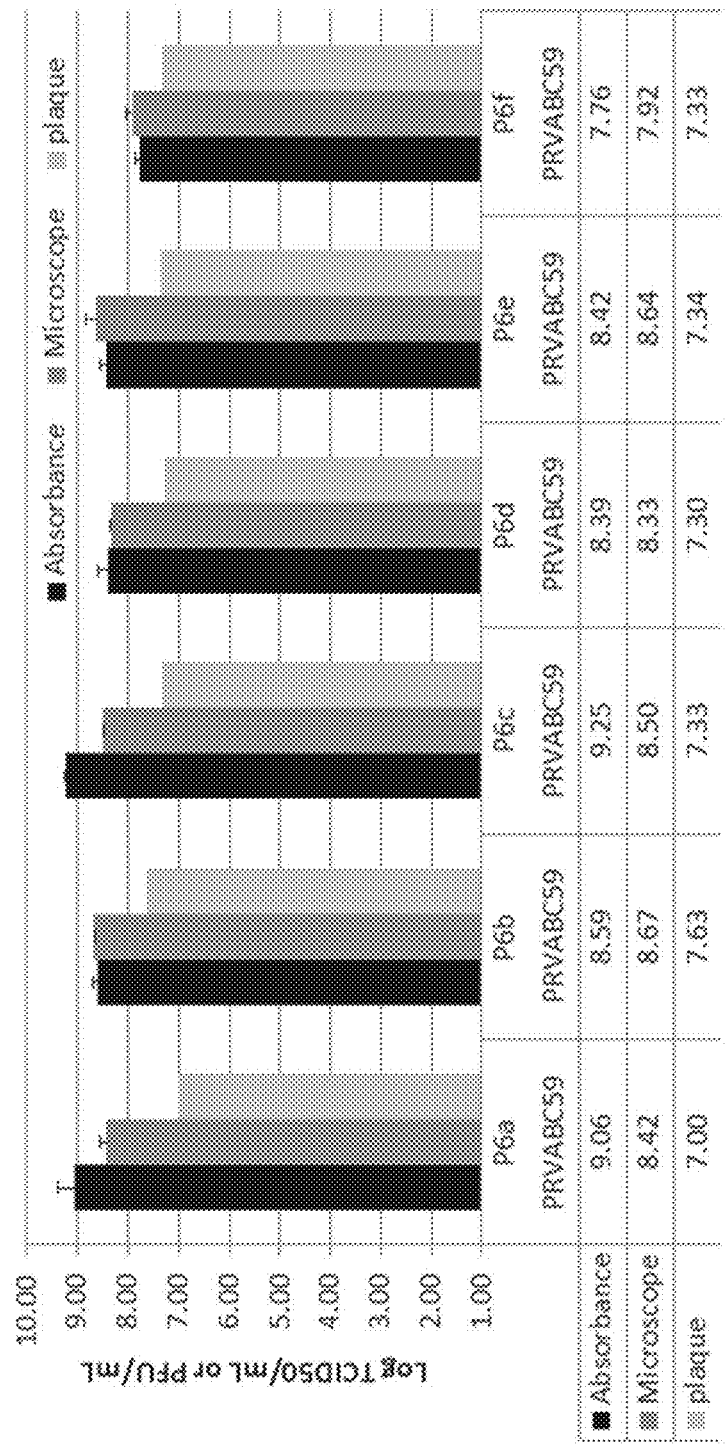
FIG. 5 shows potency assay testing ($TCID_{50}$) of Zika virus PRVABC59 P6 clones a-f

Each of the six clones of PRVABC59 (P6a-f) were tested for Zika virus in vitro potency (FIG. 5). The potency was determined by two different methods, TCID50 and plaque titration. The TCID50 was calculated by visual inspection of CPE (microscope) and by measuring the difference in absorbance ($A_{560}$-$A_{420}$) of the wells displaying CPE (yellow in color) compared with red (no CPE). The plates were read on a plate reader, and applied to the same calculator as the microscopically read-plates (absorbance). The values in TCID50 between the two scoring techniques are quite similar, while the values obtained by plaque titration are lower.

A summary of the generation of the P6 virus and characterization is shown in Table 2 below.

TABLE 2

Summary of virus passage and characterization for the generation of clonal ZIKAV strains

| Passage | Seed production/purification | Characterization |
| --- | --- | --- |
| P1 | Virus amplification in Vero | TCID50 titer |
| P2 | Amplify P1 by plaque titration; Plaque purification of P1 | plaque purification |
| P3 | Pick and passage plaques from P2 plaque assay; plaque purification of P2 | plaque purification |
| P4 | Pick and passage plaques from P3 plaque assay; plaque purification of P3 | plaque purification |
| P5 | Amplify P4 plaques (a-f) in Vero cells | TCID50 titer |
| P6 | Amplify P5 (a-f) virus in Vero cells | TCID50 titer, plaque phenotype, genotype, full genome sequencing, growth kinetics |

Figure 6:
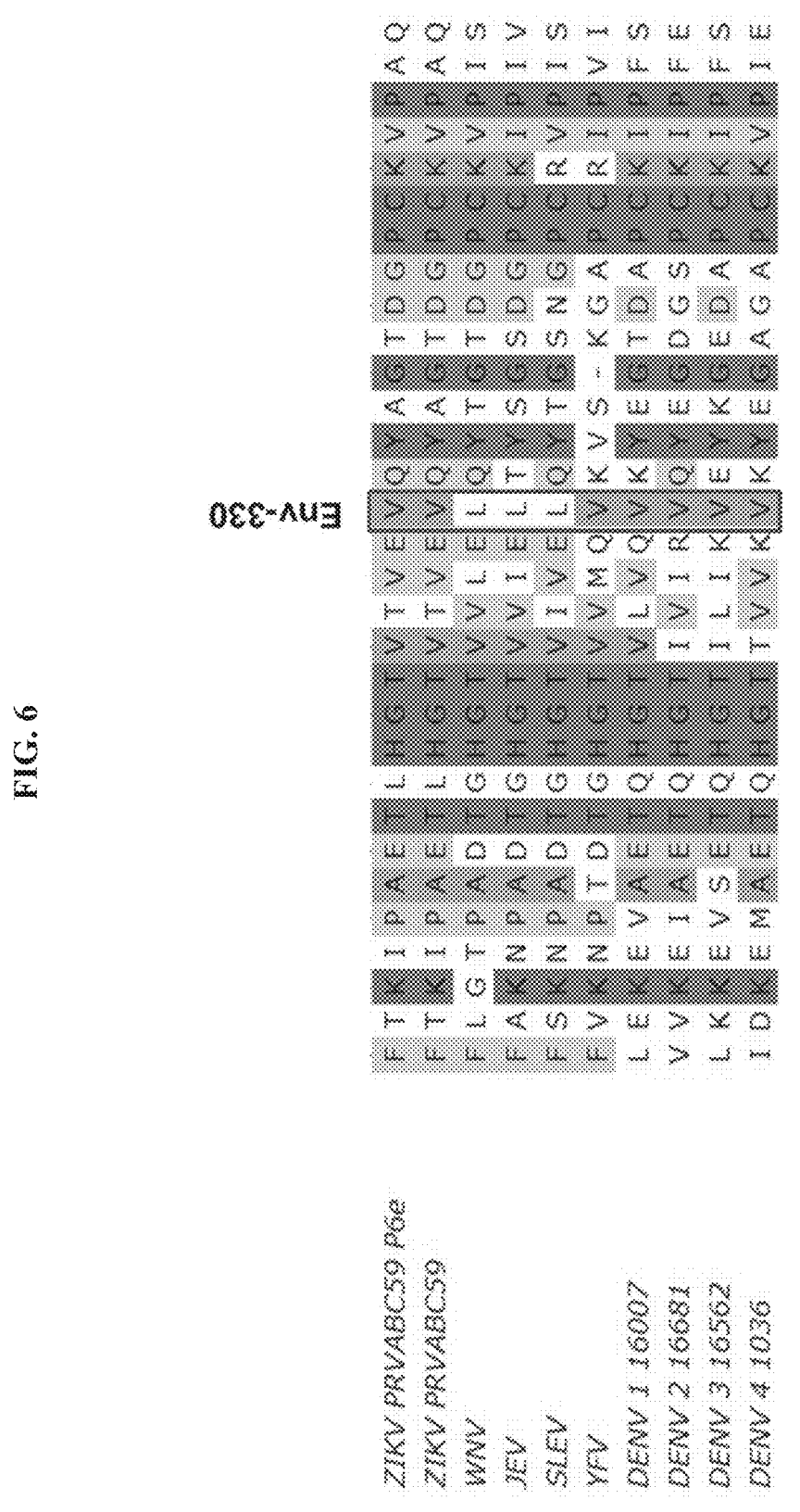

An isolated Zika virus clone that closely resembled the envelope glycoprotein sequence of the original isolate was sought, since the envelope protein of flaviviruses is the dominant immunogenic portion of the virus. PRVABC59 clones P6a, P6c, P6d and P6f contained a G→T mutation at nucleotide 990 in the envelope region (G990T), resulting in an amino acid mutation of Val→Leu at envelope residue 330, whereas the envelope gene of PRVABC59 clones P6b and P6e were identical relative to the reference strain (GenBank ref KU501215.1) (Table 3 and FIG. 6).

TABLE 3

Sequencing of PRVABC59 P6 clones

| Strain | Nucleotide | Amino Acid | Mutation | Comments |
| --- | --- | --- | --- | --- |
| Envelope sequencing (reference gene from PRVABC59; accession #KU501215) | | | | |
| PRVABC59 P6a | Env-990: G→T | Env-330: Val330→Leu | Val/Leu | Mutation in 3 of 4 reads. |
| PRVABC59 P6b | Env-1404: T→G silent | Wild type | Wild type | Wild type relative to reference. |
| PRVABC56 P6c | Env-990: G→T | Env-330: Val330→Leu | Val/Leu | Mutation in 3 of 4 reads. |
| PRVABC59 P6d | Env-990: G→T | Env-330: Val330→Leu | Val/Leu | Mutation in 2 of 2 reads. |
| PRVABC59 P6e | Wild type | Wild type | Wild type | Wild type relative to reference. |
| PRVABC59 P6f | Env-990: G→T | Env-330: Val330→Leu | Val/Leu | Mutation in 2 of 2 reads. 190 bp not sequenced (aa 421-484). |
| Full genome sequencing (reference gene from PRVABC59; accession #KU501215) | | | | |
| PRVABC59 P6b | Env-1404 T→G | Wild-type | Silent | Mutation in 2 of 2 reads |
| | NS1-292 T→G | NS1-98 Trp98→Gly | Trp/Gly | Mutation in 2 of 2 reads |
| PRVABC59 P6e | NS1-292 T→G | NS1-98 Trp98→Gly | Trp/Gly | Mutation in 2 of 2 reads |

The two clones lacking mutations in the Zika envelope sequence were then subjected to full genome sequencing. Sequencing results are summarized in Table 3 above. Sequence analysis revealed a T→G substitution at nucleotide 292 in the NS1 region for both clones, resulting in a Trp→Gly mutation at NS1 residue 98. This mutation was also later confirmed through deep sequencing. The NS1 W98G mutation is located in the intertwined loop of the wing domain of ZIKAV NS1, which has been implicated in membrane association, interaction with envelope protein and potentially hexameric NS1 formation. While other tryptophan residues (W115, W118), are highly conserved across flaviviruses, W98 is not (FIG. 7). Interestingly, however, 100% conservation of the W98 residue is observed across 11 different ZIKAV strains, including those from the African and Asian lineages. The identified mutations in each strain are summarized in Table 4.

TABLE 4

Summary of mutations identified in PRVABC59 P6 clones

| Clone | Nucleotide | Amino Acid |
| --- | --- | --- |
| Mutations identified in envelope | | |
| P6a | G990T | V330L |
| P6b | T1404G | (silent) |
| P6c | G990T | V330L |
| P6d | G990T | V330L |
| P6e | none | none |
| P6f | G990T | V330L |
| Additional mutations identified in genome | | |
| P6b | NS1-T292G | NS1-W98G |
| P6e | NS1-T292G | NS1-W98G |
| Ref sequence: KU501215.1 (PRVABC59) | | |

Figure 8:
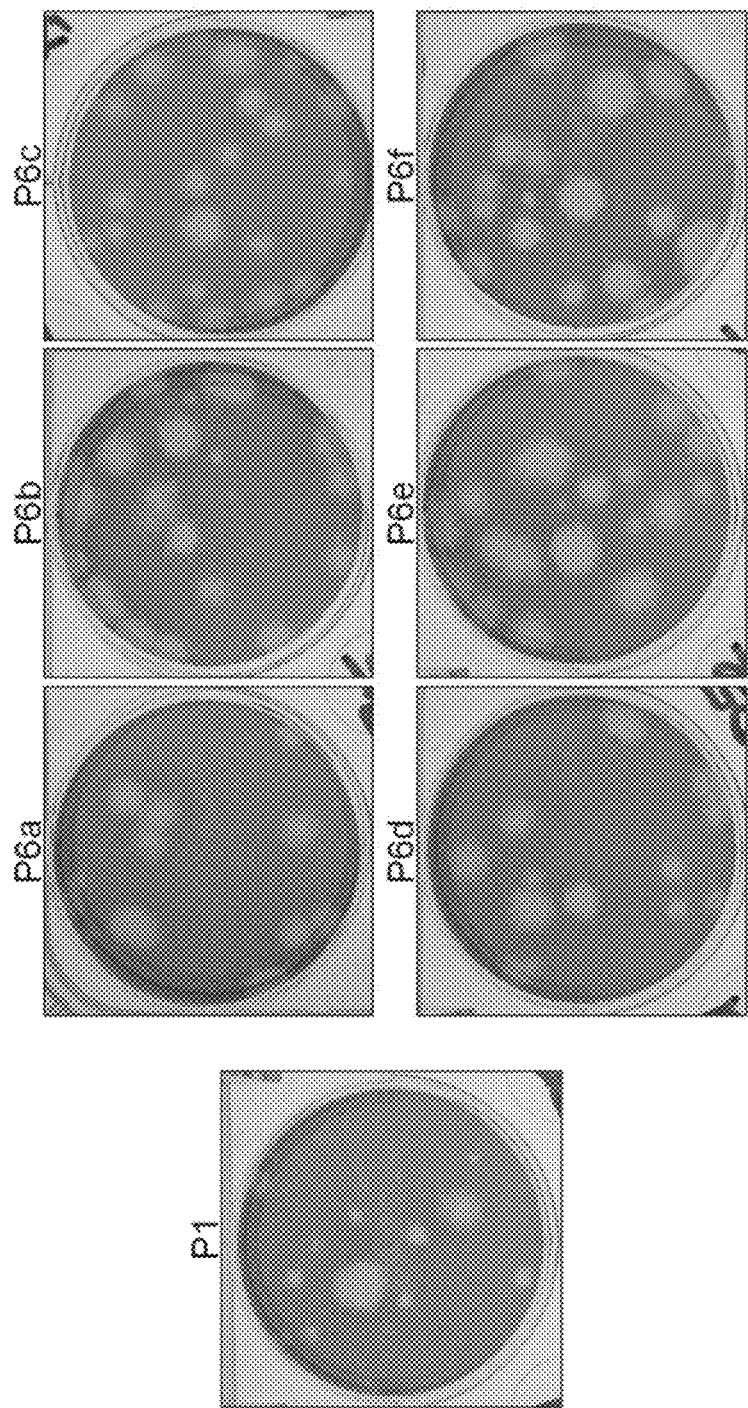
FIG. 8 shows the plaque phenotype of ZIKAV PRVABC59 P6 virus clones a-f compared to ZIKAV PRVABC59 P1 virus.
Figure 9:
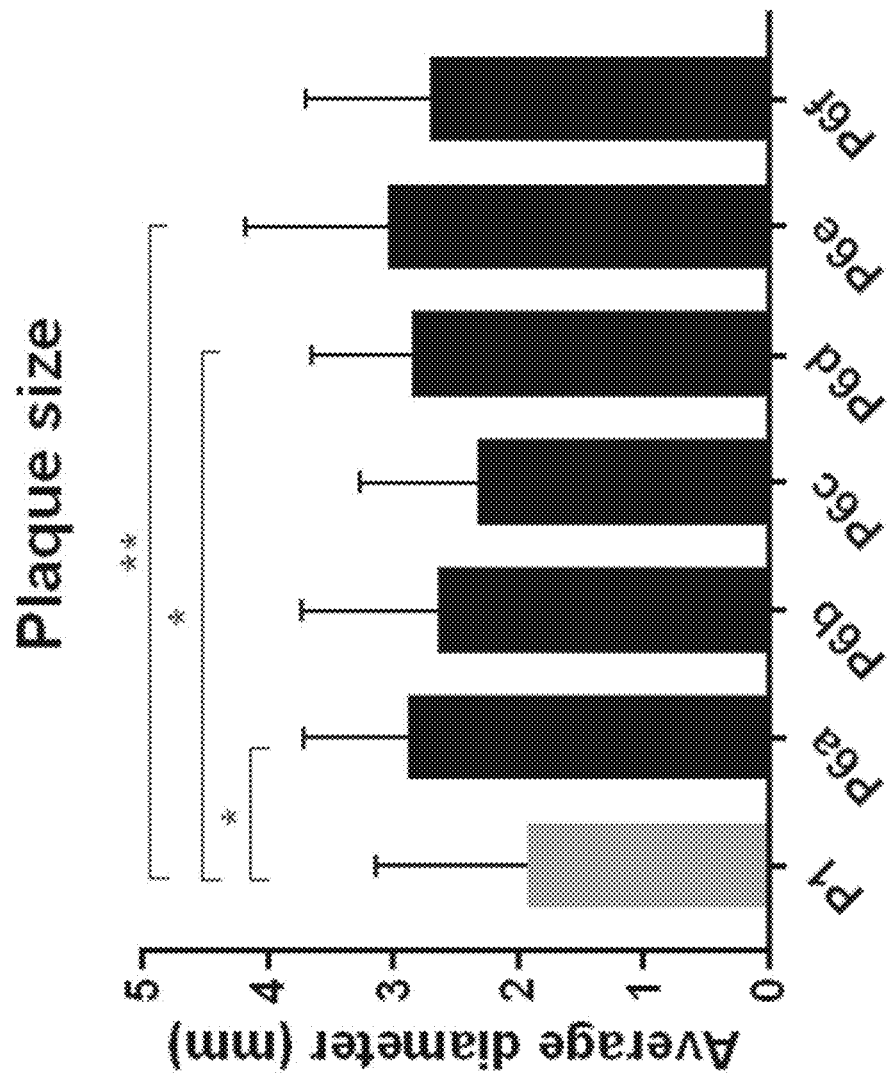
FIG. 9 shows the mean plaque size of ZIKAV PRVABC59 P6 virus clones compared to ZIKAV PRVABC59 P1 virus.

Phenotypic analysis of the ZIKAV PRVABC59 P6 stocks was conducted to characterize the ZIKAV clones. As illustrated in FIG. 8 and quantified in FIG. 9, each clonal isolate consisted of a relatively homogeneous population of large-sized plaques as compared to the P1 virus which had a mixed population of large and small plaques. These data suggest the successful isolation of single ZIKAV clones.

Figure 10:
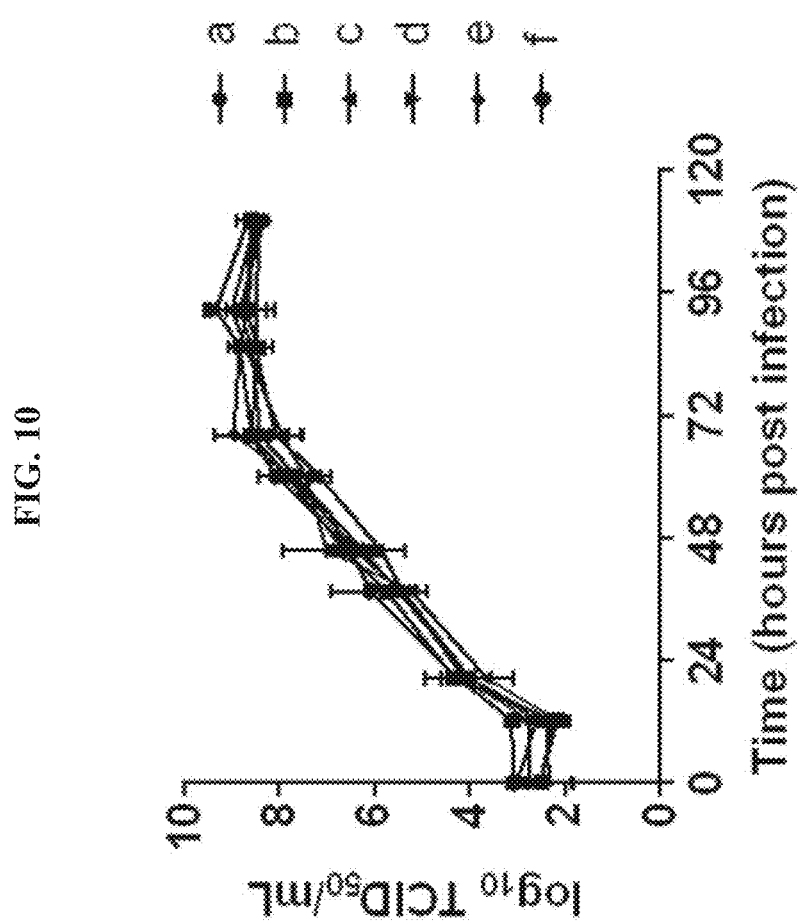
FIG. 10 shows the growth kinetics of ZIKAV PRVABC59 P6 clones a-f in Vero cells under serum-free growth conditions.

Next, growth kinetics analyses in Vero cells of the ZIKAV PRVABC59 P6 clones were analyzed. Vero cells were infected with 0.01 $TCID_{50}$/cell of each ZIKAV P6 clones in serum free growth medium. Viral supernatant samples were taken daily and simultaneously assayed for infectious titer by $TCID_{50}$ assay. For all P6 clones, peak titer occurred between day 3 and 4 (~9.0 $\log_{10}$ $TCID_{50}$/mL). There was no significant difference in growth kinetics of the various P6 clones (FIG. 10).

Taken together, the results indicate that a Zika virus seed was successfully generated. This seed selection required understanding of growth history, kinetics, yield, genotype, and phenotype of the virus. Importantly, clonal isolation of the Zika virus strains allowed for the successful purification of the virus away from contaminating agents (e.g., adventitious agents that may be in the parental human isolate). Interestingly, three sequential plaque purifications succeeded in quickly selecting Vero-cell adapted virus (strains P6a-f), where these strains were able to replicate well in serum-free Vero cell cultures, with strain P6a, c, d, and f harboring a mutation in the viral envelope protein, while strains p6b and p6e obtained a mutation in the viral NS1 protein (with no modification to the viral envelope). Additionally, the Vero-adapted strains enabled efficient and reproducible growth and manufacture of subsequent viral passages propagated from these strains. Without wishing to be bound by theory, the Env-V330L mutation observed in strains P6a, c, d, and f may potentially be a result of in vitro adaptation, as a mutation at Env 330 was also observed upon passaging in Vero cells (Weger-Lucarelli et al. 2017. Journal of Virology). Because the envelope protein is the dominant immunogenic epitope of Zika virus, strains containing a Vero adaptive mutation in Env may negatively impact vaccine immunogenicity. Without wishing to be bound by theory, the adaptation mutation in protein NS1 appears not only to enhance viral replication, but may also reduce or otherwise inhibit the occurrence of undesirable mutations, such as in the envelope protein E (Env) of the Zika virus. In addition, NS1 may be known to bind to the Envelope protein during the life cycle of the virus. This mutation (NS1 W98G) may be implicated in changing the ability of the NS1 to associate, and possibly co-purify, with the virus during downstream processing. NS1 is also known to be immunogenic, and could be implicated in the immune response to the vaccine.

Example 2: Preclinical Immunogenicity and Efficacy of a Purified Inactivated Zika Virus Vaccine (PIZV) Derived from the P6b and P6e Strains The following example describes the preclinical immunogenicity and efficacy in CD1 and AG129 mice of an inactivated Zika virus vaccine (PIZV) derived from the P6b and P6e strains. As described in Example 1, six clones were generated from the epidemically relevant PRVABC59 strain, and two (P6b and P6e) were chosen for further preclinical immunogenicity and efficacy studies.

Materials and Methods

Purification, Inactivation and Formulation of a Zika Virus Vaccine

A lot of inactivated ZIKAV vaccine, suitable for use in preclinical immunogenicity and efficacy studies, was generated and characterized. Virus was amplified from the P6b and P6e strains by infecting flasks of confluent Vero cells at a MOI of 0.01. Virus was adsorbed for 1 hour at 36° C.±2° C./5% $CO_2$. Following adsorption, 20 mL of cDMEM-0%-FBS was added to each flask, and incubated at 36° C.±2° C./5% $CO_2$ for five days. Cell supernatants were harvested on day 3 and 5 post-infection, and cell debris was clarified by centrifugation.

For each isolate, clarified supernatants were pooled, stabilized in DMEM containing 18% trehalose and stored at <−60° C. Pooled, clarified virus supernatants were thawed in a 37° C. water bath and treated with benzonase overnight at 4° C. Following benzonase treatment, each sample was applied to a Sartorius PP3 depth filter. Following depth filtration, each sample was applied to a Centricon Plus-70 tangential flow filtration (TFF) device. Retentate was buffer exchanged, diluted, and applied to a Sartorius SartobindQ IEXNano. Each sample was applied to a second Sartorius SartobindQ IEXNano and eluted using a 3 step-elution process with 250 mM, 500 mM, and 750 mM NaCl. Following MonoQ chromatography and dilution, each 250 mM eluate was applied to a Centricon Plus-70 cross flow filtration (CFF) device for buffer exchange, diluted to 35 mL with PBS, and stored at 2-8° C.

For formalin inactivation, freshly prepared 1% formaldehyde was added dropwise to each purified sample with gentle swirling to obtain a final formaldehyde concentration of 0.02%. Samples were incubated at room temperature (~22° C.) for 14 days with daily inversion. Formaldehyde was neutralized with sodium metabisulfite for 15' at room temperature before being applied to a Centricon Plus-70 tangential flow filtration (TFF) device. Buffer exchange was performed four times by the addition of 50 mL Drug Substance Buffer (10 mM NaH2PO4, 50 mM NaCl, 6% sucrose, pH 7.4). Each sample was then diluted to 15 mL with Drug Substance Buffer, sterilized using a 0.2 m syringe filter, aliquoted into sterile stoppered glass vials (0.5 mL per vial) and frozen at <−60° C.

Figure 11:
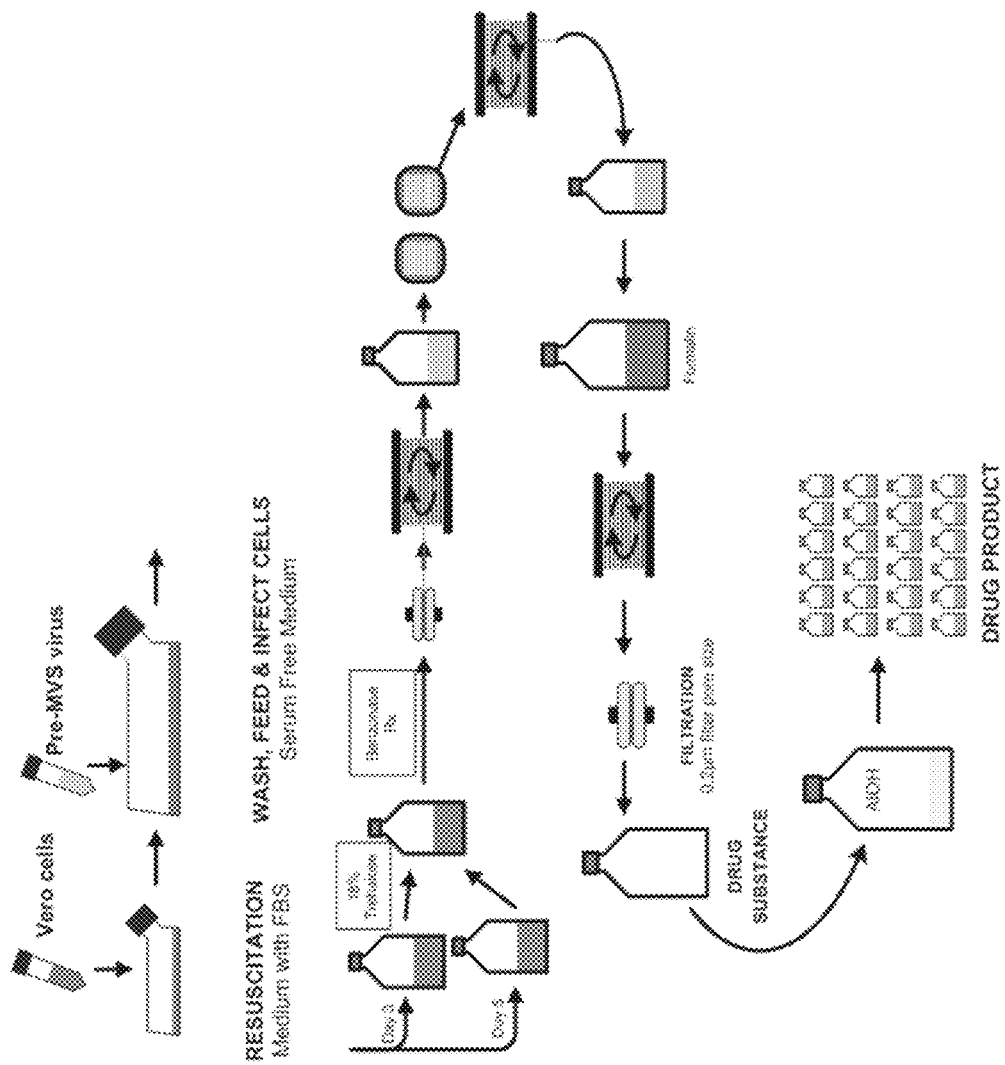
FIG. 11 shows a schematic of the steps taken to prepare PRVABC59 P6b and P6e formulated drug product for the immunization experiments.

Virus inactivation was confirmed by TCID50 assay and double infectivity assay. Briefly drug substance sample was applied to C6/36 cells and allowed to amplify for 6 days. Supernatant from C6/36 cells was applied to Vero cells and CPE was monitored for 8 days. For drug product formulation, vials of PIZV drug substance were thawed, pooled according to sample type, and diluted to 1 µg/mL or 10 µg/mL in PBS with or without Alhydrogel (Brenntag; 0.5 mg/mL final, 0.050 mg/dose) and incubated overnight at 2-8° C. with gentle agitation. The resulting drug product lots were then aliquoted into sterile stoppered glass vials and stored at 2-8° C. until use. FIG. 11 provides a summary of the steps used to prepare drug product.

Mouse Immunization and Challenge

For the immunogenicity study, six-week old male and female Swiss-ICR (CD-1) mice were divided into 6 groups (n=10/group). On Day 0, mice in groups 1-5 were inoculated with 0.1 mL of vaccine by the intramuscular (i.m.) route (2×0.05 mL injections). Mice in group 6 were inoculated with PBS as a placebo control. Mice were boosted on day 28 and 56 using the same dosage and vaccine type as day 0. Blood samples were collected on day −1 (pre-immune), day 27 (prime), day 42 (boost 1) and day 70 (boost 2).

For the immunogenicity and efficacy study, four-week old male and female AG129 mice were divided into 7 groups (n=5/group). On Day 0, mice in groups 1-6 were inoculated with 0.1 mL of vaccine by the intramuscular (i.m.) route (2×0.05 mL injections). Mice in group 7 were inoculated with PBS as a placebo control. Mice were boosted on day 28 using the same dosage and vaccine type as on day 0. Blood samples were collected from the tail vein on day −1 (pre-immune), day 27 (prime) and day 55 (boost). At the time of euthanization, mice were bled via cardiac puncture under deep anesthesia with isofluorane (terminal). On day 56, mice were intraperitoneally challenged with $10^4$ plaque forming units (PFU) of ZIKAV PRVABC59.

Serum Transfer

Serum was collected from PIZV-vaccinated and challenged AG129 mice, and were frozen after pooling (groups 1, 2, 4, and 5 of Table 6). The serum pool was thawed, and the test articles were generated by three-fold dilutions of the serum pool in PBS. A placebo was generated using 3-fold dilutions of AG129 normal mouse serum in PBS.

The test articles were administered as 0.1 mL intraperitoneal injections into AG129 mice (an equivalent volume of the placebo article was administered to control mice). Animals were then challenged intraperitoneally with $10^4$ plaque forming units of Zika virus strain PRVABC59 in 100 µL.

Allowable blood volume by weight was collected as whole blood by tail bleeding from ten mice on day −11 (pre-immunization). Whole blood was collected from each mouse on day 1 (primary, circulating Nab) and day 4 (viremia) by tail bleeding. Terminal bleeding after lethal challenge was performed by heart puncture under deep anesthesia for larger volume before euthanization by cervical dislocation. Blood samples were collected in microtainer SST serum separation gel tubes and allowed to clot for at least 30 min before separation of serum by centrifugation (10,000×g for 2 min) and frozen at −80° C.

Plaque Reduction Neutralization Test

Neutralizing antibody titers were determined by a plaque reduction neutralization test (PRNT) as described previously (See e.g., Osorio et al. Lancet Infect Dis. 2014 September; 14(9):830-8).

Reporter Virus Particle (RVP) Neutralization Assay

Neutralizing antibody titers were analyzed by titration of serum samples with a constant amount of Zika RVPs in Vero cells grown in 96-well plates. RVPs contained the prME proteins of Zika (strain SPH2012) and a Dengue-based Renilla luciferase reporter. Briefly, sera were heat inactivated at 56° C. for 30 min, diluted, and then incubated at 37° C. with RVPs. The serum/RVP mixture was then mixed with Vero cells and incubated for 72 hours at 37° C.±2° C./5% $CO_2$ before detection with luciferase substrate. Data was analyzed using JMP11 non-linear 4 parameter analysis, normalized to a positive tracking control and effective dose 50% ($EC_{50}$) was reported.

Unless indicated to the contrary, all additional experimental methods were carried out as described in Example 1 above.

Results

To assess the immunogenicity of the PIZV candidates in 6 week old male and female CD-1 mice, groups of CD-1 mice (N=10/group) were immunized by the i.m. route with either a 0.1 µg (+alum), 1.0 µg (+alum) dose of a vaccine derived from either ZIKAV PRVABC69 P6b or P6e virus strains. To assess the need for adjuvant, a group of animals was vaccinated with 0.1 µg of vaccine derived from P6e and lacking alum adjuvant. Vaccinations occurred on days 0, 28, and 56, with group 6 receiving PBS as a placebo control (FIG. 12A and Table 5).

TABLE 5

| PIZV formulations and challenges in CD-1 mice | | | | |
|---|---|---|---|---|
| Group | Strain | Dose (µg) | Alum (µg) | N |
| 1 | P6b | 0.1 | 0.50 | 10 |
| 2 | P6b | 1.0 | 0.50 | 10 |
| 3 | P6e | 0.1 | 0.50 | 10 |
| 4 | P6e | 1.0 | 0.50 | 10 |
| 5 | P6e | 0.1 | — | 10 |
| 6 | Placebo (PBS) | — | — | 10 |

Following vaccination, serum samples collected after primary (day 27), secondary (day 40) and tertiary (day 70) immunizations were tested for ZIKAV-specific neutralizing antibodies by RVP neutralization assay (FIG. 12B). Twenty-seven days after receiving the first dose, a slight neutralizing antibody response was observed in mice vaccinated with PIZV derived from either clone containing alum, as compared to the PBS placebo control group. Importantly, this response increased significantly upon a second immunization (day 40), but was not additionally enhanced upon immunization with a third dose (day 70). No neutralizing antibody response was observed in mice vaccinated with non-adjuvanted vaccine (FIG. 12B).

Figure 13A:
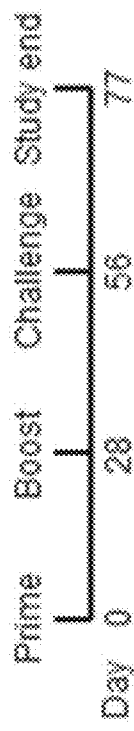
FIG. 13A shows the schedule of dosing of AG129 mice with vaccine formulations derived from the ZIKAV PRVABC59 P6b and P6e clones. PBS was used as a placebo.

To assess the immunogenicity and protective efficacy of the PIZV candidates, groups of 4 week old AG129 mice (n=5/group) were immunized by the i.m. route with either a 0.1 µg dose (+ alum), 1.0 µg dose (+ alum) or 0.1 µg dose (−alum) of a vaccine derived from either the ZIKAV PRV-ABC59 P6b or P6e stocks on days 1 and 28 (FIG. 13A and Table 6).

TABLE 6

PIZV formulations and challenges in AG129 mice

| Group | Sex | Strain | Dose (µg) | Alum (µg) | N |
|---|---|---|---|---|---|
| 1 | F | P6b | 0.1 | 0.50 | 5 |
| 2 | F | P6b | 1.0 | 0.50 | 5 |
| 3 | F | P6b | 0.1 | — | 5 |
| 4 | M | P6e | 0.1 | 0.50 | 5 |
| 5 | M | P6e | 1.0 | 0.50 | 5 |
| 6 | M | P6e | 0.1 | — | 5 |
| 7 | M | Placebo (PBS) | — | — | 5 |

Figure 13B:
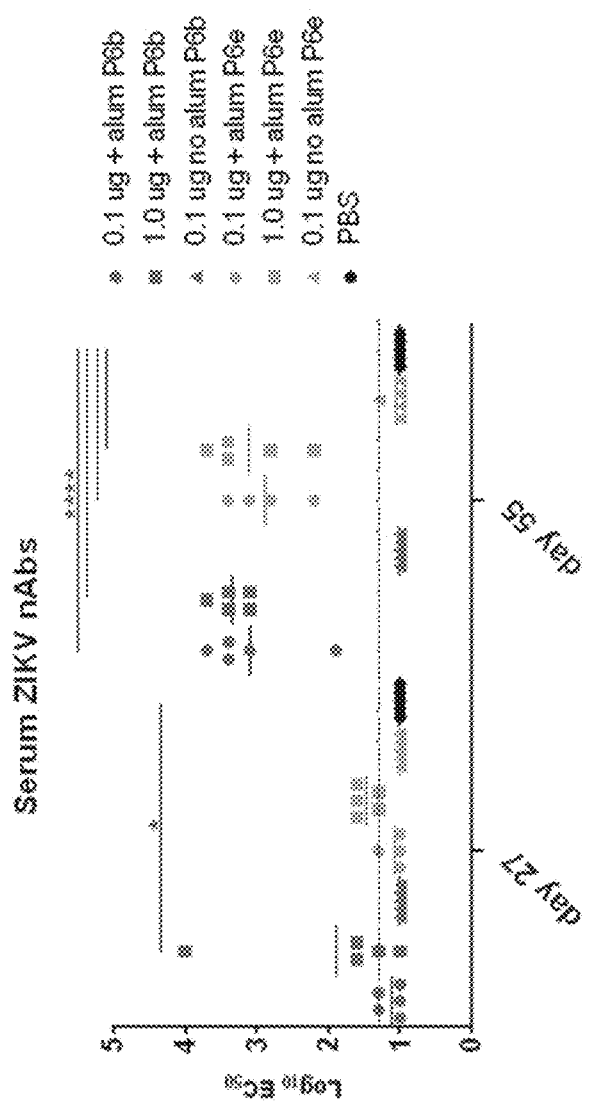
FIG. 13B shows the serum ZIKAV neutralizing antibody titers of AG129 mice immunized as described in FIG. 13A using vaccine formulations derived from ZIKAV PRVABC59 P6b and P6e clones. Solid lines represent the geometric mean of a group. The limit of detection (1.30 $\log_{10}$) is represented by a dashed line. Animals with no detectable titer (<1.30) were assigned a titer of 0.5.

Following vaccination, vaccinated and control mice were intraperitoneally challenged at day 56 with $10^4$ PFU of ZIKAV PRVABC59 (low passage). Serum samples collected after primary (D27) and secondary (D55) immunizations were tested for ZIKAV-specific neutralizing antibody response (FIG. 13B and Table 7). Only groups receiving the high dose of alum-adjuvanted vaccine (groups 2 and 5) elicited a neutralizing antibody response after a single immunization, which increased dramatically after boosting. In contrast, groups receiving either the low or high dose of alum-adjuvanted vaccine produced a high neutralizing antibody response after a second dose. Upon receiving two doses of vaccine, there was no statistical difference between groups of mice receiving alum-adjuvanted vaccine, regardless of the dosage or the derivation from the P6 clone.

TABLE 7

ZIKAV-specific neutralizing antibody response

| | | Serum neutralizing antibody titers | | | |
|---|---|---|---|---|---|
| | | D27 (prime) | | D55 (boost) | |
| Group | Formulation | GMT | % sc | GMT | % sc |
| 1 | P6b 0.1 µg + alum | <20 | 40 | 1280 | 100 |
| 2 | P6b 1.0 µg + alum | 135 | 80 | 2229 | 100 |
| 3 | P6b 0.1 µg − alum | <20 | 0 | <20 | 0 |
| 4 | P6e 0.1 µg + alum | <20 | 20 | 640 | 100 |
| 5 | P6e 1.0 µg + alum | 30 | 100 | 905 | 100 |
| 6 | P6e 0.1 µg − alum | <20 | 0 | <20 | 20 |
| 7 | PBS | <20 | 0 | <20 | 0 |

Figure 14:
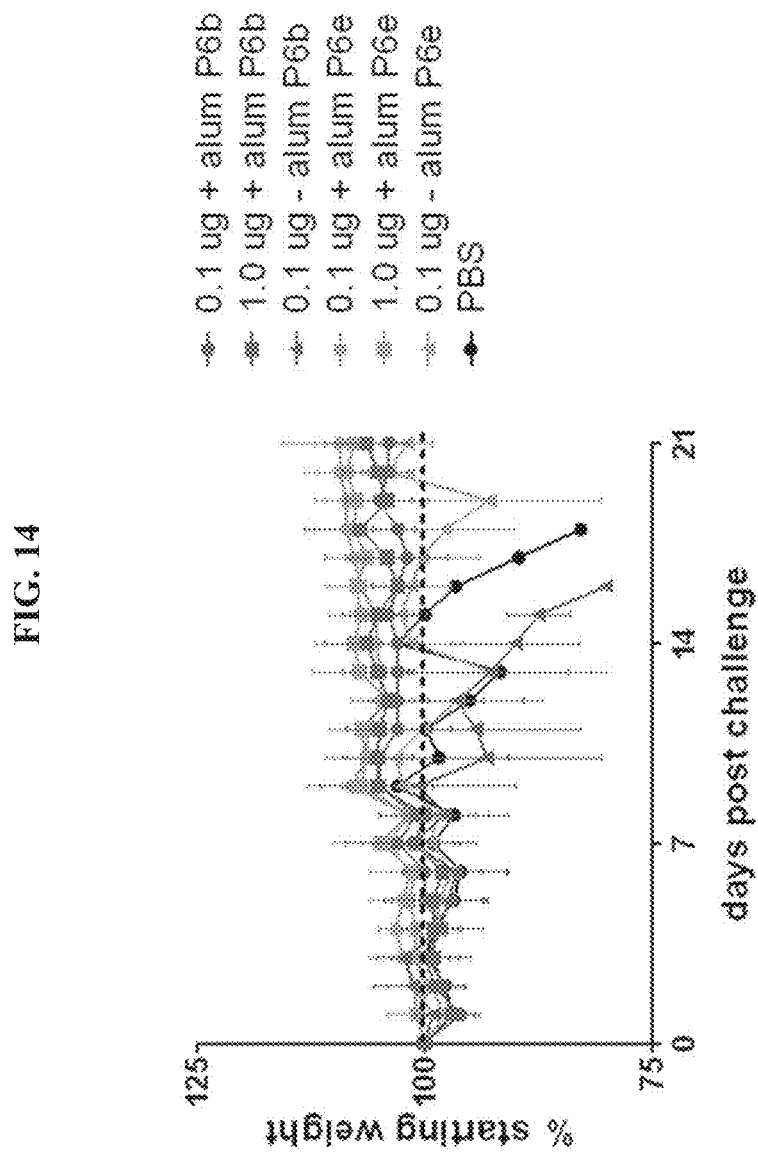
FIG. 14 shows the mean weight of AG129 test groups post-challenge, represented as a percentage of starting weight. Error bars represent standard deviation.
Figure 15:
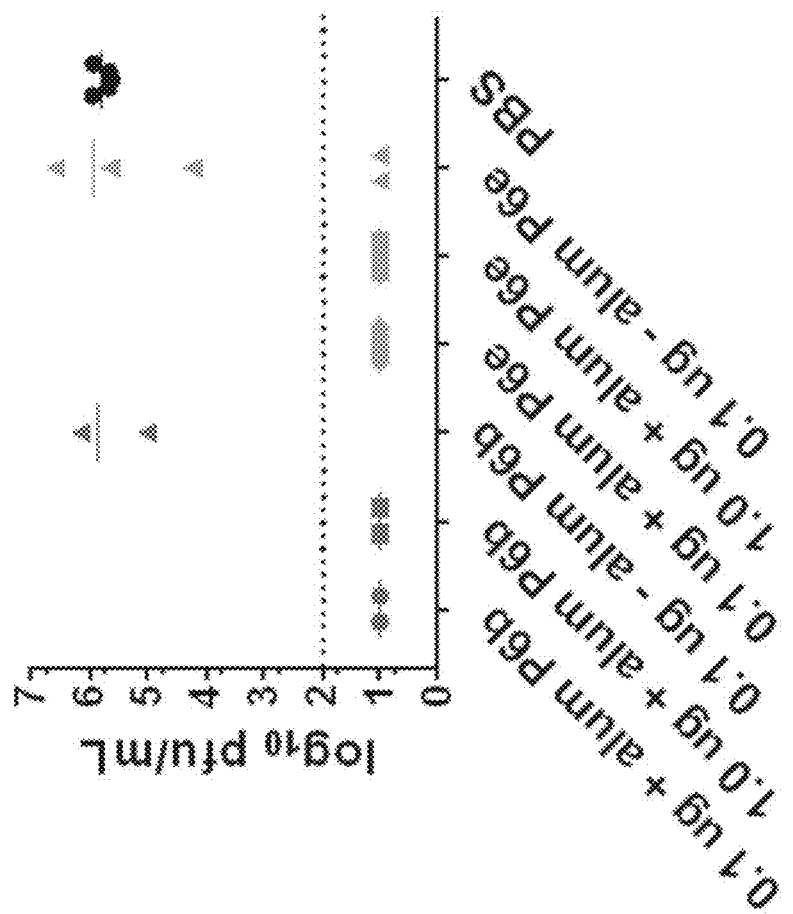
FIG. 15 shows the serum viremia of individual AG129 mice two days post-challenge, reported as PFU/mL. Solid lines represent the mean of a group. The limit of detection (2.0 $\log_{10}$) is represented by a dashed line.
Figure 16:
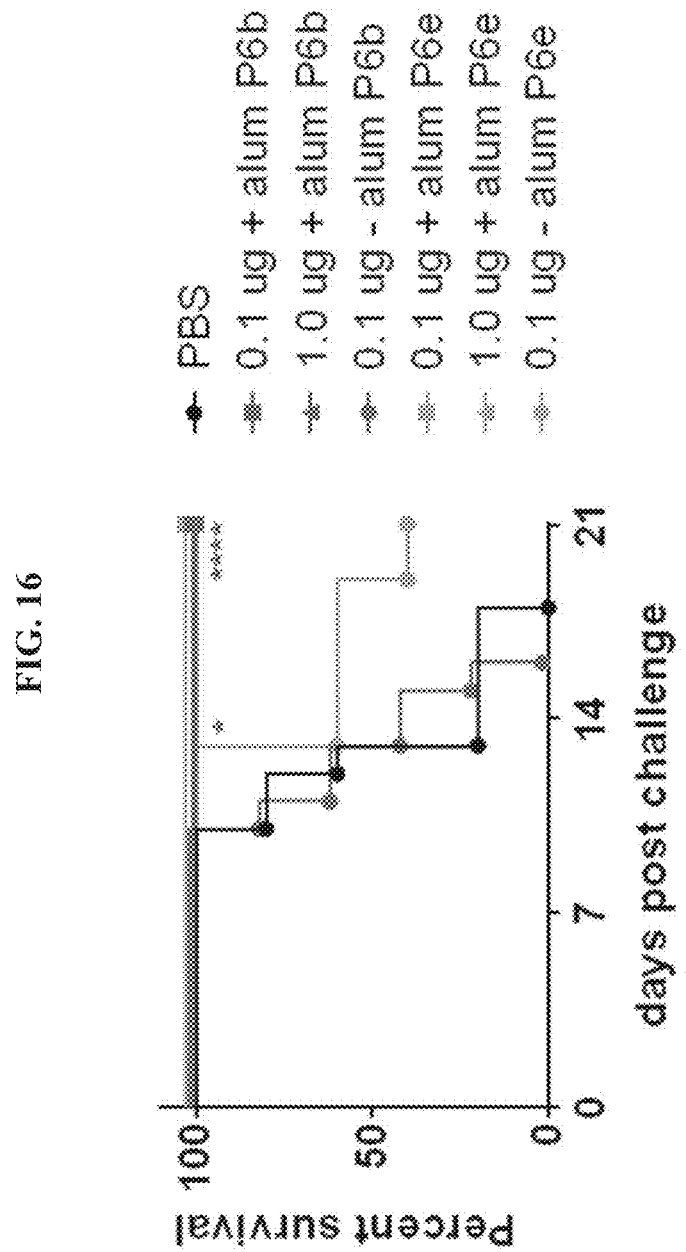
FIG. 16 shows the survival analysis of AG129 test groups post-challenge.

All groups were also monitored for mortality, morbidity and weight loss for 21 days post challenge. Viremia following challenge was detected and quantitated by plaque titration. Mice vaccinated with a low or high dose of PIZV candidates formulated with alum (groups 1, 2, 4 and 5) were fully protected from lethal ZIKAV challenge, as assessed by the plaque reduction neutralization test (PRNT) assay, as well as a comparable secondary neutralization assay (Table 8). No weight loss or clinical signs of illness were observed in vaccinated mice, none had detectable infectious viremia three days post challenge, and all mice vaccinated with either low or high dose antigen+alum adjuvant survived to 21 days post-challenge (FIGS. 14-16). In contrast, challenge of all naïve mice resulted in high viremia on day 2 post challenge and morbidity/mortality between day 10 and 18 post challenge (median survival=D13). Additionally, challenge of mice vaccinated with a non-alum-adjuvanted low dose vaccine derived from strain P6b resulted in high viremia on day 2 post challenge and a median survival day similar to the placebo control group, while mice vaccinated with a non-alum-adjuvanted low dose derived from clone e remained partially protected with a median survival of 19 days. These results indicate immunization is more effective with alum, secondary immunization may be a requirement, and that low dose was as effective as high dose.

TABLE 8

Serum neutralizing antibody titers

| | Serum neutralizing antibody titers Terminal (post challenge) | |
|---|---|---|
| Pool | $PRNT_{50}$ | Secondary assay |
| Alum (1, 2, 4, 5) | 10240 | 20480 |
| No alum (3, 6) | 2560 | 2560 |
| PBS (7) | 1280 | 1280 |

Additionally, the presence of NS1 in the vaccine drug substance (DS) produced from whole inactivated P7b and P7e virus (one additional passage from the P6b and P6e strains, respectively) was tested. A sandwich ELISA was performed using plates pre-coated with a monoclonal antibody reactive to both Asian and African lineages of Zika virus NS1, but non-cross-reactive to Dengue NS1. Duplicate 2-, 4-, 8-, 16-, and 32-fold dilutions of DS were prepared, and were compared to a standard curve using recombinant purified NS1 in duplicate at a concentration of 0-8 ng/mL. Duplicate dilutions of DS buffer alone were prepared as negative controls. Bound NS1 was detected with anti-NS1 HRP-conjugate, and absorbance ($A_{450}$-$A_{630}$) of the wells with DS buffer alone was subtracted from the absorbance measured in the wells containing the matching DS samples. Results of the sandwich ELISA are shown in Table 9 below. Interestingly, NS1 was observed to co-purify with the vaccine drug substance preparations, suggesting that viral NS1 may be an immunogenic component of the whole inactivated virus vaccine.

TABLE 9

NS1 ELISA

| Strain in vaccine preparation | Sample OD | Predicted log ng/mL | Std Error | Lower 95% | Upper 95% | Dilution Factor | Predicted concentration (ng/mL) |
|---|---|---|---|---|---|---|---|
| P7b | 3.61 | 0.951 | 0.018 | 0.915 | 0.986 | 32 | −285 |
| P7e | 3.79 | 0.980 | 0.023 | 0.935 | 1.024 | 32 | −306 |

The threshold of neutralizing antibody (Nab) needed to confer protection from wild-type Zika virus challenge after passive transfer of antibodies was next tested. (Tables 10A and B).

TABLE 10A design of passive transfer study in AG129 mice

| Group | Test Article | Serum dilution | Predicted Nab titer before IP |
|---|---|---|---|
| 1 | 100 µL | 1/3 | 6827/3.83 |
| 2 | 100 µL | 1/9 | 2276/3.36 |
| 3 | 100 µL | 1/27 | 759/2.88 |
| 4 | 100 µL | 1/81 | 253/2.40 |
| 5 | 100 µL | 1/243 | 84/1.93 |
| 6 | 100 µL | 1/729 | 28/1.45 |

TABLE 10A-continued design of passive transfer study in AG129 mice

| Group | Test Article | Serum dilution | Predicted Nab titer before IP |
|---|---|---|---|
| 7 | 100 µL | 1/2187 | 9/0.97 |
| 8 | 100 µL | PBS | — |

TABLE 10B

Timing of passive transfer study in AG129 mice

| Description | Study Day |
|---|---|
| Passive transfer | Day 0 |
| Primary Bleed (AM) | Day 1 |
| Challenge (PM) | Day 1 |
| Viremia Bleed | Day 4 |
| Terminal Bleed | Day 29 for survivors |

Figure 17:
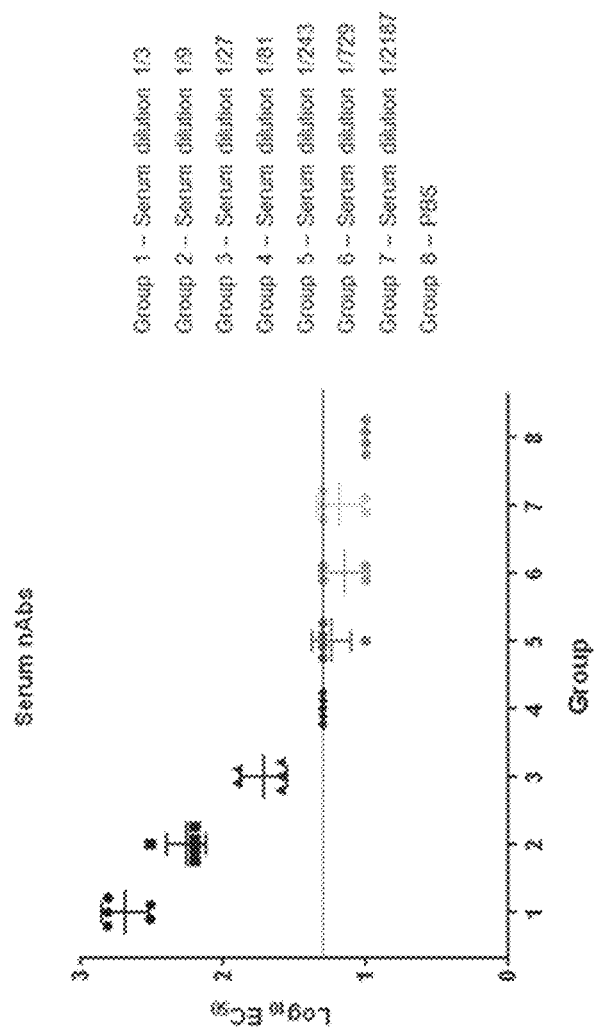
FIG. 17 shows the pre-challenge serum circulating ZIKAV neutralizing antibody (Nab) titers following passive transfer of pooled sera from vaccinated and challenged AG129 mice.

Pooled serum from vaccinated and challenged AG129 mice was serially diluted 3-fold in PBS and intraperitoneally injected into 7 groups (N=5/group) of 5-6 week old AG129 mice. Pre-immune AG129 mouse serum was used as placebo control (group 8). Following passive transfer (~16-19 hours later), whole blood was collected and serum was separated by centrifugation from each mouse prior to virus challenge for determination of circulating neutralizing antibody titer (FIG. 17). Just prior to virus challenge, groups of mice (designated groups 1, 2, 3, 4, 5, 6, 7, 8) had mean log 10 neutralizing antibody titers of 2.69, 2.26, 1.72, 1.30, <1.30, <1.30, <1.30, <1.30, respectively.

Twenty four hours following passive transfer of ZIKV nAbs, mice were intraperitoneally challenged with $10^4$ pfu of ZIKV PRVABC59. Following challenge, animals were weighed daily and monitored 1-3 times a day for 28 days for signs of illness. A clinical score was given to each animal based on the symptoms (Table 11). Animals that were moribund and/or showed clear neurological signs (clinical score ≥2) were humanely euthanized and counted as non-survivors.

TABLE 11

Description of clinical scores given while monitoring for morbidity and mortality

| Score | Description |
|---|---|
| 0 | Normal appearance and behavior |
| 1 | Slightly ruffled fur and/or general loss of condition |
| 2 | Increases in above behavior/appearance, breathing changes, twitching, anti-social behavior |
| 3 | First signs of neuropathy—Severely hunched posture, partial paralysis (immobility, unsteady gait, flaccid hind legs, severe twitching), or full paralysis |
| 4 | Found dead without showing signs of score of 2 or 3 first |

Figure 18:
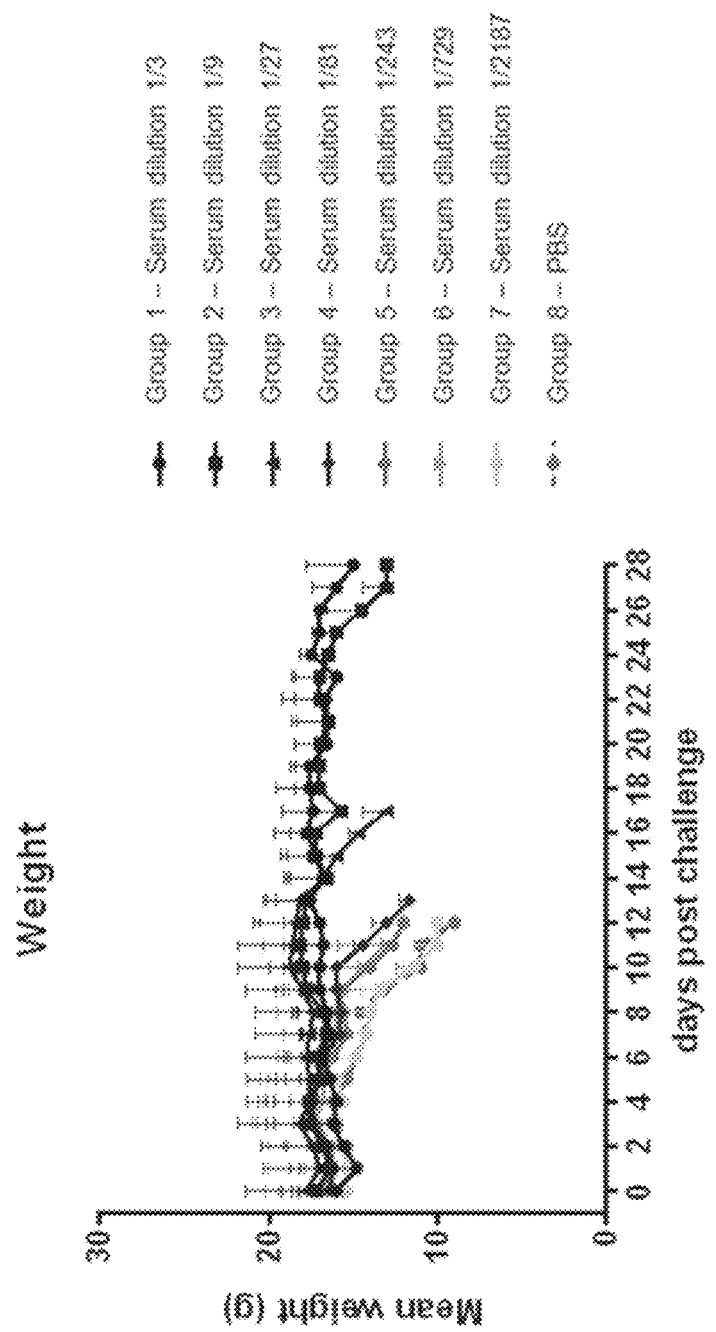
FIG. 18 shows the mean body weight of passive transfer and control mice challenged with Zika virus.
Figure 19:
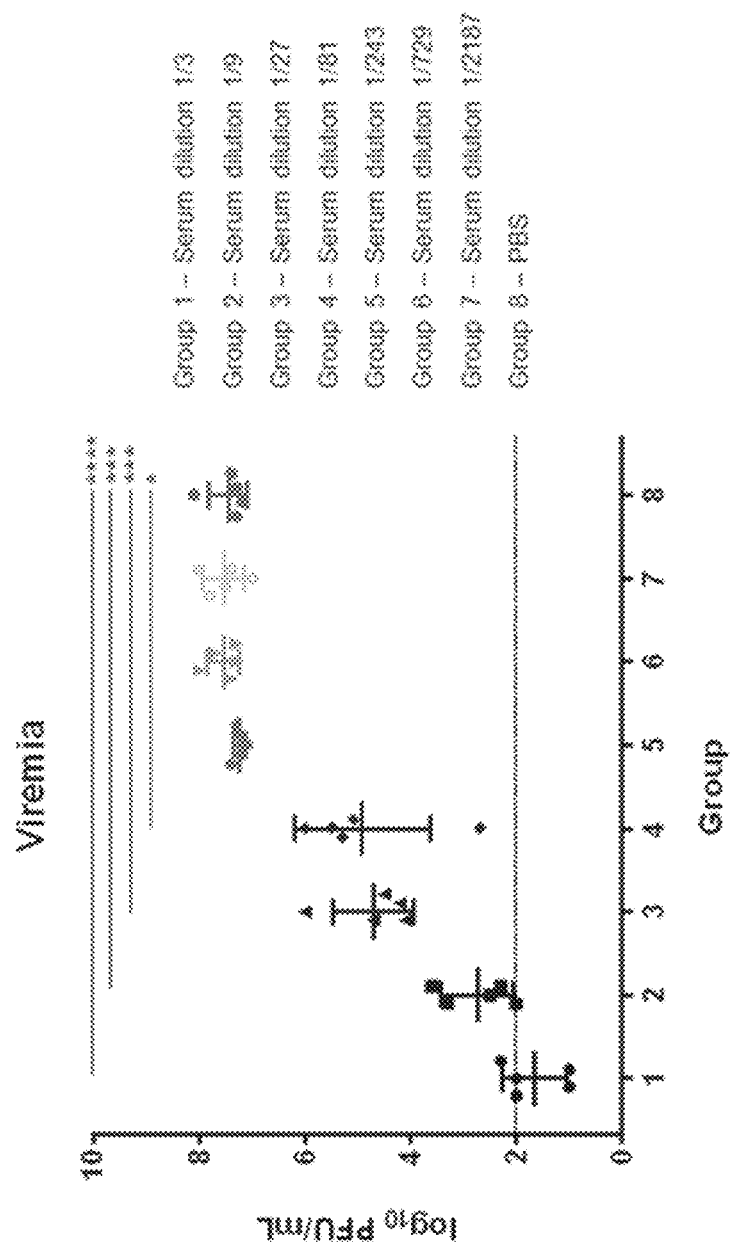
FIG. 19 shows the serum viremia of individual AG129 mice three days post-challenge, reported as PFU/mL.

Signs of disease began appearing nine days after challenge in the control group (group 8) and groups 5-7, with a corresponding loss in weight (FIG. 18). Whole blood was collected and serum was separated by centrifugation from each animal three days post challenge. Serum samples were analyzed for the presence of infectious ZIKV using a plaque titration assay (FIG. 19). The mean infectious titer ($log_{10}$ pfu/mL) for mice in groups 1-8 were: 1.66, 2.74, 4.70, 4.92, 7.24, 7.54, 7.54 and 7.46, respectively. Importantly, mice in groups 1-4 with detectable levels of ZIKV neutralizing antibodies (≥1.30 $log_{10}$) had statistically significant lower levels (102.5- to 106.0-fold lower titers) of viremia (p=0.0001, 0.0003, 0.0007 and 0.0374) than control mice. These results suggested that detectable levels of ZIKV neutralizing antibodies (≥1.30 log 10) reduced viremia in a dose-dependent manner.

Figure 20:
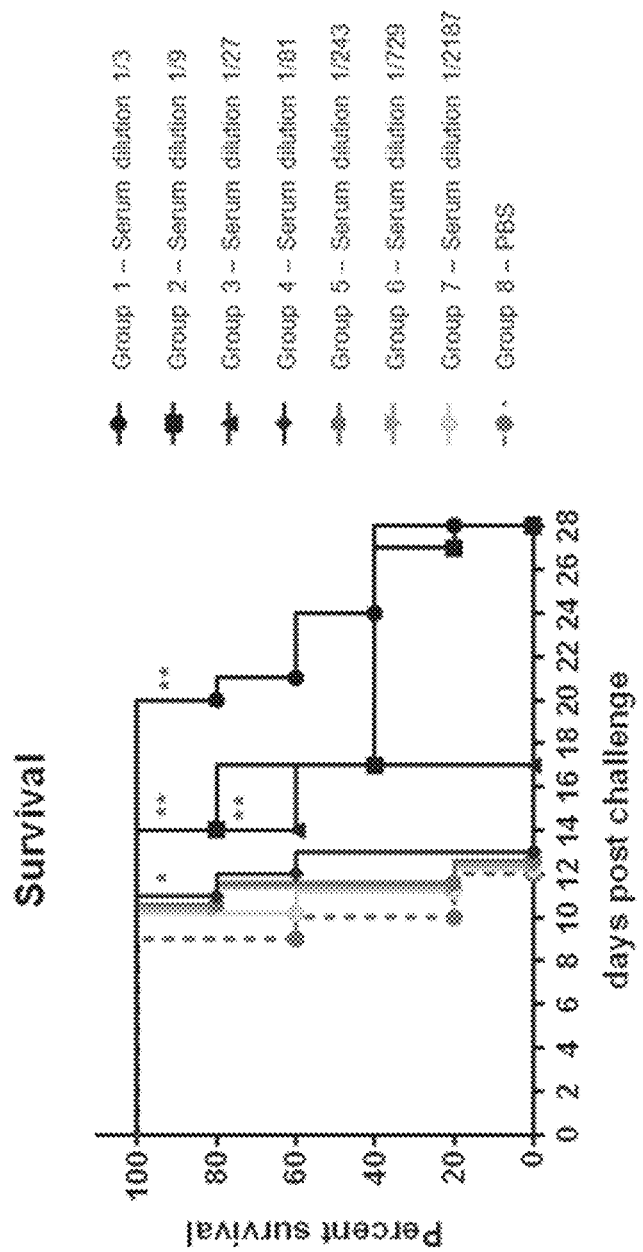
FIG. 20 shows the survival analysis of passive transfer and control mice challenged with Zika virus.

The median survival day of mice in groups 1-8 were: not determined, day 17, day 17, day 13, day 11, day 11, day 11, and day 10, respectively (FIG. 20). Importantly, the survival curves for groups of mice with detectable ZIKV neutralizing antibody titers (groups 1-4) were statistically different compared to the control group (group 8) (p=0.0019, 0.0019, 0.0019, 0.0153, respectively). These results suggested that detectable levels (≥1.30 $log_{10}$) of ZIKV neutralizing antibodies delayed onset of disease in a dose-dependent manner.

Figure 21:
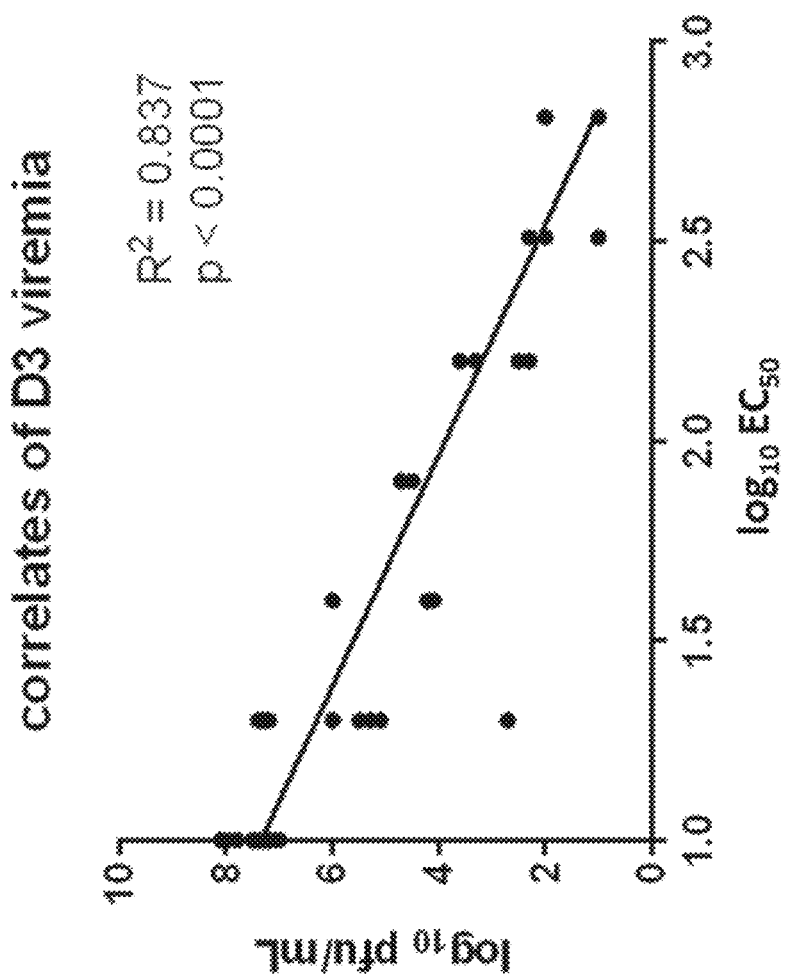
FIG. 21 shows the correlation between ZIKAV neutralizing antibody titers and viremia observed in passive transfer mice.

Finally, the ZIKV neutralizing antibody titer of each animal was graphed against its corresponding viremia titer and linear regression analysis was performed. A highly inversely correlated relationship between ZIKV neutralizing antibody titers and viremia levels at day 3 post-challenge was observed (FIG. 21). A summary of the results from the passive transfer studies is shown in Table 12 below.

TABLE 12

Summary of passive transfer results

| Group | Serum dilution | Circulating ZIKV nAb GMT | Viremia (D3) log10 pfu/mL | % survival (D28) | Median survival day |
|---|---|---|---|---|---|
| 1 | 1/3 | 2.69 ± 0.17 | 1.66 ± 0.62 | 20 | 24 |
| 2 | 1/9 | 2.26 ± 0.13 | 2.73 ± 0.68 | 0 | 17 |
| 3 | 127 | 1.72 ± 0.16 | 4.69 ± 0.77 | 0 | 17 |
| 4 | 1/81 | 1.30 ± 0.16 | 4.94 ± 1.29 | 0 | 13 |
| 5 | 1/243 | <1.30 | 7.25 ± 0.10 | 0 | 11 |
| 6 | 1/729 | <1.30 | 7.54 ± 0.31 | 0 | 11 |
| 7 | 1/2187 | <1.30 | 7.52 ± 0.39 | 0 | 11 |
| 8 | PBS | <1.30 | 7.47 ± 0.37 | 0 | 10 |

While no groups of mice receiving ZIKAV neutralizing antibodies were fully protected from lethal ZIKAV challenge in this experiment, reduced viremia levels and delayed onset of disease in a dose-dependent manner among the groups of mice with detectable levels of circulating ZIKAV neutralizing antibody titers was demonstrated.

Taken together, preclinical data from both CD-1 and AG129 mouse studies indicate that a PIZV derived from separate and well-characterized viral clones are immunogenic and able to provide protection against challenge with wild-type ZIKAV. Importantly, a low and high vaccine dose elicited a similar neutralizing antibody response after two doses, and provided similar levels of protection against lethal ZIKAV challenge. Interestingly, mice vaccinated with an unadjuvanted PIZV candidate also showed partial protection from ZIKAV challenge. Vaccine antisera significantly diminished viremia in passively immunized AG129 mice, and prolonged survival against lethal ZIKAV challenge. These results also demonstrate that the well-characterized PIZV candidates were highly efficacious against ZIKAV infection in the highly ZIKAV-susceptible AG129 mouse model.

Additionally, it was found that the sequence of a PRVABC59 (from PRVABC59 P6e) at passage 7 was genetically identical to that of passage 6. This was surprising given that flaviviruses are generally regarded as genetically labile. PRVABC59 P6e was selected as the pre-master virus seed due in part to its genetic stability over 7 passages. Without wishing to be bound by theory, it is believed that this enhanced genetic stability may be due to the single amino acid substitution (W98G) in the wing domain of NS1, as this was the only mutation observed in the Vero cell-adapted PRVABC59 P6 genome. Additionally, genetic stability and homogeneity is advantageous in that it reduces variability and increases reproducible production of subsequent strains that may be used for vaccine formulation.

Example 3: Preclinical Assessment of the Phenotype of the P6a and P6e Strains

Materials and Methods

AG129 mice (lacking interferon α/β and γ receptors) are susceptible to ZIKV infection and disease, including severe pathologies in the brain. 14-week-old AG129 mice were intraperitoneally infected with $10^4$ and $10^3$ pfu of the ZIKV passage 6 clones a and e.

Mice were weighed and monitored daily (up to 28 days) for clinical signs of illness (weight loss, ruffled fur, hunched posture, lethargy, limb weakness, partial/full paralysis). Additionally, analysis of viremia was performed by plaque titration of serum samples collected three days post-challenge as described in Example 1.

Results

Figure 22:
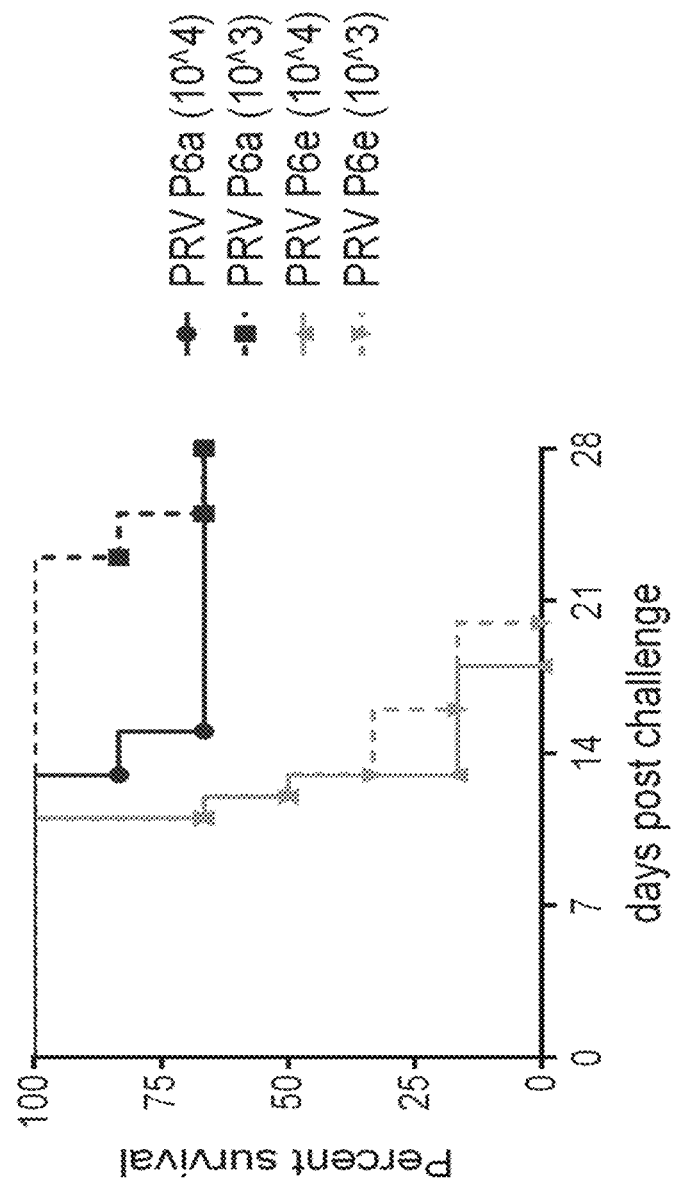
FIG. 22 shows the survival analysis of AG129 mice after infection with Zika virus preMVS stocks of P6a and P6e using a Kaplan Meier survival curve.
Figure 24:
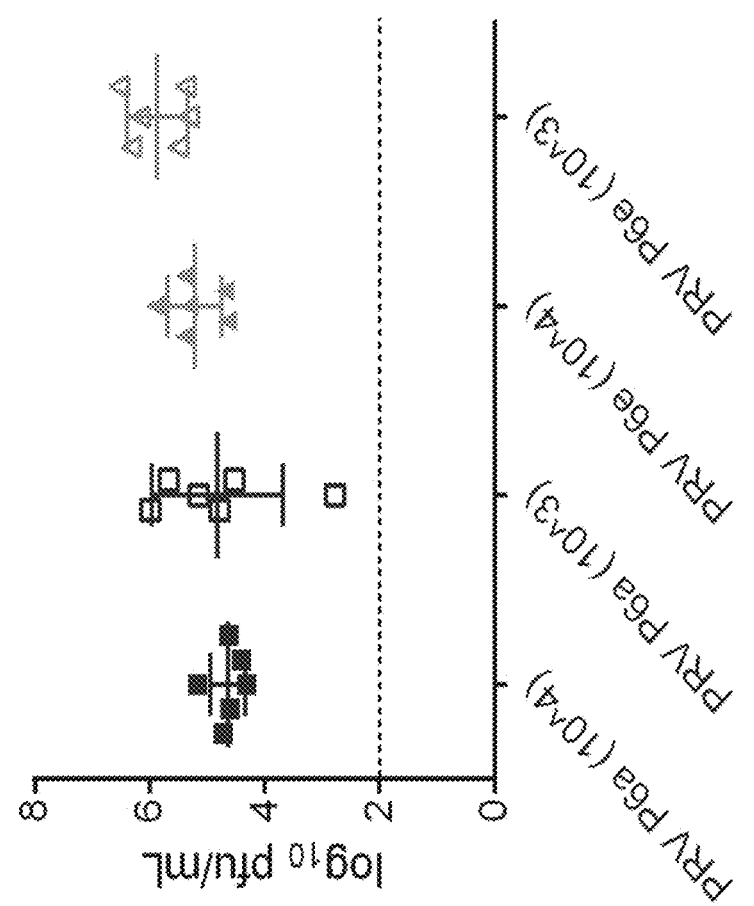
FIG. 24 shows the serum viremia of individual AG129 mice three days post-infection with Zika virus preMVS stocks of P6a and P6e, reported as PFU/mL. The dashed line represents the limit of detection of the assay.
Figure 25:
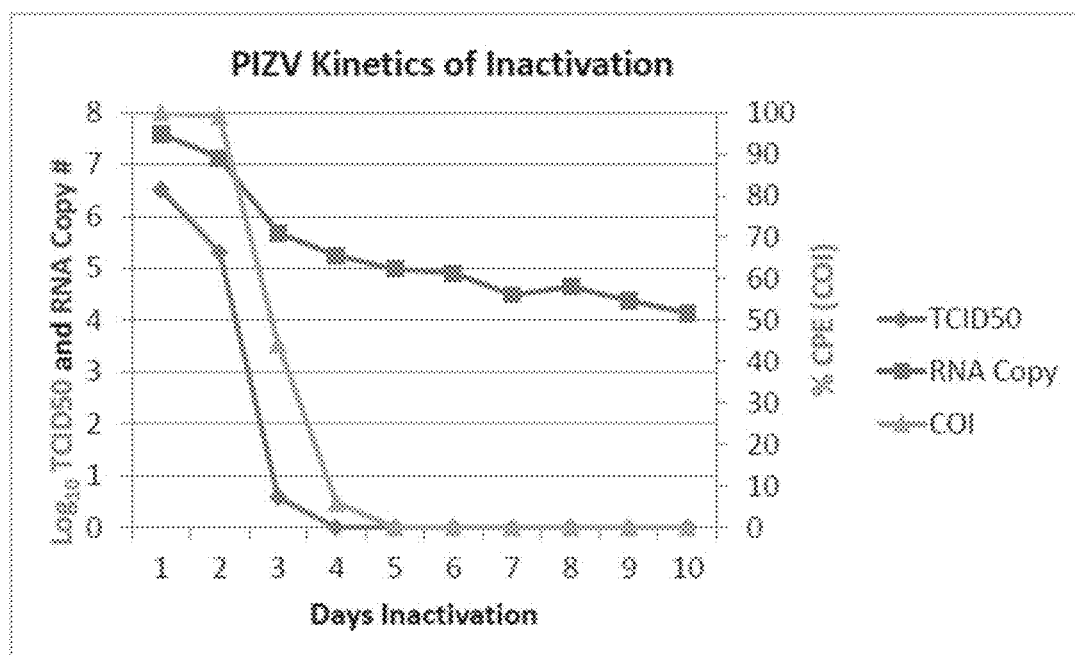
FIG. 25 shows compiled kinetics of inactivation data. Data compares infectious potency (TCID50) to RNA copy, and completeness of inactivation (COI) for samples from the four toxicology lots. These data indicate that the sensitivity of the COI assay is greater than TCID50.

Infection with preMVS P6e resulted in 100% mortality (median survival time=12.5 days), while infection with preMVS P6a resulted in only 33% mortality (median survival time=undetermined) (FIG. 22). In agreement with this, preMVS P6e infected mice showed greater weight loss as compared to PRVABC59 P6a infected mice (3). No statistical difference was found in mean group viremia levels between groups of mice infected with PRVABC59 P6a or P6e (FIG. 24). These data suggest that growth kinetics alone may not be a key determinant (since both strains produced similar viremia, and similar peak titers in vitro) and that a characteristic of the Envelope protein could be important for virulence (of a wildtype strain) and immunogenicity (of an inactivated candidate).

Example 4: Completeness of Inactivation Assay to Determine Effectiveness of Inactivation A double-infectivity assay also called completeness of inactivation (COI) assay was developed to determine the effectiveness of formalin-inactivation (0.01% formaldehyde) and potential residual infectious viral activity of purified inactivated zika virus (PIZV) bulk drug substance (BDS).

Sample preparation: Four Purified Inactivated Zika Vaccine (PIZV) lots (Tox lots 1-4) of clone e as described above were manufactured by growth in Vero cells. Supernatants from 4 daily harvests (totaling about 4000 mL) were purified by chromatography followed by addition of formaldehyde to a final concentration of 0.01%. w/v Inactivation was allowed to proceed for 10 days at 22° C. In Process Control (IPC) samples were removed on a daily basis from the bulk drug substance (BDS) during inactivation for characterization and analytics. The daily IPC samples were neutralized with sodium metabisulfite and dialysed into DMEM (viral growth media). The samples contain the purified inactivated Zika virus. On the final day of inactivation, the remaining volume of BDS samples was not neutralized, but was processed with TFF to remove formaldehyde and buffer exchanged into PBS.

Completeness of inactivation assay (COI): The COI assay was used for analysis of the effectiveness of inactivation in the daily IPC samples to understand the kinetics of inactivation, and the final BDS. For maximum sensitivity, two cell lines, Vero and C6/36, were initially utilized in this assay to detect potential live virus in the IPC and DS samples. When Zika virus infects Vero cells in the presence of growth medium containing phenol red, the by-products of cell death cause a drop in pH. Consequently, the media color changes from red/pink to yellow, indicative of this acidic shift in the media pH. This phenomenon is caused by the apoptosis and cytopathic effects (CPE), which refers to the observed changes in the cell structure of host cells that are caused by viral invasion, infection, and budding from the cells during viral replication. Ultimately, while both C6/36 mosquito and Vero cells are a permissive cell line for infection, Zika virus infection kills only Vero cells in vitro. Therefore, Vero cells were used as the indicator cell line for the assay. In contrast, C6/36 cells which are derived from a natural host vector for Zika virus do not exhibit a CPE upon Zika infection and do not lyse. The media does not change color and the viability of the C6/36 cells is not altered.

The assay is thus split in two parts: The first part of the assay allows for parallel amplification of potentially live viral particles on 96-well plates of the two susceptible cell lines for six days. The second step of the assay involves the transfer of the supernatant of the 96-well plates (including potentially amplified particles) onto 6-well plates containing monolayers of Vero cells, and incubation for another 8 days to allow for viral infection and a cytopathic effect to develop on the Vero cells. Any CPE observed was confirmed using a light microscope.

Although described in detail with respect to the use of 96 well plates in the first part of the assay, i.e. the culture in C6/36 cells, and six well plates in the second part of the assay, i.e. the culture of Vero cells to observe a cytophatic effect, the assay can be easily scaled up according to the following table:

| plate or flask | Surface area (cm²) | Recommended volume range (for growth) | mL sample per cm2 | Assay part 1: BDS application (must fall within recommended vol range) | | | Assay part 2: transfer to Vero (must accommodate pooled volume for transfer) | |
| | | | | vol inoculum per well (or per flask) | # vessels required for 15X scale-up; 2-fold dilution | # vessels required for 15X scale-up; 5-fold dilution | pooled volume for transfer (mL) | mL sample per cm2 | vol transferred inoculum per well (or flask) |
| 96-well format | 0.32 | 100-200 uL | 0.3125 | 0.1 | | | | |
| 12-well format | 3.8 | 0.076-1.14 ml | 0.3125 | 1.188 | 6.48 | 16.21 | 11.88 | |

| | | | Assay part 1: BDS application (must fall within recommended vol range) | | | | | Assay part 2: transfer to Vero (must accommodate pooled volume for transfer) | |
|---|---|---|---|---|---|---|---|---|---|
| plate or flask | Surface area (cm$^2$) | Recommended volume range (for growth) | mL sample per cm2 | vol inoculum per well (or per flask) | # vessels required for 15X scale-up; 2-fold dilution | # vessels required for 15X scale-up; 5-fold dilution | pooled volume for transfer (mL) | mL sample per cm2 | vol transferred inoculum per well (or flask) |
| 6-well format | 9.5 | 1.9-2.9 mL | 0.3125 | 2.969 | 4.32 | 10.81 | 17.81 | 0.0526 | 0.1 |
| T25 flask format | 25 | 5-7.5 mL | 0.3125 | 7.813 | 9.86 | 24.64 | 7.813 | 0.0526 | 1.32 |
| T75 flask format | 75 | 15-22.5 mL | 0.3125 | 23.438 | 3.29 | 8.21 | 23.438 | 0.0526 | 3.95 |
| T150 flask format | 150 | 30-45 mL | 0.3125 | 46.875 | 1.64 | 4.11 | 46.88 | 0.0526 | 7.89 |
| T175 flask format | 175 | 35-52.5 | 0.3125 | 54.688 | 1.41 | 3.52 | 54.69 | 0.0526 | 9.21 |
| T235 flask format | 235 | 47-70.5 | 0.3125 | 73.438 | 1.05 | 2.62 | 73.44 | 0.0526 | 12.36 |
| T300 flask format | 300 | 30-40 mL? | 0.3125 | 93.750 | 0.82 | 2.05 | 93.75 | 0.0526 | 15.78 |
| CF1 | 6/36 | 150-200 | 0.3125 | 198.750 | 0.39 | | | 0.0526 | 33.45 |
| CF2 | 1272 | 300-400 | 0.3125 | 397.500 | 0.19 | | | 0.0526 | 66.91 |
| CF10 | 63360 | 1500-2000 | 0.3125 | 19800.000 | 0.00 | | | 0.0526 | 3332.74 |

It is apparent that during the scale up the volume of sample per cm2 of vessel remains constant for part 1 and the same viral infection conditions are kept in part 2.

COI assay control: The titer and back titration controls for this assay were performed using Vero indicator cells and scored in a TCID$_{50}$ 96-well format with wells scored positive based on the media color change from pink to yellow, as a surrogate for cell death, or the presence of CPE.

Virus titer control test: Two independent replicates of the control virus (PRVABC59) of known titer were subjected to a 10-fold dilution series in media containing 2% FBS, and 100 µL of each dilution was added to four wells of a 96-well plate containing Vero cells. Plates were incubated for 5 days, then wells containing CPE were recorded and virus titer was calculated using the Reed-Meunch calculator.

Virus back titration control test: The control virus of known titer was serially diluted to 200 TCID50. Two independent replicates of the 200 TCID50 control virus were subjected to a 2-fold dilution series in media containing 2% FBS, and 100 µL of each dilution was added to four wells of a 96-well plate containing Vero cells. Cells were incubated for 5 days, then wells containing CPE were recorded and virus titer was calculated using the Reed-Meunch calculator.

Detailed COI Protocol:

1. First part of the assay: Vero (1.4E$^{+0.5}$ cells/mL) and *Aedes aegypti* mosquito C6/36 (4E$^{+0.5}$ cells/mL) cells were seeded in 96-well plates two days prior to addition of the samples. The Vero cells were cultured in DMEM+10% final FBS +2% L-glutamine+1% penicillin/streptomycin at 37° C. C6/36 cells were cultured in DMEM+10% FBS+2% L-glutamine+1% Penicillin/streptomycin +1% nonessential amino acids at 28° C.

2. Three independent replicates of the 200 TCID50 control virus (prepared in the virus back titration control test) or the DS samples were diluted (5-fold and 10-fold dilutions) into media containing 2% FBS.

3. The cells in 96-well plates were inoculated with the samples. Prior to the infection of the cell monolayers in the 96-well plates, the sample was vortexed to disrupt any possible aggregation. 100 µL of each dilution was applied to each of 5 wells into two separate 96-well plates containing Vero and C6/36 cells, respectively.

4. Media alone was included in another well for each cell type as a negative CPE control.

5. Plates were incubated for 6 days at the appropriate temperature for the cell line.

6. Second part of the assay: To allow live virus to be further amplified and visualized by CPE on a permissive cell line, the entire volume of each 96-well supernatant from both Vero and C6/36 cells was transferred to individual wells of 6-well plates of Vero cells. Inoculation proceeded for 90 minutes with rocking at 15 minutes intervals.

7. Medium containing 2% FBS was added to the wells and plates were incubated for an additional 8 days for subsequent detection of the amplified samples as a function of CPE. The inactivation was considered to be incomplete if any of the replicates of the DS showed CPE at the end of day 8.

7. The presence of live/replicating virions was visualized by the formation of plaques or CPE on susceptible cell monolayers after transfer to the 6-well plate, and incubation for 8 days to allow for viral replication. The % CPE scoring in the 6-well plates at the end of the assay was calculated as follows:

Each 6-well plate of Vero cells was examined for CPE by visualization of colorimetric change, followed by confirmation of CPE by inspection under an inverted light microscope.

Each 6-well plate represented one of the replicates of the DS dilutions prepared in the 5 and 10-fold dilutions described above (5 wells, plus one well containing media alone).

Therefore, % CPE for each replicate reflected the number of wells with CPE out of 5 total wells per sample (120 total wells are used per assay). Mean % CPE and standard deviation were calculated based on three replicates of each dilution.

Results: The daily samples were analyzed in each of the Tox lots #1-4 as shown in the following tables.

TABLE A

Kinetics of Inactivation, Tox lot #1

| Sample | Transfer | Mean % CPE | STDV |
|---|---|---|---|
| 1:10 Day-1 | Vero-to-Vero | 100 | 0 |
| 1:10 Day 0 | Vero-to-Vero | 100 | 0 |
| 1:10 Day 1 | Vero-to-Vero | 0 | 0 |
| 1:10 Day 2 | Vero-to-Vero | 0 | 0 |
| 1:10 Day 3 | Vero-to-Vero | 0 | 0 |
| 1:10 Day 4 | Vero-to-Vero | 0 | 0 |
| 1:10 Day 7 | Vero-to-Vero | 0 | 0 |
| 1:10 Day 8 | Vero-to-Vero | 0 | 0 |
| 1:10 Day 9 | Vero-to-Vero | 0 | 0 |
| 1:10 Day 10 | Vero-to-Vero | 0 | 0 |
| 100TCID50/mL | Vero-to-Vero | 100 | 0 |
| 1:10 Day-1 | C6/36-to-Vero | 100 | 0 |
| 1:10 Day 0 | C6/36-to-Vero | 100 | 0 |
| 1:10 Day 1 | C6/36-to-Vero | 6.7 | 12 |
| 1:10 Day 2 | C6/36-to-Vero | 13.3 | 12 |
| 1:10 Day 3 | C6/36-to-Vero | 0 | 0 |
| 1:10 Day 4 | C6/36-to-Vero | 0 | 0 |
| 1:10 Day 7 | C6/36-to-Vero | 0 | 0 |
| 1:10 Day 8 | C6/36-to-Vero | 0 | 0 |
| 1:10 Day 9 | C6/36-to-Vero | 0 | 0 |
| 1:10 Day 10 | C6/36-to-Vero | 0 | 0 |
| 100TCID50/mL | C6/36-to-Vero | 100 | 0 |

TABLE B

Kinetics of Inactivation, Tox lot #2

| Sample | Transfer | Mean % CPE | STDV |
|---|---|---|---|
| 1:10 Day-1 | Vero-to-Vero | 100 | 0 |
| 1:10 Day 0 | Vero-to-Vero | 100 | 0 |
| 1:10 Day 1 | Vero-to-Vero | 100 | 0 |
| 1:10 Day 2 | Vero-to-Vero | 0 | 0 |
| 1:10 Day 3 | Vero-to-Vero | 0 | 0 |
| 1:10 Day 4 | Vero-to-Vero | 0 | 0 |
| 1:10 Day 7 | Vero-to-Vero | 0 | 0 |
| 1:10 Day 8 | Vero-to-Vero | 0 | 0 |
| 1:10 Day 9 | Vero-to-Vero | 0 | 0 |
| 1:10 Day 10 | Vero-to-Vero | 0 | 0 |
| 100TCID50/mL | Vero-to-Vero | 100 | 0 |
| 1:10 Day-1 | C6/36-to-Vero | 100 | 0 |
| 1:10 Day 0 | C6/36-to-Vero | 100 | 0 |
| 1:10 Day 1 | C6/36-to-Vero | 100 | 12 |
| 1:10 Day 2 | C6/36-to-Vero | 13.3 | 12 |
| 1:10 Day 3 | C6/36-to-Vero | 0 | 0 |
| 1:10 Day 4 | C6/36-to-Vero | 0 | 0 |
| 1:10 Day 7 | C6/36-to-Vero | 0 | 0 |
| 1:10 Day 8 | C6/36-to-Vero | 0 | 0 |
| 1:10 Day 9 | C6/36-to-Vero | 0 | 0 |
| 1:10 Day 10 | C6/36-to-Vero | 0 | 0 |
| 100TCID50/mL | C6/36-to-Vero | 100 | 0 |

TABLE C

Kinetics of Inactivation, Tox lot #3

| Sample | Transfer | Mean % CPE | STDV |
|---|---|---|---|
| 1:10 Day-1 | Vero-to-Vero | 100 | 0 |
| 1:10 Day 0 | Vero-to-Vero | 100 | 0 |
| 1:10 Day 1 | Vero-to-Vero | 27 | 12 |
| 1:10 Day 2 | Vero-to-Vero | 0 | 0 |
| 1:10 Day 3 | Vero-to-Vero | 0 | 0 |
| 1:10 Day 4 | Vero-to-Vero | 0 | 0 |
| 1:10 Day 7 | Vero-to-Vero | 0 | 0 |
| 1:10 Day 8 | Vero-to-Vero | 0 | 0 |
| 1:10 Day 9 | Vero-to-Vero | 0 | 0 |
| 1:10 Day 10 | Vero-to-Vero | 0 | 0 |
| 100TCID50/mL | Vero-to-Vero | 100 | 0 |
| 1:10 Day-1 | C6/36-to-Vero | 100 | 0 |
| 1:10 Day 0 | C6/36-to-Vero | 100 | 0 |
| 1:10 Day 1 | C6/36-to-Vero | 87 | 12 |
| 1:10 Day 2 | C6/36-to-Vero | 27 | 12 |
| 1:10 Day 3 | C6/36-to-Vero | 0 | 0 |
| 1:10 Day 4 | C6/36-to-Vero | 0 | 0 |
| 1:10 Day 7 | C6/36-to-Vero | 0 | 0 |
| 1:10 Day 8 | C6/36-to-Vero | 0 | 0 |
| 1:10 Day 9 | C6/36-to-Vero | 0 | 0 |
| 1:10 Day 10 | C6/36-to-Vero | 0 | 0 |
| 100TCID50/mL | C6/36-to-Vero | 100 | 0 |

TABLE D

Kinetics of Inactivation, Tox lot #4

| Sample | Transfer | Mean % CPE | STDV |
|---|---|---|---|
| 1:10 Day-1 | Vero-to-Vero | 100 | 0 |
| 1:10 Day 0 | Vero-to-Vero | 93 | 12 |
| 1:10 Day 1 | Vero-to-Vero | | 0 |
| 1:10 Day 2 | Vero-to-Vero | 0 | 0 |
| 1:10 Day 3 | Vero-to-Vero | 0 | 0 |
| 1:10 Day 4 | Vero-to-Vero | 0 | 0 |
| 1:10 Day 7 | Vero-to-Vero | 0 | 0 |
| 1:10 Day 8 | Vero-to-Vero | 0 | 0 |
| 1:10 Day 9 | Vero-to-Vero | 0 | 0 |
| 1:10 Day 10 | Vero-to-Vero | 0 | 0 |
| 100TCID50/mL | Vero-to-Vero | 100 | 0 |
| 1:10 Day-1 | C6/36-to-Vero | 100 | 0 |
| 1:10 Day 0 | C6/36-to-Vero | 100 | 0 |
| 1:10 Day 1 | C6/36-to-Vero | 33 | 23 |
| 1:10 Day 2 | C6/36-to-Vero | 7 | 12 |
| 1:10 Day 3 | C6/36-to-Vero | 0 | 0 |
| 1:10 Day 4 | C6/36-to-Vero | 0 | 0 |
| 1:10 Day 7 | C6/36-to-Vero | 0 | 0 |
| 1:10 Day 8 | C6/36-to-Vero | 0 | 0 |
| 1:10 Day 9 | C6/36-to-Vero | 0 | 0 |
| 1:10 Day 10 | C6/36-to-Vero | 0 | 0 |
| 100TCID50/mL | C6/36-to-Vero | 100 | 0 |

Compiled kinetics of inactivation data: COI data for samples from the four toxicology lots were compared to infectious potency (TCID50) determined as described above and to RNA copy. The RNA copy was determined by purifying nucleic acids from the sample and amplifying Zika RNA with serotype-specific primers using an RT-PCR kit. The result shown in FIG. 25 shows that the sensitivity of the COI assay is significantly greater than that of TCID50.

Performance characteristics of the COI assay—Accuracy: The target dilutions (TCID50/well) and their respective proportions of CPE were used to determine relative accuracy. For the Vero cells, there was a statistically significant linear relationship between the observed and expected proportions of positive CPE. The slope of the line relating observed and expected results is 0.92 with a 95% confidence interval (CI) of 0.83 to 1.01 that overlaps 1 indicate 100% accuracy. For the C6/36 cells, there is a statistically significant linear relationship between the observed and expected proportions of positive CPE. The slope of the line relating observed and expected results is 0.88 with a 95% confidence interval (CI) of 0.80 to 0.95 indicate that a slight bias (5-20%) was seen with this cell line. Both cell lines demonstrate satisfactory accuracy (relative).

Performance characteristics of the COI assay—Limit of Detection (LoD): The sensitivity of the assay was assessed for both the C6/36-to-Vero and Vero-to-Vero plates. As described above, the data was fitted using least squares regression of the proportion of +ve CPE observed per total wells plated with titer dilutions plated starting at 10.00 TCID50/well down to a lower titer of 0.08 TCID50. Furthermore, negative controls (0.00 TCID50/well) were included for each dilution within the plates. CPE scoring was performed for each dilution across both the C6/36-to-Vero and Vero-to-Vero plates. A clear relationship between the CPE and log input virus titer was seen. This displays the logistic (sigmoidal) relationship between the proportion of CPE positive wells relative to the log 10 concentration of TCID50/well together with a lower and upper 99% confidence limit At a −2 log 10 concentration (=0.01 TCID50/well), a model based on and accounting for all fixed and random sources variation in the qualification data predicted 0.85%, or 0.01 when rounded up at 0.01 TCID50/well, with a lower 99% confidence limit of 0.42%. Since the lower 99% confidence limit does not include zero, there is a very small quantifiable (<1%) chance the 0.85% CPE wells could have arisen from 0 TCID50/well (i.e., due to noise). This establishes a detection limit for the assay of at least 0.01 TCID50/well (i.e., the lowest amount of live Zika particles in the sample which can be detected). That is, when rounded up, 1 in 60 wells will be CPE positive or given these parameters, the lowest theoretical proportion of the CPE+ve that could be detected in 60 wells would be 1.67%, or 0.0167.

The cell types (C363 and Vero) were compared for relative sensitivity, with the C6/36 demonstrating that a lower dilution of virus titer could be detected compared to Vero cells as shown in FIG. 26; at the same virus input level (0.31 TCID50), the proportion of CPE positive wells is higher for C6/36 relative to Vero cells.

Figure 27:
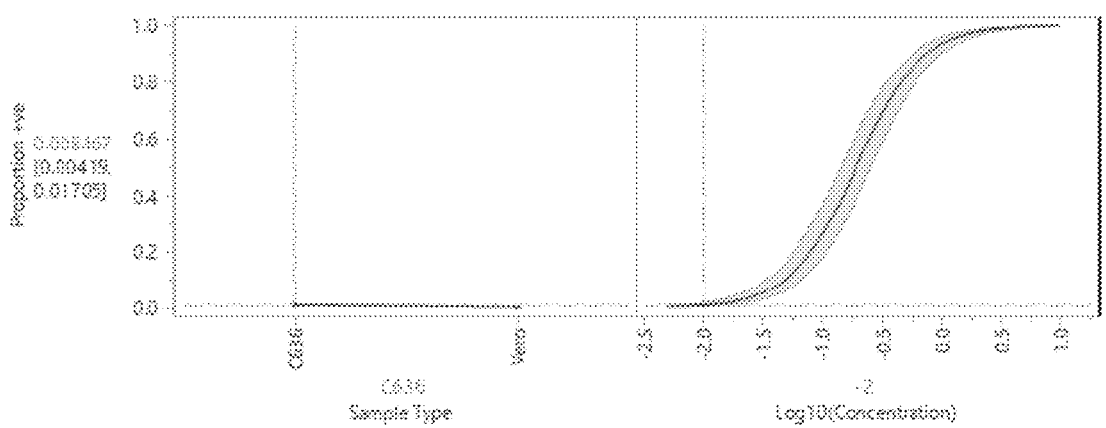
FIG. 27 shows a logistic regression analysis of CPE vs. log TCID50 using C6/36 cells site that include 99% confidence intervals around a target value of 0.01 TCID50/well (−2 log TCID50/well); the model predicts 0.85% of wells will be positive.

The lowest virus input value used during the qualification of this assay was 0.02 TCID50 (−1.61 log TCID50). Using the fitted curve for C6/36 cells, this results in 0.035 or 3.5% of the wells scoring CPE positive (1 in 28 wells). If the curve is extrapolated towards the lowest practical level of 0.167 or 1.6%, then this equates to a virus input level of 0.015 TCID50 (−1.82 log TCID50). However, the impact of transmitted assay variance needs to be considered when determining the lowest levels of infectious virus that can be detected as reflected in the +ve CPE results. This noise arises from generation of the working stock of input virus. Comparison of the target TCID50 and the back-titration calculation shows the TCID50 of the working stock virus exhibited a standard deviation (SD) of 85 TCID50/mL, derived from a mean of 213 when targeting a stock TCID50/mL concentration of 200. The % CV calculates to ~40% with a bias of about +7%. This noise was factored into the logistic regression model to generate confidence intervals around the targeted values for the virus dilutions. At a target value of 0.01 TCID50/well, a model based on and accounting for all fixed and random sources of variation in the qualification data across the two sites predicts 0.86% of wells will be CPE positive (1 in 60 wells). Since the lower 99% confidence limit does not include zero, there is a very small quantifiable (<1%) chance the 0.85% CPE-positive wells could have arisen from 0 TCID50/well due to noise (FIG. 27). This establishes a detection limit for the assay: 0.01 TCID50/well is the lowest amount of live Zika particles in the sample which can be detected.

Performance characteristics of the COI assay—Range: The range of the assay was 0.01 TCID50/well to 4.5 TCID50/well and is defined as the range of input virus that resulted in a CPE+ve proportion scoring of more than 0% but less than 100%.

Conclusion: Analysis of the four Tox revealed that inactivation was complete after incubation in 0.01% formaldehyde for 10 days at room temperature. Inactivation was achieved by days 3-4 in all lots produced, as measured by the COI assay. The COI assay is more sensitive than TCID50 potency or RNA measurements; the increased sensitivity has also been observed by LoD.

Example 5: Determining Residual Formalin Content in a Pharmaceutical Composition 1. Materials and Methods
1.1 Materials Formaldehyde standard solution (in methanol) (982 µg/mL), DNPH, HPLC-grade acetonitrile, and phosphoric acid were purchased from Wako Pure Chemicals Co. (Tokyo, Japan). Distilled water used for diluting phosphoric acid was obtained from Otsuka Pharmaceutical (Tokushima, Japan). Alhydrogel® 2% (corresponding to 10 mg/mL aluminum) used as aluminum hydroxide gel was obtained from Brenntag (Frederikssund, Denmark). PBS was prepared in-house, and the Zika vaccine drug product containing aluminum hydroxide gel was manufactured as described below. The Zika virus was purified with various techniques after harvest. After inactivation with formaldehyde, the virus was concentrated, and the buffer was exchanged with PBS by filtration. The bulk drug substance was diluted with PBS and formulated with aluminum hydroxide gel (0.4 mg/mL aluminum) to form the final drug product.

1.2 HPLC Conditions

A Waters HPLC alliance system equipped with a UV detector (Milford, USA) and a reverse-phase column (YMC-Pack ODS-A, 4.6 mm×250 mm, 5 µm (Kyoto, Japan)) was used. A mixture of water and acetonitrile (1:1, v/v) was used as the mobile phase, the detection wavelength was set at 360 nm, and the flow rate was 1.0 mL/min. The column temperature and injection volume were 25° C. and 50 µL, respectively.

1.3 Sample Preparation

The vaccine drug product (1.2 mL) was centrifuged at 15000 rpm for 10 min, and the supernatant (1 mL) was transferred into a 2-mL HPLC glass vial purchased from Waters (Milford, USA). Next, 20 µL of 20% (v/v) phosphoric acid and 50 µL of 1.0 mg/mL DNPH solution in acetonitrile were added, and the mixture was stirred and left at room temperature for 20 min before injection.

1.4 Method Validation

According to the ICH Q2 guidelines, the method was validated in terms of specificity, linearity, accuracy, repeatability, intermediate precision, robustness, and stability of the sample. In the accuracy study, the Zika vaccine drug product and aluminum hydroxide gel solution were spiked with a specific amount of formaldehyde, and the sample was mixed well by vortex before following the procedure described in Section 2.3.

2. Results and Discussion

2.1 Linearity and Specificity

Figure 28:
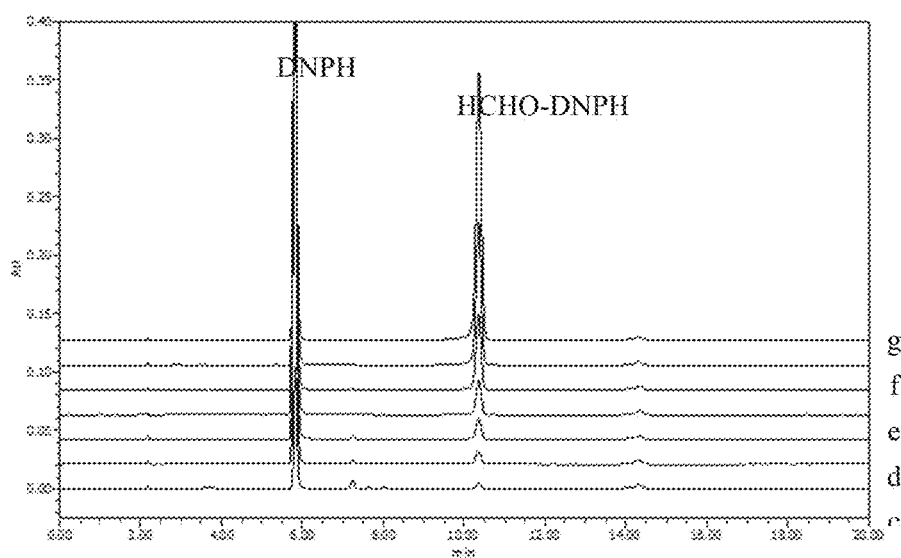
FIG. 28 shows chromatograms of PBS (a) and PBS solutions containing 0.049 μg/mL (b), 0.098 μg/mL (c), 0.196 μg/mL (d), 0.491 μg/mL (e), 0.982 μg/mL (f), and 1.964 μg/mL (g) formaldehyde.

Six standard solutions of formaldehyde (0.049, 0.098, 0.196, 0.491, 0.982, and 1.964 µg/mL) were prepared by dilution with PBS. Next, 20% (v/v) phosphoric acid and 1 mg/mL DNPH solution in acetonitrile were added to each solution, and the corresponding chromatograms are shown in FIG. 28. Clearly, the 10.4-min peak area showed linearity with the regression equation: y=1075730x+11731 (where y is the area of the 10.4-min peak and x is the concentration of formaldehyde in µg/mL) (correlation coefficient: 0.9998), indicating that it was due to HCHO-DNPH (i.e., formaldehyde derivatized with DNPH). Moreover, the peak at 5.8 min was attributed to DNPH as it was detected in all samples added with DNPH. Hence, the HCHO-DNPH peak area was used for evaluation of linearity and accuracy after subtracting the background peak area in PBS.

2.2 Accuracy and Precision (Repeatability)

The effect of aluminum hydroxide adjuvant was evaluated by recovery studies, which were carried out by spiking three samples of aluminum hydroxide (0.1, 0.4, and 1.0 mg/mL aluminum) in PBS with 0.05 µg/mL of formaldehyde in the absence of the vaccine drug substance. The average recoveries were 102% (n=3), 100% (n=3), and 100% (n=3), respectively, with low relative standard deviation (RSD) values (Table 13). The RSD of the accuracy data was calculated to evaluate the repeatability, and was found to be 1.0%, indicating that aluminum amounts up to 1.0 mg/mL did not interfere with the recovery of formaldehyde.

TABLE 13

Accuracy and repeatability evaluated using aluminum hydroxide samples spiked with 0.05 µg/mL of formaldehyde

| Aluminum hydroxide concentration [mg/mL aluminum] | Average (n = 3) [%] (RSD [%]) |
|---|---|
| 0.1 | 102 |
|  | (0.2) |
| 0.4 | 100 |
|  | (0.8) |
| 1.0 | 100 |
|  | (0.3) |
| Repeatability [%] (n = 9) | 1.0 |

The accuracy of the method was evaluated by recovery studies, which were carried out by spiking the Zika vaccine drug product containing aluminum hydroxide adjuvant with three concentrations of formaldehyde (0.05, 0.10, and 1.00 µg/mL), and the average recovery results are shown in Table 14. The RSD of the accuracy data was calculated to evaluate the repeatability, and was found to be 3.7%, indicating that Zika vaccine drug products formulated with aluminum hydroxide do not interfere with the recovery of formaldehyde between 0.05 and 1.00 µg/mL.

TABLE 14

Accuracy and repeatability evaluated using Zika vaccine drug products containing aluminum hydroxide spiked with formaldehyde

| Spiked formaldehyde concentration [µg/mL] | Average SD [%] |
|---|---|
| 0.05 | 102 |
|  | (5.6) |
| 0.10 | 97 |
|  | (0.3) |
| 1.00 | 98 |
|  | (0.7) |
| Repeatability [%] (n = 9) | 3.7 |

2.4 Robustness

The robustness of the method was evaluated to determine how concentration of formaldehyde in samples would be affected by variations in experimental parameters during sample preparation. Considering impact on the derivatization efficacy, concentration of DNPH and phosphoric acid were selected as the monitored parameters in this study. The effect was examined by varying the concentrations of DNPH and phosphoric acid by ±0.1 mg/mL and ±5%, respectively. Formaldehyde was determined in two development drug product lots under each condition, and the results, shown in Table 15, suggest that variations in DNPH and phosphoric acid concentrations had no significant impact on the determination of formaldehyde.

TABLE 15

Robustness of the method

| Condition | Concentration of DNPH [mg/mL] | Concentration of phosphoric acid [%] | Concentration of formaldehyde [µg/mL] Lot B | Lot C |
|---|---|---|---|---|
| 1* | 1.0 | 20 | 0.51 | 0.45 |
| 2 | 1.1 | 20 | 0.53 | 0.48 |
| 3 | 0.9 | 20 | 0.49 | 0.47 |
| 4 | 1.0 | 15 | 0.52 | 0.49 |
| 5 | 1.0 | 25 | 0.52 | 0.48 |

*Defined conditions of the method

---

The invention claimed is:

1. A method for determining the completeness of inactivation of an arbovirus preparation, comprising, the steps of: (i) inoculating, cultured insect cells with an arbovirus preparation which was subjected to an inactivation step and incubating the insect cells for a first period of time, thereby producing an insect cell supernatant; (ii) inoculating cultured mammalian cells with the insect cell supernatant produced in (i) and incubating the mammalian cells for a second period of time; and (iii) determining whether the arbovirus preparation contains a residual replicating virus that produces a cytopathic effect on the mammalian cells.

2. The method of claim 1, wherein the insect cells are selected from CCL-125 cells, Aag-2 cells, RML-12 cells, C6/36 cells, C7-10 cells, AP-61 cells, A.t. GRIP-1 cells, A.t. GRIP-2 cells, A.t. GRIP-3 cells, UM-AVE1 cells, Mos.55 cells, Sua1B cells, 4a-3B cells, Mos.42 cells, MSQ43 cells, LSB-AA695BB cells, NIID-CTR cells and TRA-171 cells.

3. The method of claim 2, wherein the insect cells are C6/36 cells.

4. The method of claim 1, wherein the first period of time is 3 to 7 days.

5. The method of claim 1, wherein the mammalian cells are selected from Vero cells, LLC-MK2 cells, MDBK cells, MDCK cells, ATCC CCL34 MDCK (NBL2) cells, MDCK 33016 (deposit number DSM ACC 2219), BHK21-F cells, HKCC cells and Chinese hamster ovary cells (CHO cells).

6. The method of claim 5, wherein the mammalian cells are Vero cells.

7. The method of claim 1, wherein the second period of time is 3 to 14 days.

8. The method of claim 1, wherein the method is capable of detecting less than 1.0 TCID50 of the arbovirus.

9. The method of claim 1, wherein the arbovirus preparation was subjected to a treatment with detergent, formaldehyde, hydrogen peroxide, beta-propiolactone (BPL), binary ethylamine (BET), acetyl ethyleneimine, methylene blue, or psoralen.

10. The method of claim 1, wherein the arbovirus is a flavivirus or an alphavirus.

11. The method of claim 10, wherein the arbovirus is a Zika virus, a West Nile virus, a Yellow Fever virus, a Japanese Encephalitis virus, a tick borne-encephalitis virus, a dengue virus, a St. Louis Encephalitis virus, a Chikungunya virus, a O'nyong'nyong virus or a Mayarovirus.

12. The method of claim 11, wherein the arbovirus is a Zika virus.

13. The method according to claim 12, wherein the method for determining the completeness of inactivation of a Zika virus preparation, comprises:
  (i) inoculating C6/36 cells with a Zika virus preparation which was subjected to an inactivation step and incubating the C6/36 cells for a first period of tune, thereby producing a C6/36 cell supernatant;
  (ii) inoculating Vero cells with the C6/36 cell supernatant produced in (i) and incubating the Vero cells for a second period of time, and
  (iii) determining whether the Zika virus preparation contains a residual replicating virus that produces a cytopathic effect on the Vero cells.

14. The method of claim 13, wherein the first period of time is 3 to 7 days.

15. The method of claim 13, wherein the second period of time is 3 to 14 days.

16. A pharmaceutical composition comprising an inactivated Zika virus preparation, wherein the inactivated Zika virus preparation comprises less than 1.0 TCID50 of residual replicating virus as determined by the method of claim 1.

17. The pharmaceutical composition according to claim 16, having a residual formaldehyde content of less than 0.5 µg/mL.

* * * * *